United States Patent [19]
Grell et al.

[11] Patent Number: 6,143,769
[45] Date of Patent: *Nov. 7, 2000

[54] PHENYLACETIC ACID BENZYLAMIDES

[75] Inventors: Wolfgang Grell; Rudolf Hurnaus, both of Biberach; Gerhart Griss, deceased, late of Biberach, by Elisabeth Griss, executrix; Robert Sauter, Laupheim; Manfred Reiffen, Biberach; Eckhard Rupprecht, Aulendorf-Tannhausen, all of Germany

[73] Assignee: Karl Thomae GmbH, Biberach an der Riss, Germany

[*] Notice: This patent is subject to a terminal disclaimer.

[21] Appl. No.: 08/180,587

[22] Filed: May 9, 1994

Related U.S. Application Data

[63] Continuation of application No. 07/919,820, Jul. 24, 1992, Pat. No. 5,312,924, which is a continuation-in-part of application No. 07/495,820, Jun. 21, 1990, Pat. No. 5,216,167, which is a continuation of application No. 07/302,022, Jan. 25, 1989, abandoned, which is a continuation-in-part of application No. 06/878,921, Jun. 26, 1986, abandoned, said application No. 07/302,022, and a continuation-in-part of application No. 06/872,706, Jun. 10, 1986, abandoned, which is a continuation-in-part of application No. 06/684,054, Dec. 20, 1984, abandoned.

[30] Foreign Application Priority Data

| Dec. 30, 1983 | [DE] | Germany | 33 47 565 |
| Jun. 25, 1985 | [DE] | Germany | 35 22 604 |
| Jul. 1, 1985 | [DE] | Germany | 35 23 466 |

[51] Int. Cl.⁷ ..................... A61K 31/445; C07D 211/08
[52] U.S. Cl. .................................... 514/331; 546/234
[58] Field of Search ........................ 546/234; 514/331

[56] References Cited

U.S. PATENT DOCUMENTS

| 3,647,804 | 3/1972 | Rynbrandt et al. | 546/233 |
| 3,674,944 | 7/1972 | Shen et al. | 514/866 |
| 3,678,094 | 7/1972 | Shen et al. | 514/866 |
| 3,692,821 | 9/1972 | Sarett et al. | 546/234 |
| 4,158,063 | 6/1979 | Hitzel et al. | 514/866 |
| 4,385,066 | 5/1983 | Ainsworth et al. | 514/866 |
| 4,542,127 | 9/1985 | Hiztel | 546/194 |
| 4,735,959 | 4/1988 | Grell et al. | 546/234 |
| 4,863,724 | 9/1989 | Schepky et al. | 424/80 |
| 4,873,080 | 10/1989 | Brickl et al. | 424/80 |
| 5,216,167 | 6/1993 | Grell et al. | 246/234 |

FOREIGN PATENT DOCUMENTS

| 0147830 | 10/1985 | European Pat. Off. . | |
| 2090834 | 7/1982 | United Kingdom | 546/234 |
| 2091729 | 8/1982 | United Kingdom | 546/234 |
| 2100261 | 12/1982 | United Kingdom | 514/866 |
| 2124220 | 2/1984 | United Kingdom | 514/866 |

OTHER PUBLICATIONS

Frahm & Knapp, Tetrahedron Letters, vol. 22, 28, pp. 2633–2636 (1981).

Demailly & Solladie, Tetrahedron Letters, vol. 29, p. 2472 (1975).

*Primary Examiner*—Richard L Raymond
*Attorney, Agent, or Firm*—R. P. Raymond; M-E M. Devlin; A. Stempel

[57] ABSTRACT

The present application relates to the uses of phenylacetic acid benzylamides and new (S)(+)-2-ethoxy-4-[N-[1-2-piperidino-phenyl)-3-methyl-1-butyl]-aminocarbonyl-methyl]-benzoic acid and the salts thereof, which have valuable pharmacological properties, namely an effect on the intermediate metabolism, but particularly the effect of lowering blood sugar.

6 Claims, 12 Drawing Sheets

PHENYLACETIC ACID BENZYLAMIDES

This application is a continuation of application Ser. No. 07/919,820, filed Jul. 24, 1992, now U.S. Pat. No. 5,312,924, which is a continuation-in-part of application Ser. No. 07/495,820, filed Jun. 21, 1990, now U.S. Pat. No. 5,216,167, which is a continuation of application Ser. No. 07/302,022, filed Jan. 25, 1989, now abandoned, which is a continuation-in-part of application Ser. No. 06/878,921, filed Jun. 26, 1986, now abandoned. Said application Ser. No. 07/302,022, now abandoned, is also a continuation-in-part of application Ser. No. 06/872,706, filed Jun. 10, 1986, now abandoned, which is a continuation-in-part of Ser. No. 06/684,054, filed Dec. 20, 1984, now abandoned.

This invention relates to novel phenylacetic acid benzylamides and their non-toxic salts, to methods of preparing these compounds, to pharmaceutical compositions containing them as active ingredients, and to a method of using them as hypoglycemics.

More particularly, the present invention relates to a novel class of compounds represented by the formula

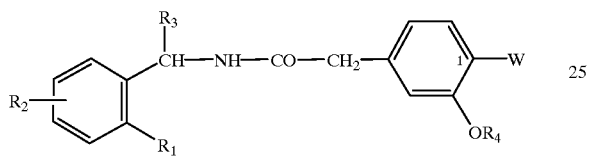

wherein
- $R_1$ represents an unbranched alkyleneimino group with 4 to 6 carbon atoms optionally mono- or di- (alkyl of 1 to 3 carbon atoms)-substituted;
- $R_2$ represents a hydrogen or halogen atom or a methyl or methoxy group;
- $R_3$ represents a hydrogen atom, an alkyl group with 1 to 7 carbon atoms, a phenyl group optionally substituted by a halogen atom or a methyl or methoxy group, an alkyl group with 1 or 2 carbon atoms substituted by a hydroxy, alkoxy, alkanoyloxy, tetrahydrofuranyl, tetrahydropyranyl, cycloalkyl or phenyl group, in which the alkoxy part can contain from 1 to 3 carbon atoms, the alkanoyloxy part can contain 2 or 3 carbon atoms and the cycloalkyl part can contain 3 to 7 carbon atoms, an alkenyl group with 3 to 6 carbon atoms, an alkynyl group with 3 to 5 carbon atoms, a carboxy group or an alkoxycarbonyl group with a total of 2 to 5 carbon atoms;
- $R_4$ represents a hydrogen atom, a methyl, ethyl or allyl group; and
- W represents a methyl, hydroxymethyl, formyl, carboxyl, alkoxycarbonyl, cyanomethyl, 2-cyano-ethyl, 2-cyano-ethenyl, carboxymethyl, 2-carboxyethyl, 2-carboxyethenyl, alkoxycarbonylmethyl, 2-alkoxycarbonyl-ethyl or 2-alkoxycarbonylethenyl group, in which each alkoxy part can contain from 1 to 4 carbon atoms and can be substituted by a phenyl group; and
- when $R_3$ is other then hydrogen and/or the radical $R_1$ contains an optically active carbon atom, the enantiomeres and the diastereomeres thereof or their mixtures; when W is carboxyl, a non-toxic salt thereof formed with an inorganic or organic base; or a non-toxic acid addition salt thereof formed by an inorganic or organic acid with the amino function in the $R_1$-position.

Specific embodiments of substituents $R_1$, $R_2$, $R_3$, $R_4$ and W are the following:
- $R_1$: Pyrrolidino, piperidino, hexamethyleneimino, methyl-pyrrolidino, dimethyl-pyrrolidino, ethyl-pyrrolidino, 2-methyl-piperidino, 3-methyl-piperidino, 4-methyl-piperidino 3,3-dimethyl-piperridino, cis-3,5-dimethyl-piperidino, trans-3,5-dimethyl-piperridino, ethyl-piperidino, diethyl-piperridino, methyl-ethyl-piperridino, propyl-piperridino, nethyl-propyl-piperridino or isoporopyl-piperidino.
- $R_2$: Hydrogen, fluorine, chlorine, bromine, methyl or methoxy.
- $R_3$: Hydrogen, methyl, ethyl, n-propyl, isopropyl, n-butyl, isobutyl, sec.butyl, tert.butyl, n-pentyl, 2-methyl-n-butyl, 3-methyl-n-butyl, 2,2-dimethyl-propyl-n-hexyl, 4-methyl-n-pentyl, n-heptyl, phenyl, fluorophenyl, chlorophenyl, bromo-phenyl, methylphenyl, methoxyphenyl, 1-propen-1-yl, 2-methyl-1-propen-1-yl, 3-methyl-2-buten-2-yl, 2-propen-1-yl, 2-methyl-2-propen-1-yl, 2-buten-1-yl, 2-methyl-2-buten-1-yl, 3-methyl-2-buten-1-yl, 3-buten-1-yl, 2-methyl-3-buten-1-yl, 3-methyl-3-buten-1-yl, 2-hexen-1-yl, 1-propyn-1-yl, 2-propyn-1-yl, 2-butyn-1-yl, 2-pentyn-1-yl, hydroxymethyl, 1-hydroxy-ethyl, 2-hydroxy-ethyl, methoxymethyl, ethoxymethyl, n-propoxymethyl, isopropoxymethyl, 1-methoxy-ethyl, 2-methoxy-ethyl, 1-ethoxy-ethyl, 2-ethoxy-ethyl, 2-n-propoxy-ethyl, 2-isopropoxy-ethyl, acetoxymethyl, propionyloxymethyl, 1-acetoxy-etbyl, 2-acetoxy-ethyl, 1-propionyloxy-ethyl, 2-propiomyloxy ethyl, tetrahydrofuran-2-yl-methyl, 2-(tetrahydrofran-2-yl)-ethyl, tetrahydrofuran-3-yl-methyl, tetrahydropyran-2-yl-methyl, 2-(tetrahydropyran-2-yl)-ethyl, tetrahydropyran-3-yl-methyl, cyclopropylmethyl, cyclobutylmethyl, cyclopentylmethyl, cyclohexylmethyl, cycloheptylmethyl, 2-cyclopropyl-ethyl, 2-cyclobutyl-ethyl, 2-cyclopentyl-ethyl, 2-cyclohexyl-ethyl, 2-cycloheptyl-ethyl, benzyl, 1-phenyl-ethyl, 2-phenyl-ethyl, carboxy, methoxycarbonyl, ethoxycarbonyl, n-propoxycarbonyl, isopropoxycarbonyl, n-butoxycarbonyl, sec.butoxycarbonyl, isobutoxycarbonyl or tert.butoxycarbonyl.
- $R_4$: Hydrogen, methyl, ethyl, n-propyl, isopropyl, allyl.
- W: Methyl, hydroxymethyl, formyl, carboxy, methoxycarbonyl, ethoxycarbonyl, n-propoxycarbonyl, isopropoxycarbonyl, n-butoxycarbonyl, sec.butoxycarbonyl, isobutoxycarbonyl, tert.butoxycarbonyl, benzyloxycarbonyl, 1-phenylethoxycarbonyl, 2-phenylethoxycarbonyl, 3-phenylpropoxycarbonyl, cyanomethyl, 2-cyano-ethyl, 2-cyano-ethenyl, carboxymethyl, methoxycarbonylmethyl, ethoxycarbonylmethyl, n-propoxycarbonylmethyl, n-butoxycarbonylmethyl, tert.butoxycarbonylmethyl, 2-methoxycarbonyl-ethyl, 2-ethoxycarbonyl-ethyl, 2-n-propoxycarbonyl-ethyl, 2-isopropoxycarbonyl-ethyl, 2-n-butoxycarbonyl-ethyl, 2-tert.butoxycarbonyl-ethyl, 2-methoxycarbonyl-ethenyl, 2-ethoxycarbonyl-ethenyl, 2-n-propoxycarbonyl-ethenyl or 2-tert.butoxycarbonylethenyl.

One subgeneric aspect is constituted by those compounds of the formula I wherein
- $R_1$ represents a pyrrolidino, piperidino, 4-methyl-piperidino, 3-methyl-piperidino, 3,3-dimethyl-piperidino, 3,5-dimethyl-piperidino or hexamethylene-imino group;

$R_2$ represents a hydrogen, fluorine or chlorine atom;

$R_3$ represents hydrogen atom, an alkyl group with 1 to 6 carbon atoms, a phenyl, methyl-phenyl, chloro-phenyl, methoxy-phenyl, cyclopropylmethyl, cyclobutylmethyl, cyclopentylmethyl, cyclohexylmethyl, tetrahydrofuran-2-yl-methyl, tetrahydropyran-2-yl-methyl, propargyl, hydroxymethyl, ethoxymethyl, acetoxymethyl, propionyloxymethyl, carboxy, methoxycarbonyl, ethoxycarbonyl or propoxycarbonyl group or a branched or unbranched alkenyl group with 3 or 4 carbon atoms;

$R_4$ represents a methyl, ethyl or allyl group; and

W represents a methyl, hydroxymethyl, formyl, carboxyl, benzyloxycarbonyl, carboxymethyl, methoxycarbonylmethyl, ethoxycarbonylmethyl, cyanomethyl, 2-carboxy-ethyl, 2-ethoxycarbonyl-ethyl, 2-cyano-ethyl, 2-carboxy-ethenyl, 2-ethoxycarbonyl-ethenyl or 2-cyano-ethenyl group or an alkoxycarbonyl group with 1 to 4 carbon atoms in the alkoxy part; and when $R_3$ is other then hydrogen and/or $R_1$ represents the 3-methyl-piperidino group, the enantiomeres and the diastereomeres thereof or their mixtures; when W is carboxyl, a non-toxic salt thereof formed with an inorganic or organic base; or a non-toxic acid addition salt thereof formed by an inorganic or organic acid with the amino function in the $R_1$-position.

A preferred sugenus is constituted by those compounds of the formula I wherein $R_1$ represents a piperidino group;

$R_2$ represents a hydrogen atom;

$R_3$ represents an alkyl group with 1 to 6 carbon atoms, an alkenyl group with 3 or 4 carbon atoms, a phenyl, tetrahydropyran-2-yl-methyl, cyclopropylmethyl or cyclohexylmethyl group;

$R_4$ represents a rnethyl, ethyl or allyl group; and

W represents a carboxyl, methoxycarbonyl, ethoxycarbonyl or cyanomethyl group; and the enantiomeres thereof or their mixtures; when W is carboxyl, a non-toxic salt thereof formed with an inorganic or organic base; or a non-toxic acid addition salt thereof formed by an inorganic or organic acid with the piperidino function.

An especially preferred subgenus is constituted by those compounds of the formula I wherein $R_1$ represents a piperidino group;

$R_2$ represents a hydrogen atom;

$R_3$ represents an alkyl group with 3 to 6 carbon atoms, an alkenyl group with 3 or 4 carbon atoms, a phenyl, cyclopropylmethyl or cyclohexylmethyl group;

$R_4$ represents a methyl or ethyl group; and

W represents a carboxyl group;

especially those compounds of the before mentioned preferred subgenus, wherein $R_3$ represents an alkyl group with 3 to 6 carbon atoms, a 2-methyl-1-propen-1-yl, cyclomethylpropyl or cyclohexylmethyl group; and the enantiomeres thereof or their mixtures; when W is carboxyl, a non-toxic salt thereof formed with an inorganic or organic base; or a non-toxic acid addition salt thereof formed by an inorganic or organic acid with the piperidino function.

A preferred subgenus of the before mentioned compounds are those, wherein $R_3$ represents a n-propyl, n-butyl, isobutyl, sec.butyl, n-pentyl, 2-methyl-1-propen-1-yl, cyclomethylpropyl or cyclohexylmethyl group, especially when $R_3$ represents a n-propyl, n-butyl, isobutyl, sec.butyl or n-pentyl group; and the enantiomeres thereof or their mixtures; when W is carboxyl, a non-toxic salt thereof formed with an inorganic or organic base; or a non-toxic acid addition salt thereof formed by an inorganic or organic acid with the piperidino function.

According to the invention, the new compounds are obtained by the following methods:

a) reacting an aminie of formula

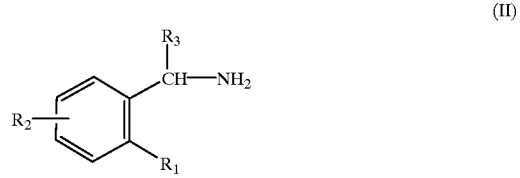

(II)

wherein $R_1$ to $R_3$ are defined as hereinbefore, with a carboxylic acid of formula

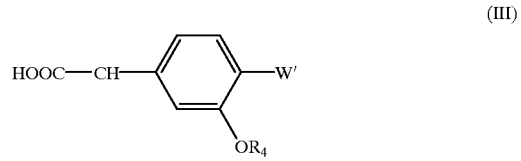

(III)

wherein $R_4$ is defined as hereinbefore and

W' has the meanings given for W hereinbefore, in which any carboxy group contained in the group W can be protected by a protecting group, or with the reactive derivatives thereof optionally prepared in the reaction mixture, if necessasy with subsequent splitting off of any protecting group used.

Examples of reactive derivatives of a compound of formula III which can be used include esters thereof, such as the methyl, ethyl or benzyl esters, the thioesters such as the methylthio or ethylthioesters, the halides such as the acid chloride, the anhydrides or imidazolides thereof.

The reaction is appropriately carried out in a solvent such as methylene chloride, chloroform, carbon tetrachloride, ether, tetrahydrofuran, dioxan, benzene, toluene, acetonitrile or dimethyl formamide, optionally in the presence of an acid-activating agent or a dehydrating agent,e.g.in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, or an agent which activates the amino group, e.g. phosphorus trichloride, and optionally in the presence of an inorganic base such as sodium carbonate or a tertiary organic base such as triethylamine or pyridine, which can simultaneously be used as solvent, at temperatures of between –25° C. and 250° C., but preferably at temperatures of between –10° C. and the boiling temperature of the solvent used. The reaction can also be carried out without a solvent and furthermore any water formed during the reaction can be removed by azeotropic distillation, e.g. by heating with toluene using a water separator, or by adding a drying agent such as magnesium sulphate or a molecular sieve.

If necessary, the subsequent splitting off of a protecting group is preferably carried out by hydrolysis, conveniently either in the presence of an acid such as hydrochloric, sulphuric, phosphoric or trichloroacetic acid or in the presence of a base such as sodium hydroxide or potassium hydroxide in a suitable solvent such as water, methanol, methanol/water, ethanol, ethanol/water, water/isopropanol or water/dioxan at temperatures of between −10 and 120° C., e.g. at temperatures of between ambient temperature and the boiling temperature of the reaction mixture.

A tert.butyl group used as protecting group can also be split off thermally, optionally in an inert solvent such as methylene chloride, chloroform, benzene, toluene, tetrahydrofuran or dioxan and preferably in the presence of a catalytic quantity of an acid such as p-toluenesulphonic acid, sulphuric, phosphoric or polyphosphoric acid.

Furthermore, a benzyl group used as protecting group can also be split off hydrogenolytically in the presence of a hydrogenation catalyst such as palladium/charcoal in a suitable solvent such as methanol, ethanol, ethanol/water, glacial acetic acid, ethyl acetate, dioxan or dimethylformamide.

b) In order to prepare compounds of formula I wherein $R_3$ represents a carboxy or alkoxycarbonyl group and W has the meanings given hereinbefore or W represents a carboxy, carboxymethyl, 2-carboxy-ethyl, 2-carboxy-ethenyl, alkoxycarbonyl, alkoxycarbonylmethyl, 2-alkoxycarbonyl-ethyl or 2-2-alkoxycarbonyl-ethenyl group and $R_3$ has the meanings given hereinbefore:

Hydrolysis, thermolysis, hydrogenolysis or alcoholysis or a compound of formula

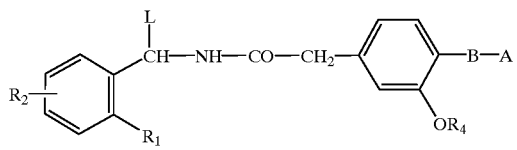

wherein $R_1$, $R_2$ and $R_4$ are as hereinbefore defined,

B represents a bond, a methylene, ethylene or ethenylene group,

A and L each represent a nitrile group or a group which can be converted into a carboxy group by hydrolysis, thermolysis or hydrogenolysis and L additionally has the meanings given for $R_3$ hereinbefore.

Examples of hydrolysable groups include functional derivatives of the carboxy group and the unsubstituted or substituted amides, esters, thioesters, ortho esters, iminoethers, amidines or anhydrides thereof, the nitrile group, the tetrazolyl group, an optionally substituted 1,3-oxazol-2-yl or 1,3-oxazolin-2-yl group, examples of thermolytically cleavable groups include esters with tertiary alcohols, e.g. the tert.butyl ester, examples of hydrogenolytically cleavable groups include aralykyl groups, e.g. the benzyl group, and examples of alcoholytically cleavable groups include the cyano group.

The hydrolysis is conveniently carried out either in the presence of an acid such as hydrochloric, sulphuric, phosphoric or trichloroacetic acid or in the presence of a base such as sodium hydroxide or potassium hydroxide in a suitable solvent such as water, water/methanol, ethanol, water/ethanol,water/isopropanol orwater/dioxan at temperatures of between −10 and 120° C., e.g. at temperatures of between ambient temperature and the boiling temperature of the reaction mixture, and the alcoholysis of a cyano group is preferably effected in an excess of the corresponding alcohol such as methanol, ethanol or propanol and in the presence of an acid such as hydrochloric acid at elevated temperature, e.g. at the boiling temperature of the reaction mixture.

I A and/or L in a compound of formula IV represents a nitrile or aminocarbonyl group, these groups can be converted into a corresponding carboxy compound by means of 100% phosphoric acid at temperatures of between 100 and 180° C., preferably at temperatures of between 120 and 160° C., or with a nitrite, e.g. sodium nitrite, in the presence of an acid such as sulphuric acid, the latter conveniently being used as solvent as well, at temperatures of between 0 and 50° C.

If A and/or L in a compound of formula IV represents the tertburyloxycarbonyl group for example, the tert.butyl group can also be split off thermally, optionally in an inert solvent such as methylene chloride, chloroform, benzene, toluene, tetrahydrofuran or dioxan and preferably in the presence of a catalytic quantity of an acid such as p-toluenesulphonic, sulphuric, phosphoric or polyphosphoric acid, preferably at the boiling temperature of the solvent used, e.g. at temperatures of between 40 and 100° C.

If A and/or L in a compound of formula IV represents the benzyloxycarbonyl group for example, the benzyl group can also be split off hydrogenolytically in the presence of a hydrogenation catalyst such as palladium/charcoal in a suitable solvent such as methanol, ethanol, methanol/water, ethanol/water, glacial acetic acid, ethyl acetate, dioxan or dimethylformamide, preferably at temperatures of between 0 and 50° C., e.g. at ambient temperature and under a hydrogen pressure of from 1 to 5 bar. During hydrogenolysis, a compound containing halogen can simultaneously be dehalogenated, any double or triple bonds present can be hydrogenated and any benzyloxycarbonyl group present can be converted into a carboxy group.

c) In order to prepare compounds of formula I wherein $R_4$ represents a hydrogen atom:

Splitting off a protecting group from a compound of formula

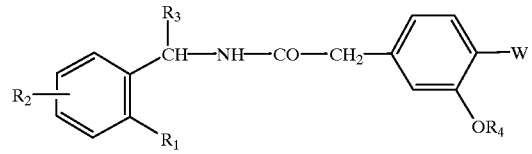

wherein $R_1$ to $R_3$ and W are as hereinbefore defined and $R_5$ represents a protecting group for a hydroxy group.

Examples of protecting groups for $R_5$ include, for example, an alkyl, aralkyl or trialkylsilyl group, e.g. the methyl, ethyl, propyl, allyl, benzyl or trimethylsilyl group.

Depending on the protecting group used, the protecting groups mentioned above can be split off either by hydrolysis or by hydrogenolysis, optionally in a suitable solvent, at temperatures of between −78 and 250° C.

For example, ether splitting is carried out in the presence of an acid such as hydrochloric, hydrobromic or sulphuric acid, boron tribromide, aluminium trichloride or pyridine hydrochloride, conveniently in a suitable solvent such as methylene chloride, glacial acetic acid or water or in mixtures thereof at temperatures of between −78 and 250° C. The ether splitting is carried out in the presence of a proton acid conveniently at temperatures of between 0 and 150° C., preferably at temperatures of between 50 and 150° C. or with a Lewis acid preferably in a solvent such as methylene chloride at temperatures of between For example, any protecting group used such as a benzyl group can be split off hydrogenolytically with hydrogen in the presence of a hydrogenation catalyst such as palladium/charcoal in a suitable solvent such as methanol, ethanol, ethanol/water, glacial acetic acid, ethyl acetate, dioxan or dimethylformamide, preferably at ambient temperature, for example, and under a hydrogen pressure of from 1 to 5 bar.

d) In order to prepare compounds of formula I wherein $R_4$ represents methyl, ethyl or allyl group:

Reacting a compound of formula

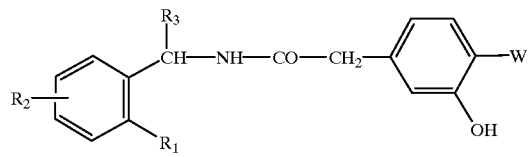

wherein $R_1$ to $R_3$ and W are as hereinbefore defined, with a compound of formula

 X—$R_6$ (VII)

wherein $R_6$ represents methyl, ethyl or allyl group

X represents a nucleophilically exchangeable group such as a halogen atom, a sulphonyloxy group or, together with the adjacent hydrogen atom, a diazo group if $R_6$ represents an alkyl group with 1 to 3 carbon atoms, if necessary with subsequent hydrolysis.

The reaction is conveniently carried out with a corresponding halide, sulphonic acid ester, sulphuric acid diester or diazoalkane, e.g. with methyl iodide, dimethyl sulphate, ethyl bromide, diethyl sulphate, allyl bromide, ethyl p-toluenesulphonate, or diazomethane, optionally in the presence of a base such as sodium hydride, potassium carbonate, sodium hydroxide, potassium tert.butoxide or triethylamine in a suitable solvent such as acetone, diethylether, tetrahydrofuran, dioxan or dimethylformamide at temperatures of between 0 and 100° C., preferably at temperatures of between 20 and 50° C.

If in a compound of formula VI $R_3$ represents a carboxy group and/or W represents a carboxy, carboxymethyl, 2-carboxy-thyl or 2-carboxy-ethenyl group, this compound can simultaneously be converted into the corresponding ester compound. A compound thus obtained is, if necessary by cleaving the ester group, converted into the desired compound of formula I.

The cleaving of the ester group is carried out hydrolytically, conveniently either in the presence of an acid such as hydrochloric, sulphuric, phosphoric or trichloroacetic acid or in the presence of a base such as sodium hydroxide or potassium hydroxide in a suitable solvent such as water, methanol, methanol/water, ethanol, ethanol/water, water/isopropanol or water/dioxan at temperatures of between −10 and 120° C., e.g. at temperatures of between ambient temperature and the boiling point of the reaction mixture.

e) In order to prepare compounds of formula I wherein W represents a cyanomethyl or 2-cyano-ethyl group:

Reacting a compound of formula

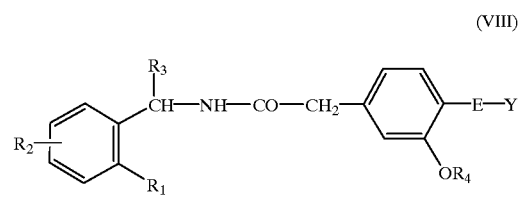

wherein $R_1$ to $R_4$ are as hereinbefore defined,

E represents a methylene or ethylene group and

Y represents a nucleophilically exchangeable group such as a halogen atom or a sulphonyloxy group, e.g. a chlorine, bromine or iodine atom or a methane-sulphonyloxy or p-toluenesulphonyloxy group, with an alkali metal cyanide such as sodium or potassium cyanide.

The reaction is conveniently carried out in a suitable solvent such as dimethylsulphoxide or dimethylformamide at temperatures of between 0 and 100° C., preferably at temperatures of between 20 and 50° C., or in a two-phase system such as methylene chloride/water in the presence of a phase transfer catalyst such as benzyl-tributyl-ammonium chloride at temperatures of between 0 and 100° C., preferably at temperatures of between 20 and 50° C.

f) In order to prepare compounds of formula I wherein W represents a cyanomethyl, 2-cyano-ethyl or 2yano-ethenyl group:

Dehydration of a compound of formula

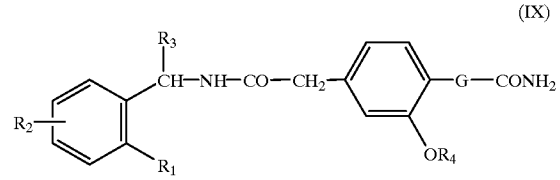

wherein $R_1$ to $R_4$ are as hereinbefore defined and

G represents a methylene, ethylene or ethenylene group.

The dehydration is carried out with a water-cleaving agent such as phosphorus pentoxide, phosphorus oxychloride, triphenylphosphine/carbon tetrachloride or p-toluenesulphonic acid chloride, optionally in a solvent such as methylene chloride, acetonitrile or pyridine at temperatures of between 0 and 100° C., preferably at temperatures of between 20° C. and 80° C.

g) In order to prepare compounds of formula I wherein W represents a 2-cyano-ethenyl, 2-carboxy-ethenyl or 2-alkoxycarbonyl-ethenyl group:

Reacting a compound of formula

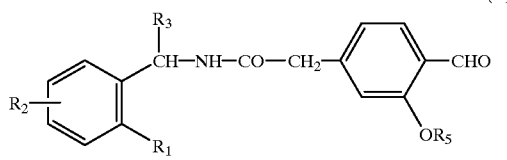

wherein
$R_1$ to $R_4$ are as hereinbefore defined, with a corresponding acetic acid derivative of formula

$$Z-CH_2-Q \quad (XI)$$

wherein Q represents a carboxy, alkoxycarbonyl or cyano group and
Z represents a hydrogen atom, an alkoxycarbonyl, dialkylphosphono or triphenylphosphonium halide group, optionally with subsequent hydrolysis and/or decarboxylation.

The reaction is conveniently carried out in a solvent such as diethylether, tetrahydrofuran, 1,2-dimethoxyethane, dioxan, dimethylformamide, toluene or pyridine in the presence of a base as condensation agent such as sodium carbonate, sodium hydride, potassium tert.butoxide or piperidine at temperatures of between 0 and 100° C., preferably at temperatures of between 20 and 80° C.

The subsequent hydrolysis and/or decarboxylation is conveniently carried out either in the presence of an acid such as hydrochloric, sulphuric, phosphoric or trichloroacetic acid or in the presence of a base such as sodium hydroxide or potassium hydroxide in a suitable solvent such as water, water/methanol, ethanol, water/ethanol, water/isopropanol or water/dioxan at temperatures of between −10° C. and 120° C., e.g. at temperatures of between ambient temperature and the boiling temperature of the reaction mixture.

h) In order to prepare compounds of formula I wherein W represents a 2-carboxy-ethyl, 2-alkoxy-carbonyl-ethyl or 2-cyano-ethyl group:
Reduction of a compound of formula

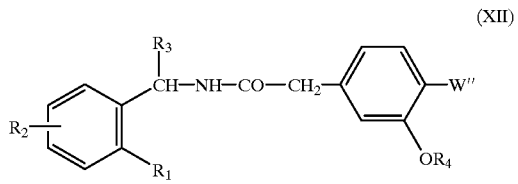

wherein
$R_1$ to $R_4$ are as hereinbefore defined a
W″ represents a 2-carboxy-ethenyl, 2-alkoxycarbonyl-ethenyl or 2-cyano-ethenyl group.

The reduction is preferably carried out in a suitable solvent such as methanol, ethanol, isopropanol, ethyl acetate, dioxan, tetrahydrofuran, dimethylformamide, benzene or benzene/ethanol with hydrogen in the presence of a suitable hydrogenation catalyst such as palladium/charcoal, Raney nickel or tris-[triphenylphosphine-rhodium(I) chloride at temperatures of between 0 and 100° C., but preferably at temperatures of between 20° C. and 50° C., under a hydrogen pressure of from 1 to 5 bar or, if W″ contains a cyano group, with nascent hydrogen, e.g. with magnesium/methanol, or with a copper hydride complex, e.g. with the complex prepared from copper bromide, sodium bis(2-methoxyethoxy)-aluminium hydride and sec.butanol, at temperatures of between −78 and 50° C. Other groups can be reduced at the same time, e.g. a benzyloxy group can be reduced to the hydroxy group, an alkenyl or alkynyl group can be reduced to the corresponding alkyl group or a formyl group can be reduced to the hydroxymethyl group, or they can be replaced by hydrogen atoms, e.g. a halogen atom can be replaced by a hydrogen atom.

i) In order to prepare compound of formula I wherein $R_3$ represents an alkyl group with 1 or 2 carbon atoms substituted by an alkoxy or alkanoyloxy group:
Reacting a compound of formula

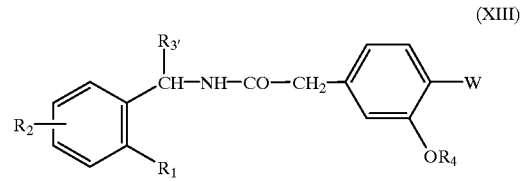

wherein
$R_1$, $R_2$, $R_4$ and W are as hereinbefore defined and $R_3$ represents an alkyl group with 1 or 2 carbon atoms substituted by a hydroxy group, with a compound of formula

$$U-R_7 \quad (XIV)$$

wherein
$R_7$ represents an alkyl group with 1 to 3 carbon atoms or an acetyl or propionyl group and U represents a nucleophilically exchangeable group such as a halogen atom, a sulphonyloxy group, an acetoxy or propionyloxy group or, together with the adjacent hydrogen atom, represents a diazo group if $R_7$ represents an alkyl group with 1 to 3 carbon atoms, optionally with subsequent hydrolysis.

The reaction is conveniently carried out with a corresponding halide, anhydride, sulphonic acid ester, sulphuric acid diester or diazoalkane, e.g. with methyl iodide, dimethyl sulphate, ethyl iodide, diethyl sulphate, n-propyl iodide, isopropyl bromide, acetyl chloride, acetic hydride, propionic acid chloride, propionic acid anhydride, ethyl p-toluenesulphonate or isopropylmethanesulphonate, optionally in the presence of a base such as sodium hydride, potassium carbonate, sodium hydroxide, potassium tert.butoxide or triethylamine, or with diazomethane, optionally in the presence of a Lewis acid, e.g. boron trifluoride, preferably in a suitable solvent such as acetone, diethylether, tetrahydrofuran, dioxan, pyridine or dimethylformamide at temperatures of between 0 and 100° C., preferably at temperatures of between 20 and 50° C., in which an anhydride used as the acylating agent can simultaneoudly also be used as solvent.

If in a compound of formula XIII W represents a carboxy, carboxymethyl, 2-carboxy-ethyl or 2-carboxy-ethenyl group and/or $R_4$ represents a hydrogen atom, this can simultaneously be converted into the corresponding ester and/or ether compound.

k) In order to prepare compounds of formula I wherein $R_3$ represents an alkoxycarbonyl group:

Reacting a compound of formula

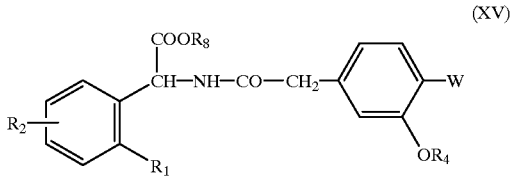

(XV)

wherein
$R_1$, $R_2$, $R_4$ and W are as hereinbefore defined and
$R_3$ represents a hydrogen atom or alkali metal atom, or the reactive derivatives thereof optionally prepared in the reaction mixture, with a compound of formula

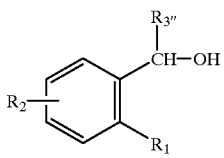

wherein
$R_9$ represents an alkyl group with 1 to 4 carbon atoms and
T represents a hydroxy group or a nucleophilically exchangeable group such as a halogen atom or a sulphonyloxy group, or together with the adjacent hydrogen atom of the group $R_9$ represents a diazo group, optionally followed by hydrogenolysis if W contains a benzyloxycarbonyl group.

An example of a reactive derivative of a compound of formula XV is the imidazolide thereof.

The reaction is conveniently carried out in the corresponding alcohol as solvent or in a suitable solvent such as methylene chloride, chloroform, ether, tetrahydrofuran, dioxan, dimethylformamide, benzene or toluene, optionally in the presence of an acid-activating agent or a dehydrating agent, e.g. in the presence of hydrogen chloride, sulphuric acid, ethyl chloroformate, thionylchloride, carbon tetrachloride/triphenylphosphine, carbonyldiimidazole or N,N'-dicyclohexylcarbodiimide or the isourea ethers thereof, optionally in the presence of a reaction accelerator such as copper chloride and optionally in the presence of an inorganic base such as potassium carbonate or a tertiary organic base such as triethylamine, 1,8-diazabicyclo[5,4,0]-undec-7-ene or pyridine, or by transesterification, e.g. with a corresponding carbonic acid diester, at temperatures of between –10° C. and 100° C., but preferably at temperatures of between –10° C. and the boiling temperature of the solvent used.

The optional subsequent hydrogenolysis is carried out in the presence of a hydrogenation catalyst such as palladium/charcoal in a suitable solvent such as methanol, ethanol, ethano/water, glacial acetic acid, ethyl acetate, dioxan or dimethylformamide.

If W in a compound of formula XV contains a carboxy group, this can be converted during the reaction into the corresponding alkoxycarbonyl group.

1) In order to prepare compounds of formula I where
$R_4$ represents a hydrogen atom, methyl, ethyl or allyl group and
W represents a methyl, formyl, carboxy, carboxymethyl, 2-carboxy-ethyl, alkoxycarbonyl, alkoxycarbonylmethyl or 2-alkoxycarbonylethyl group, in which the alkoxy part can contain from 1 to 4 carbon atoms.

Reacting a compound of formula (XVII)

wherein
$R_1$ and $R_2$ are as hereinbefore defined and
$R_3''$ represents a hydrogen atom, an alkyl group with 1 to 7 carbon atoms, a phenyl group optionally substituted by a halogen atom or by a methyl or methoxy group, an alkyl group with 1 or 2 carbon atoms substituted by an alkoxy, alkanoyloxy, tetrahydrofuranyl, tetrahydropyranyl, cycloalkyl or phenyl group, wherein the alkoxy part can contain 1 to 3 carbon atoms, the alkanoyloxy part can contain 2 or 3 carbon atoms and the cycloalkyl part can contain 3 to 7 carbon atoms, an alkenyl group with 3 to 6 carbon atoms, an alkynyl group with 3 to 5 carbon atoms, a carboxy group or an alkoxycarbonyl group with a total of 2 to 5 carbon atoms, with a compound of formula

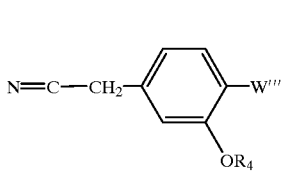

(XVIII)

wherein
$R_4$ is as hereinbefore defined and
$W'''$ represents a methyl, formyl, carboxy, carboxymethyl, 2-carboxy-ethyl, alkoxycarbonyl, alkoxy-carbonylmethyl or 2-alkoxy-carbonyl-ethyl group, in which each alkoxy part can contain from 1 to 4 carbon atoms.

The reaction is carried out in the presence of a strong acid which can simultaneously serve as solvent, preferably in concentrated sulfuric acid, at temperatures of between 0 and 150° C., preferably at temperatures of between 20 and 100° C.

If in a compound of formula XVIII $R_4$ represents an allyl group, this is split off during the reaction or after the reaction by the addition of water.

m) In order to prepare compound of formula I wherein
$R_4$ represents a hydrogen atom, a methyl or ethyl group,
$R_3$ represents an alkyl group with 1 to 7 carbon atoms, a phenyl group optionally substituted by a methyl or methoxy group, an alkyl group with 1 or 2 carbon atoms substituted by an alkoxy, tetrahydrofuranyl, tetrahydropyranyl, cycloalkyl or phenyl group in which the alkoxy part can contain 1 to 3 carbon atoms and the cycloalkyl part can contain 5 to 7 carbon atoms, and
W represents a methyl, hydroxynethyl, carboxy, cyanomethyl, 2-cyano-ethyl, carboxymethyl, 2-carboxy-ethyl, alkoxycarbonyl, alkoxycarbonyl-methyl or 2-alkoxycarbonyl-ethyl group in which the alkoxy part can contain from 1 to 4 carbon atoms.

Reduction of a compound of formula

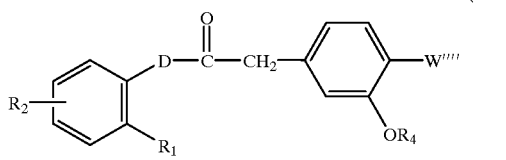

(XIX)

wherein

R$_1$, R$_2$ and R$_4$ are as hereinbefore defined and
D represents a group of formula

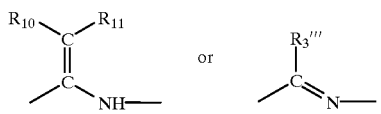

in which R$_3$''' represents a phenyl group optionally substituted by a halogen atom or by a methyl or methoxy group, R$_{10}$ and R$_{11}$ together with the carbon atom between them represent an alkylidene group with 1 to 7 carbon atoms, an alkylidene group with 1 or 2 carbon atoms substituted by an alkoxy, tetrahydrofuranyl, tetrahydropyranyl, cycloalkyl or phenyl group, in which the alkoxy part can contain 1 to 3 carbon atoms and the cycloalkyl part can contain 5 to 7 carbon atoms, and W"" represents a methyl, hydroxymethyl, formyl, carboxy, cyanomethyl, 2-cyano-ethyl, 2-cyano-ethyl, carboxymethyl, 2-carboxy-ethyl, 2-carboxy-ethenyl, alkoxycarbonyl, alkoxycarbonylmethyl, 2-alkoxycarbonyl-ethyl or 2-alkoxycarbonyl-ethenyl group, in which the alkoxy part can contain from 1 to 4 carbon atoms and can be substituted by a phenyl group.

The reduction is preferably carried out with hydrogen in the presence of a hydrogenation catalyst such as palladium/charcoal or Raney-nickel in a suitable solvent such as methanol, ethanol, isopropanol, ethyl acetate, dioxan, tetrahydrofuran, dimethylformamide, benzene or benzene/ethanol at temperatures of between 0 and 100° C., preferably at temperatures of between 20 and 50° C., and under a hydrogen pressure of from 1 to 5 bar. When a suitable chiral hydrogenation catalyst is used, such as a metal ligand complex e.g. [(2S), (4S)-1-tert.butoxycarbonyl-4-diphenylphosphino-2-diphenylphosphinomethyl-pyrrolidine-rhodium-cyclooctadiene(1,5)]-perchlorate, the addition of hydrogen occurs enantioselectively. Moreover, in the catalytic hydrogenation, other groups can also be reduced, e.g. a benzyloxy group can be reduced to the hydroxy group or a formyl group can be reduced to the hydroxy methyl group, or they can be replaced by hydrogen atoms, e.g. a halogen atom can be replaced by a hydrogen atom.

If a compound of the formula I is obtained wherein R$_2$ is halogen and/or R$_3$ is halophenyl and/or W is hydroxymethyl which has been converted into halomethyl, it may, if desired, be converted by de-halogenation into a corresponding compound of the formula I wherein R$_2$ is hydrogen and/or R$_3$ is phenyl and/or W is methyl.

If a compound of the formula I is obtained wherein W is carboxyl, this compound may, if desired, be converted by esterification into a corresponding compound of the formula I wherein W is alkoxycarbonyl or phenylalkoxycarbonyl.

If a compound of the formula I is obtained wherein W is carboxyl, alkoxycarbonyl or phenylalkoxycarbonyl, this compound may be converted by reduction into a corresponding compound of the formula I wherein W is formyl or hydroxymethyl.

If a compound of the formula I is obtained wherein W is hydroxymethyl, this compound may be converted by oxidation into a corresponding compound of the formula I wherein W is formyl or carboxyl.

If a compound of the formula I is obtained wherein W is carboxyl, this compound may be converted, via a sulfonic acid hydrazide and subsequent disproportionation, into a corresponding compound of the formula I wherein W is formyl.

The subsequent dehalogenation is advantageously carried out by catalytic hydrogenation, for example with palladium-on-charcoal, in a suitable solvent such as methanol, ethanol, tetrahydrofuran, dioxane, dinmethylformamide or ethyl acetate, optionally in the presence of a base such as triethylamine, an at temperatures between 20° and 100° C., preferably at 20° to 50° C.

The subsequent esterification is advantageously carried out in a suitable solvent, for instance in a corresponding alcohol, pyridine, toluene, nethylene chloride, tetrahydrofuran or dioxane, in the presence of an acid-activating and/or dehydrating agent such as thionyl chloride, ethyl chloro or,mate carbonyldiimidazole or N,N'-dicyclohexylcarbodiimide or the isourea ethers thereof, optionally in the presence of a reaction accelerator such as copper chloride, or by trans-esterification, for instance with a corresponding carbonic acid diester, at temperatures between 0° and 100° C., but preferably at temprature between 20° and the boiling point of the solvent which is used.

The subsequent reduction is preferably carried out with a metal hydride, for example with a complex metal hydride such as lithium aluminum hydride, lithium borohydride or lithium borohydride/trimethylborater in a suitable solvent such as diethyl ether, tetrahydrofuran, dioxane or 1,2-dimethoxyethane at temperatures between 0° and 100° C., but preferably at temperatures between 20° C. and 60° C.

The subsequent oxidation of an alcohol is preferably carried out with an oxidizing agent, for instance with pyridinium chlorochromate or manganese dioxide, in a suitable solvent such as chloroform or methylene chloride at temperatures between –10° and 50° C., but preferably at temperatures between 0° and 20° C.

The subsequent disproportionation of a sulfonic acid hydrazide, obtained by reacting a corresponding hydrazine with a suitable reactive carboxylic acid derivative, is carried out in the presence of a base such as sodium carbonate in a solve such as ethylene glycol at temperatures between 100° C. and 200° C., but preferably at 160–170° C.

If according to the invention a racemic compound of formula I is obtained wherein R$_3$ has the meaning given hereinbefore with the exception of the hydrogen atom, this compound can be resolved into the enantiomers thereof via the diastereomeric adducts, complexes, salts or derivatives thereof.

The subsequent racemate splitting is preferably carried out by column or HPL chromatography by forming diastereomeric adducts or complexes in a chiral phase.

The compounds of formula I obtained according to the invention can also be converted into the salts thereof and, for pharmaceutical use, into the nontoxic, pharmaceutically acceptable salts thereof with inorganic or organic acids or bases. Suitable acids include, for example, hydrochloric, hydrobromic, sulfuric, phosphoric, lactic, citric, tartaric, succinic, maleic, fumaric, aspartic or glutamic acid and suitable bases include sodium hydroxide, potassium hydroxide, calcium hydroxide, cyclohexylamine, ethanolamine, diethanolamine, triethanolamine, ethylenediamine, lysine or arginine.

The compounds of formulae II to XIX used as starting materials are known from the literature in some cases or can be obtained by methods known per se.

Thus, for example, a compound of formula II is obtained by reducing a corresponding nitrile with lithium aluminum hydride or with catalytically activated hydrogen, by reacting a corresponding nitrile with a corresponding grignard or lithium compound and subsequent lithium-aluminum hydride reduction or subsequent hydrolysis to form the ketimine which is subsequently reduced with catalytically activated hydrogen, with a complex metal hydride or with nascent hydrogen, by hydrolysis or by hydrazinolysis of a corresponding phthalimido compound, by reacting a corresponding ketone with ammonium formate and subsequent hydrolysis or with an ammonium salt in the presence of sodium cyanoborohydride, by reduction of a corresponding oxime with lithium aluminum hydride, with catalitically activated or nascent hydrogen, by reduction of a corresponding N-benzyl or N-1-phenylethyl Schiff's base e.g. with a complex metal hydride in ether or tetrahydrofuran at temperatures of between −78° C. and the boiling temperature of the solvent used with subsequent splitting off of the benzyl or 1-phenylethyl group by catalytic hydrogenation, by lithiation of a corresponding benzylideneimino-benzyl compound, e.g. by means of lithium-diisopropylamide at temperatures of between −78 and 20° C., subsequent reaction with a corresponding halogen compound, e.g. with a corresponding bromoalkyl, bromoalkenyl or bromoalkinyl compound, and subsequent hydrolysis, by Ritter reaction of a corresponding alcohol with potassium cyanide in sulfuric acid, by Hofmann, Curtius, Lossen or Schmidt degradation of a corresponding compound or by converting a corresponding benzaldehyde into a corresponding glycine derivative, e.g. using sodium cyanide/ammonium carbonate in ethanol/water into a corresponding hydantoin derivative, hydrolysis thereof, and, if necessary, subsequent esterification and, if necessary, subsequent reduction, e.g. with a complex metal hydride in ether or tetrahydrofuran.

An amine of formula II thus obtained having a chiral center can be resolved into its enantiomers by racemate splitting, e.g. by fractional crystallization of the diastereomeric salts with optically active acids and subsequent decomposition of the salts or by column or HPL chromatography, optionally in the form of the acyl derivative thereof, or by forming diastereomeric compounds, separating them and subsequently splitting them.

Moreover, an optically active amine of formula II can also be prepared by enantioselective reduction of a corresponding ketimine using complex boron or aluminum hydrides in which some of the hydride hydrogen atoms have been replaced by optically active alkoxide groups, or by means of hydrogen in the presence of a suitable chiral hydrogenation catalyst or analogously starting from a corresponding N-benzyl or N-(1-phenethyl)-ketimine or from a corresponding N-acyl-ketimine or enimide and optionally subsequently splitting off the benzyl, 1-phenethyl or acyl group.

Furthermore, an optically active amine of formula II can also be prepared by diastereoselective reduction of a corresponding ketimine or hydrazone substituted at the nitrogen atom with a chiral group, using a complex or non-complex boron or aluminum hydride in which some of the hydride hydrogens can optionally be replaced by corresponding alkoxide, phenoxide or alkyl groups or using hydrogen in the presence of a suitable hydrogenation catalyst optionally with subsequent splitting off of the chiral auxiliary group by catalytic hydrogenolysis or hydrolysis.

Moreover, an optically active amine of formula II can also be prepared by diastereo-selective addition of a corresponding organometallic compound, preferably a grignard or lithium compound, to a corresponding aldimine substituted with a chiral group at the nitrogen atom, by subsequent hydrolysis and optionally subsequent splitting off of the chiral auxiliary group by catalytic hydrogenolysis or hydrolysis.

The compounds of formulae IV, V, VI, VIII, IX, X, XII, XIII and XV used as starting materials are obtained by reacting a corresponding amine with a suitable carboxylic acid or a reactive derivative thereof and, if necessary, subsequently splitting off any protecting group used.

A compound of formula XVII used as starting material is obtained by reducing a corresponding carbonyl compound by reacting a corresponding carbonyl compound with a corresponding grignard or lithium reagent or by hydrolysis or alcoholysis of a corresponding cyanohydrin and, if necessary, subsequent esterification.

A compound of formula XIX used as starting material is obtained by acylating a corresponding ketimine or the organometallic complex thereof with a corresponding carboxylic acid or reactive derivatives thereof, optionally with tautomerization.

Figure 1A:
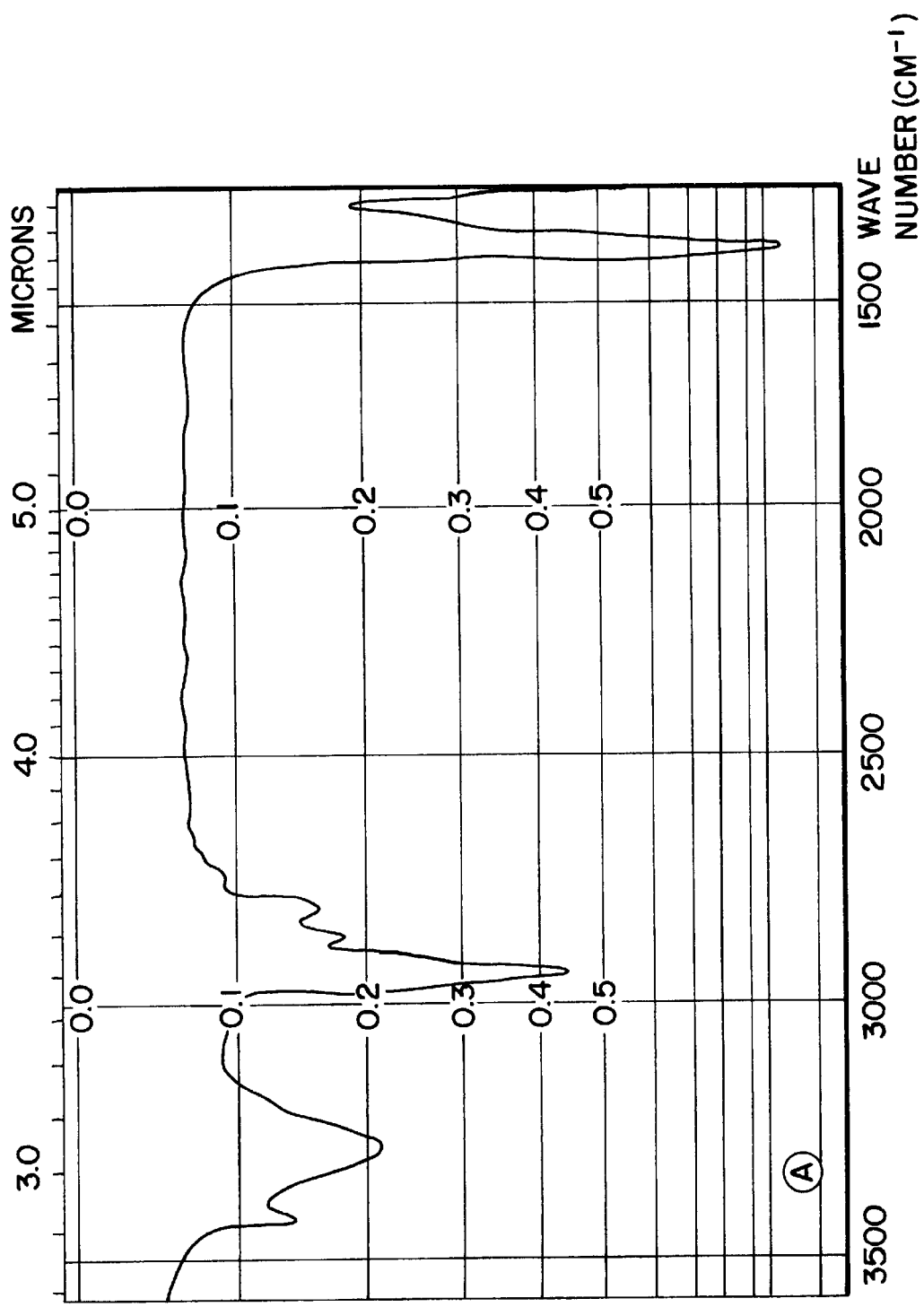
FIG. 1: 2-Ethoxy-4-[N-{1-(2-piperidino-phenyl)-3-methyl-1-butyl}-aminocarbonylmethyl]-benzoic acid (form A); dissolved in methylene chloride (IR)

The following examples illustrate the present invention and will enable other skilled in the art to understand it more completely. It should be understood, however, that the inventor is not limited solely to the particular examples given below.

EXAMPLE 1

Ethyl 2-ethoxy-4-[N-{1-(2-piperidino-phenyl)-1-butyl}amino-carbonylmethyl]-benzoate 2 g (7.9 mmols) of 3-ethoxy-4-ethoxycarbonyl-phenylacetic acid, 2.46 g (9.38 mmols) of triphenylphosphine, 1.7 ml (12.3 mmols) of triethylamine and 0.76 ml (7.9 mmols) of carbon tetra chloride were added to a solution of 1.84 g (7.9 mmols) of 1-(2-piperidinophenyl)-1-butylamine in 19 ml of acetonitrile, and the mixture was stirred for two days at room temperature. It was then evaporated in vacuo, and the residue was taken up in a mixture of ethyl acetate and water. The organic phase was dried filtered and evaporated in vacuo. The evaporation residue was purified by column chromtography on silica gel (toluene/acetone=5/1).

Yield: 3 g (81% of theory). M.p. 113–115° C. (petroleum ether). Calculated: C-72.07%; H-8.21%; N-6.00%. Found: C-72.18%; H-8.27%; N-6.16%.

The following compounds were prepared by a procedure analogous to that described in Example 1:

(a) Methyl 2-methoxy-4-[N-{1-(2-piperidino-phenyl)-1-ethyl}aminocarbonylmethyl]-benzoate Prepared from 1-(2-piperidino-phenyl)-1-ethylamine and 3-methoxy-4-methoxycarbonyl-phenylacetic acid.

Yield: 78% of theory. M.p. 82–85° C. Calculated: C-70.22%; H-7.37%; N-6.82%. Found: C-70.54%; H-7.49%; N-6.75%.

(b) Ethyl 2-ethoxy-4-[N-(α-phenyl-2-piperidino-benzyl) aminocarbonylmethyl]-benzoate Prepared from α-phenyl-2-piperidino-benzylamine and 3-ethoxy-4-ethoxycarbonyl-phenylacetic acid.

Yield: 77% of theory. M.p. 149–151° C. Calculated: C-74.37%; H-7.25%; N-5.60%. Found: C-74.69%; H-7.44%; N-5.59%.

(c) Methyl 2-methoxy-4-[N-(α-phenyl-2-piperidino-benzyl) aminocarbonylmethyl]-benzoate Prepared from α-phenyl-2-piperidino-benzylamine and 3-methoxy-4-methoxycarbonyl-phenylacetic acid.

Yield: 65% of theory. M.p. 189–190° C. Calculated: C-73.70%; H-6.83%; N-5.93%. Found: C-73.51%; H-6.75%; N-5.86%.

(d) Ethyl 2-ethoxy-4-[N-1-{2-piperidino-phenyl}-1-ethyl) aminocarbonylmethyl]-benzoate Prepared from 1-(2-piperidino-phenyl)-1-ethylamine and 3-ethoxy-4-ethoxycarbonyl-phenylacetic acid.

Yield: 69% of theory. M.p. 92–93° C. Calculated: C-71.21%; H-7.81%; N-6.39%. Found: C-71.29%; H-8.03%; N-6.58%.

(e) Ethyl 2-ethoxy-4-[N-{1-(5-chloro-2-piperidino-phenyl)-1-propyl}-aminocarbonylmethyl]-benzoate Prepared from 1-(5-chloro-2-piperidino-phenyl)-1-propylamine and 3-ethoxy-4-ethoxycarbonyl-phenylacetic acid.

Yield: 80% of theory. M.p. 110–112° C. Calculated: C-66.58%; H-7.24%; N-5.75%; Cl-7.28%. Found: C-66.61%; H-7.34%; N-5.86%; Cl-7.35%.

(f) Ethyl 2-ethoxy-4-[N-{1-(2-piperidino-phenyl)-1-pentyl}-aminocarbonylmethyl]-benzoate Prepared from 1-(2-piperidino-phenyl)-1-pentylamine and 3-ethoxy-4-ethoxycarbonyl-phenylacetic acid.

Yield: 63% of theory. M.p. 113–115° C. Calculated: C-72.47%; H-8.39%; N-5.83%. Found: C-72.66%; H-8.26%; N-5.99%.

(g) Ethyl 2-ethoxy-4-[N-{1-(2-pyrrolidino-phenyl)-1-butyl}-aminoclarbonylmethyl]-benzoate Prepared from 1-(2-pyrrolidino-phenyl)-1-butylamine and 3-ethoxy-4-ethoxycarbonyl-phenylacetic acid.

Yield: 50% of theory. M.p. 85–87° C. Calculated: C-71.65%; H-8.02%; N-6.19%. Found: C-71.90%; H-8.37%; N-6.34%.

(h) Ethyl 2-ethoxy-4-[N-{1-(2-(4-methyl-piperidino)-phenyl)-1-butyl}-aminocarbonylmethyl]-benzoate Prepared from 1-[2-(4-methyl-piperidino)-phenyl]-1-butylamine and 3-ethoxy-4-ethoxycarbonyl-phenylacetic acid.

Yield: 44% of theory. M.p. 127–128° C. Calculated: C-72.47%; H-8.39%; N-5.83%. Found: C-72.20%; H-8.23%; N-5.69%.

(i) Ethyl 2-ethoxy-4-[N-{1-(2-hexamethyleneimino-phenyl)-1-butyl}-aminocarbonylmethyl]-benzoate Preared from 1-(2-hexamethyleneimino-phenyl)-1-butylamine and 3-ethoxy-4-ethoxycarbonyl-phenylacetic acid.

Yield: 44% of theory. M.p. 97–100° C. Calculated: C-72.47%; H-8.39%; N-5.83%. Found: C-72.41%; H-8.50%; N-5.66%.

(k) Ethyl 2-ethoxy-4-[N-{1-(4-methyl-2-piperidino-phenyl)-1-butyl}-aminocarbonylmethyl]-benzoate Prepared from 1-(4-methyl-2-piperidino-phenyl)-1-butyl-amine and 3-ethoxy-4-ethoxycarbonyl-phenylacetic acid.

Yield: 68% of theory. M.p. 113–114° C. Calculated: C-72.47%; H-8.39%; N-5.83%. Found: C-72.36%; H-8.31%; N-5.91%.

(l) Ethyl 2-ethoxy-4-[N-{1-(6-methyl-2-piperidino-phenyl)-1-butyl}-aminocarbonylmethyl]-benzoate Prepared from 1-(6-methyl-2-piperidino-phenyl)-1-butyl-amine and 3-ethoxy-4-ethoxycarbonyl-phenylacetic acid.

Yield: 62% of theory. M.p. <20° C. Calculated: C-72.47%; H-8.39%; N-5.83%. Found: C-72.30%; H-8.50%; N-5.72%.

(m) Ethyl 2-ethoxy-4-[N-{1-(6-chloro-2-piperidino-phenyl)-1-butyl}-aminocarbonylmethyl]-benzoate Prepared from 1-(6-chloro-2-piperidino-phenyl)-1-butyl-amine and 3-ethoxy-4-ethoxycarbonyl-phenylacetic acid.

Yield: 85% of theory. M.p. <20° C. Calculates. C-67.12%; H-7.44%; N-5.50%; Cl-7.08%. Found. C-67.60%; H-7.77%; N-5.92%; Cl-7.24%.

(n) Ethyl 2-ethoxy-4-[N-{1-(4-methoxy-2-piperidino-phenyl)-1-butyl}-aminocarbonylmethyl]-benzoate Prepared from 1-(4-methoxy-2-piperidino-phenyl)-1-butyl-amine and 3-ethoxy-4-ethoxycarbonyl-phenylacetic acid.

Yield: 65% of theory. M.p. 109–110° C. Calculated: Mol. peak m/e=496; Found: Mol. peak m/e=496

(o) Ethyl 2-ethoxy-4-[N-{1-(5-methoxy-2-piperidino-phenyl)-1-butyl}-aminocarbonylmethyl]-benzoate Prepared from 1-(5-methoxy-2-piperidino-phenyl)-1-butyl amine and 3-ethoxy-4-ethoxycarbonyl-phenylacetic acid.

Yield: 31% of theory. M.p. 117–120° C. Calculated: Mol. peak m/e=496; Found: Mol. peak m/e=496

(p) Ethyl 2-hydroxy-4-[N-{1-(2-piperidino-phenyl)-1-butyl}-aminocarbonylmethyl]-benzoate Prepared from 1-(2-piperidino-phenyl)-1-butylamine and 4-ethoxycarbonyl-3-hydroxy-phenylacetic acid.

Yield: 46% of theory. M.p. 133–134° C. Calculated: C-71.21%; H-7.81%; N-6.39%. Found: C-71.08%; H-7.91%; N-6.45%.

(q) Methyl 2-methoxy-4-[N-{1-(2-piperidino-phenyl)-1-butyl}-aminocarbonylmethyl]-benzoate Prepared from 1-(2-piperidino-phenyl)-1-butylamine and 3-methoxy-4-methoxycarbonyl-phenylacetic acid.

Yield: 67% of theory. M.p. 128–131° C. Calculated: C-71.21%; H-7.81%; N-6.39%. Found: C-71.46%; H-7.80%; N-6.07%.

(r) n-Propyl 2-n-propoxy-4-[N-{1-(2-piperidino-phenyl)-1-butyl}-aminocarbonylmethyl]-benzoate Prepared from 1-(2-piperidino-phenyl)-1-butylamine and 3-n-propoxy-4-n-propoxycarbonyl-phenylacetic acid.

Yield: 56% of theory. M.p. 88–89° C. Calculated: C-72.84%; H-8.56%; N-5.66%. Found: C-72.80%; H-8.78%; N-5.78%.

(s) Ethyl 2-ethoxy-4-[N-(5-chloro-2-piperidino-benzyl)-aminocarbonylmethyl]-benzoate Prepared from 5-chloro-2-piperidino-benzylamine and 3-ethoxy-4-ethoxycarbonyl-phenylacetic acid.

Yield: 65% of theory. M.p. 106–108° C. Calculated: C-65.41%; H-6.81%; N-6.10%; Cl-7.73%. Found: C-65.81%; H-6.89%; N-6.11%; Cl-7.62%.

(t) Ethyl (−)-2-ethoxy-4-[N-(α-phenyl-2-piperidino-benzyl)-aminocarbonylmethyl]-benzoate Prepared from (−)-α-phenyl-2-piperidino-benzylamine and 3-ethoxy-4-ethoxycarbonyl-phenylacetic acid.

Yield: 87% of theory. M.p. 110–111° C. Calculated: mol peak m/e=500; Found: mol peak m/e=500; Specific rotation: $[\alpha]_D^{20}=-6.3°$ (c=1, methanol).

(u) Ethyl 2-ethoxy-4-[N-(6-methyl-α-phenyl-2-piperidino-benzyl)-aminocarbonylmethyl]-benzoate Prepared from 6-methyl-α-phenyl-2-piperidino-benzylamine and 3-ethoxy-4-ethoxycarbonyl-phenylacetic acid.

Yield: 39% of theory. M.p. <20° C. Calculated: C-74.68%; H-7.44%; N-5.44%. Found: C-74.81%; H-7.56%; N-5.32%.

(v) Ethyl 2-ethoxy-4-[N-{α-(4-methyl-phenyl)-2-piperidino-benzyl}-aminocarbonylmethyl]-benzoate Prepared from α-(4-methyl-phenyl)-2-piperidino-benzylamine and 3-ethoxy-4-ethoxycarbonyl-phenylacetic acid.

Yield: 34% of theory. M.p. 150–152° C. Calculated: C-74.68%; H-7.44%; N-5.44%. Found: C-74.71%; H-7.51%; N-5.29%.

(w) Ethyl 2-ethoxy-4-[N-(α-phenyl-2-pyrrolidino-benzyl)-aminocarbonylmethyl]-benzoate Prepared from α-phenyl-2-pyrrolidino-benzylamine and 3-ethoxy-4-ethoxycarbonyl-phenylacetic acid.

Yield: 45% of theory. M.p. 85–87° C. Calculated: C-74.05%; H-7.04%; N-5.76%. Found: C-73.95%; H-7.07%; N-5.70%.

(x) Methyl 2-methoxy-4-[N-(2-hexamethyleneimino-α-phenyl-benzyl)-aminocarbonylmethyl]-benzoate Prepared from 2-hexamethyleneimino-α-phenyl-benzylamine and 3-methoxy-4-methoxycarbonyl-phenylacetic acid.

Yield: 45% of theory. M.p. 181–183° C. Calculated: C-74.05%; H-7.04%; N-5.74%. Found: C-74.09%; H-6.62%; N-5.74%.

(y) Ethyl 2-ethoxy-4-[N-(2-hexamethyleneimino-α-phenyl-benzyl)-aminocarbonylmethyl]-benzoate Prepared from 2-hexamethyleneimino-α-phenyl-benzylamine and 3-ethoxy-4-ethoxycarbonyl-phenylacetic acid.

Yield: 41% of theory. M.p. 140–141° C. Calculated: C-74.68%; H-7.44%; N-5.44%. Found: C-74.46%; H-7.62%; N-5.45%.

(z) 2-Ethoxy-4-[N-{1-(2-piperidino-phenyl)-1-butyl}-aminocarbonylmethyl]-toluene Prepared from 1-(2-piperidino-phenyl)-1-butylamine an 3-ethoxy-4-methyl-phenylacetic acid.

Yield: 55% of theory. M.p. 107–108° C. Calculated: C-76.43%; H-8.88%; N-6.86%. Found: C-76.38%; H-8.99%; N-6.97%.

(aa) Ethyl 2-ethoxy-4-[N-{1-(2-piperidino-phenyl)-1-heptyl}-aminocarbonylmethyl]-benzoate Prepared from 1-(2-piperidino-phenyl)-1-heptylamine and 3-ethoxy-4-ethoxycarbonyl-phenylacetic acid.

Yield: 79% of theory. M.p. 101–104° C. Calculated: C-73.19%; H-8.72%; N-5.51%. Found: C-73.00%; H-8.90%; N-5.28%.

EXAMPLE 2

Ethyl (+)-2-ethoxy-4-[N-{1-(2-piperidino-phenyl)-1-butyl}-aminocarbonylmethyl]-benzoate 0.90 g (3.57 mmol) of 3-ethoxy-4-ethoxycarbonyl-phenylacetic acid and 0.61 g (3.73 mmol) of N,N'-carbonyldiimidazo are refluxed for 5 hours in 9 ml of absolute tetrahydrofuran Then a solution of 0.85 g (3.67 mmol) of (+)-1-(2-piperidino-phenyl)-1-butylamine (ee=94.2) in 9 ml of absolute tetrahydrofuran is added and the mixture is refluxed for 3 hours. It is concentrated in vacuo and the evaporation residue is distributed between chloroform and water. The organic phase is dried, filtered and evaporated in vacuo. The evaporated extract is purified by column chromatography on silica gel (toluene/acetone= 10.1).

Yield: 0.85 g (51.2% of theory). M.p. 118–119° C. (petroleum ether/toluene=50/2). Calculated: C-72.07%; H-8.21%; N-6.00%. Found: C-72.43%; H-8.34%; N-6.00%. Specific rotation: $[\alpha]_D^{20}=+7.1°$ (c=1.06 in methanol).

The following compounds were obtained analogously to Example 2:

(a) Methyl 3-methoxy-4-[N-{1-(2-piperidino-phenyl)-1-butyl}-aminocarbonylmethyl]-benzoate Prepared from 1-(2-piperidino-phenyl)-1-butylamine and 2-methoxy-4-methoxycarbonyl-phenylacetic acid.

Yield: 89% of theory. M.p. 102–105° C. Calculated: C-71.20%; H-7.81%; N-6.39%. Found: C-71.20%; H-8.02%; N-6.27%.

(b) Ethyl 3-ethoxy-4-[N-{1-(2-piperidino-phenyl)-1-butyl}-aminocarbonylmethyl]-benzoate Prepared from 1-(2-piperidino-phenyl)-1-butylamine and 2-ethoxy-4-ethoxycarbonyl-phenylacetic acid.

Yield: 73% of theory. M.p. 136–138° C. Calculated: C-72.07%; H-8.21%; N-6.00%. Found: C-72.50%; H-8.33%; N-5.95%.

(c) Ethyl 3-ethoxy-4-[N-{1-(4-methyl-2-piperidino-phenyl)-1-butyl}-aminocarbonylmethyl]-benzoate Prepared from 1-(4-methyl-2-piperidino-phenyl)-1-butyl-amine and 2-ethoxy-4-ethoxycarbonyl-phenylacetic acid.

Yield: 61% of theory. M.p. 108–110° C. Calculated: C-72.46%; H-8.39%; N-5.83%. Found: C-72.50%; H-8.46%; N-5.92%.

(d) Ethyl 3-ethoxy-4-[N-{1-(6-methyl-2-piperidino-phenyl)-1-butyl}-aminocarbonylmethyl]-benzoate Prepared from 1-(6-methyl-2-piperidino-phenyl)-1-butylamine and 2-ethoxy-4-ethoxycarbonyl-phenylacetic acid.

Yield: 90% of theory. M.p. <20° C. Calculated: C-72.46%; H-8.39%; N-5.83%. Found: C-72.86%; H-8.20%; N-5.50%.

(e) Methyl 3-methoxy-4-[N-(α-phenyl-2-piperidino-benzyl)-aminocarbonylmethyl]-benzoate Prepared from α-phenyl-2-piperidino-benzylamine and 2-methoxy-4-methoxycarbonyl-phenylacetic acid.

Yield: 86% of theory. M.p. 144–148° C. Calculated: C-73.70%; H-6.83%; N-5.93%. Found: C-73.70%; H-6.85%; N-5.84%.

(f) Ethyl 3-ethoxy-4-[N-(α-phenyl-2-piperidino-benzyl)-aminocarbonylmethyl]-benzoate Prepared from α-phenyl-2-piperidino-benzylamine and 2-ethoxy-4-ethoxycarbonyl-phenylacetic acid.

Yield: 77% of theory. M.p. 112–115° C. Calculated: C-74.37%; H-7.25%; N-5.60%. Found: C-74.69%; H-7.29%; N-5.75%.

EXAMPLE 3

Ethyl 2-ethoxy-4-[N-(α-phenyl-2-piperidino-benzyl)-aminocarbonylmethyl]-benzoate A solution of 4.7 g (20 mmol) of ethyl 2-ethoxy-4-cyanomethyl-benzoate and 5.3 g (20 mmol) of α-phenyl-2-piperidino-benzyl alcohol in 30 ml of 0-dichlorobenzene was added dropwis at 23–25° C. to a mixture of 30 ml of concentrated sulfuric acid and 30 ml of o-dichlorobenzene. The mixture was stirred for 2 hours at room temperature. Then, the o-dichlorobenzene phae was separated, and the residue was added to ice. After the aqueous mixture had been made alkaline with a soda solution, it was extracted with chloroform. The extracts were dried over magnesium sulfate and concentrated by evaporation. The residue was triturated with petroleum ether (30–60°), filtered off and purified on silica gel (toluene/ethylacetate=5:1) by column chromatography.

Yield: 5.6 g (56% of theory). M.p. 150–151° C. Calculated: C-74.37%; H-7.25%; N-5.60%. Found: C-74.59%; H-7.41%; N-5.45%.

The following compounds were obtained by a procedure analogous to that described in Example 3:

(a) Methyl 2-methoxy-4-[N-(α-phenyl-2-piperidino-benzyl)-aminocarbonylmethyl]-benzoate Prepared from α-phenyl-2-piperidino-benzyl alcohol and methyl 4-cyanomethyl-2-methoxy-benzoate.

Yield: 34% of theory. M.p. 189–191° C. Calculated: C-73.70%; H-6.83%; N-5.93%. Found: C-73.63%; H-7.05%; N-5.95%.

(b) 2-Ethoxy-4-[N-(α-phenyl-2-piperidino-benzyl)-aminocarbonylmethyl]-benzoic acid Prepared from α-phenyl-2-piperidino-benzyl alcohol and 2-ethoxy-4-cyanomethyl-benzoic acid.

Extraction at pH 5; Yield: 47% of theory; M.p. 154–155° C. Calculated: C-73.70%; H-6.83%; N-5.93%. Found: C-73.61%; H-6.72%; N-5.65%.

(c) 2-Methoxy-4-[N-(α-phenyl-2-piperidino-benzyl)-aminocarbonylmethyl]-benzoic acid Prepared from α-phenyl-2-piperidino-benzyl alcohol and 4-cyanomethyl-2-methoxy-benzoic acid.

Extraction at pH 5. Yield: 30% of theory. M.p. 202-204° C. Calculated: C-73.34%; H-6.59%; N-6.11%. Found: C-73.17%; H-6.41%; N-6.05%.

(d) Ethyl 2-ethoxy-4-[N-{1-(2-piperidino-phenyl)-1-butyl}-aminocarbonylmethyl]-benzoate Prepared from 1-(2-piperidino-phenyl)-1-butanol and ethyl-2-ethoxy-4-cyanomethyl benzoate.

Yield: 5% of theory. M.p. 112–114° C. Calculated: C-72.07%; H-8.21%; N-6.00%. Found: C-72.29%; H-8.46%; N-6.31%.

(e) Methyl 2-methoxy-4-[N-{1-(2-piperidino-phenyl)-1-ethyl}-aminocarbonylmethyl]-benzoate Prepared from 1-(2-piperidino-phenyl)-1-ethanol and methyl 4-cyanomethyl-2-methoxy-benzoate.

Yield: 18% of theory. M.p. 83–85° C. Calculated: C-70.22%; H-7.37%; N-6.82%. Found: C-70.60%; H-7.29%; N-6.97%.

(f) 2-Methoxy-4-[N-{1-(2-piperidino-phenyl)-1-ethyl}-aminocarbonylmethyl]-benzoic acid Prepared from 1-(2-piperidino-phenyl)-1-ethanol and 4-cyanomethyl-2-methoxy-benzoic acid.

Extraction at pH 5.5. Yield: 21% of theory. M.p. 118–120° C. Calculated: m/e=396; Found: m/e=396.

(g) Ethyl 2-ethoxy-4-[N-(4-methyl-α-phenyl-2-piperidino-benzyl)aminocarbonylmethyl]-benzoate Prepared from 4-methyl-α-phenyl-2-piperidino-benzyl alcohol and ethyl 2-ethoxy-4-cyanomethyl-benzoate.

Yield: 45% of theory. M.p. 124–125° C. Calculated: C-74.68%; H-7.44%; N-5.44%. Found: C-74.81%; H-7.56%; N-5.32%.

(h) Methyl 2-methoxy-4-[N-{α-(4-chloro-phenyl)-2-piperidino-benzyl)-aminocarbonylmethyl]-benzoate Prepared from α-(4-chlorophenyl)-2-piperidino-benzyl alcohol and methyl 2-methoxy-4-cyanomethyl-benzoate.

Yield: 47% of theory. M.p. 176–178° C. Calculated: C-68.70%; H-6.17%; N-5.53%; Cl-6.99%. Found: C-69.05%; H-5.93%; N-5.76%; Cl-7.10%.

(i) Ethyl 2-hydroxy-4-[N-(α-phenyl-2-piperidino-benzyl)-aminocarbonylmethyl]-benzoate Prepared from α-phenyl-2-piperidino-benzyl alcohol and ethyl 4-cyanomethyl-2-hydroxy-benzoate.

Yield: 78% of theory. M.p. 172–174° C. Calculated: C-73.70%; H-6.83%; N-5.93%. Found: C-73.80%; H-6.81%; N-5.83%.

(k) n-Propyl 2-n-propoxy-4-[N-(α-phenyl-2-piperidino-benzyl)-aminocarbonylmethyl]-benzoate Prepared from α-phenyl-2-piperidino-benzyl alcohol and n-propyl 4-cyanomethyl-2-n-propoxy benzoate.

Yield: 52% of theory. M.p. 119–120° C. Calculated: C-74.97%; H-7.63%; N-5.30%. Found: C-74.91%; H-7.72%; N-5.25%.

EXAMPLE 4

2-Ethoxy-4-[N-{1-(2-piperidino-phenyl)-1-butyl}-aminocarbonylmethyl]-benzoic acid A mixture of 2 g (4.3 mmols) of ethyl 2-ethoxy-4-[N-{1-(2-piperidino-phenyl)-1-butyl}-aminocarbonylmethyl]-benzoate and 5.3 ml of 1N sodium hydroxide solution in 20 ml of ethanol was stirred for 3 hours at 60° C., then neutralized with 5.3 ml of 1N hydrochloric acid, and the ethanol was evaporated in vacuo. The residue was taken up in a mixture of ethyl acetate and water, and the organic phase was dried, filtered and evaporate in vacuo. The evaporation residue was crystallized from petroleum ether with the addition of ethanol.

Yield: 1.3 g (69% of theory). M.p. 88–90° C. Calculated: C-71.21%; H-7.81%; N-6.39%. Found: C-71.62%; H-7.73%; N-6.54%.

The following compounds were obtained by a procedure analogous to that described in Example 4:

(a) 2-Methoxy-4-[N-{1-(2-piperidino-phenyl)-1-ethyl}-aminocarbonylmethyl]-benzoic acid×0.67 H₂O Prepared from methyl 2-methoxy-4-[N-{1-(2-piperidino-phenyl)-1-ethyl}-aminocarbonylmethyl]-benzoate.

Yield: 60% of theory. M.p. 116–120° C. Calculated: C-67.62%; H-7.07%; N-6.85%. Found: C-67.60%; H-6.87%; N-6.55%.

(b) 2-Ethoxy-4-[N-(α-phenyl-2-piperidino-benzyl)-aminocarbonylmethyl]-benzoic acid Prepared from ethyl 2-ethoxy-4-[N-(α-phenyl-2-piperidino-benzyl)-aminocarbonylmethyl]-benzoate.

Yield: 89% of theory. M.p. 155–156° C. Calculated: C-73.70%; H-6.83%; N-5.93%. Found: C-73.60%; H-6.96%; N-6.12%.

(c) 2-Methoxy-4-[N-(α-phenyl-2-piperidino-benzyl)-aminocarbonylmethyl)-benzoic acid Prepared from methyl 2-methoxy-4-[N-(α-phenyl-2-piperidino-benzyl)-aminocarbonylmethyl]-benzoate.

Yield: 68% of theory. M.p. 202–204° C. Calculated: C-73.34%; H-6.59%; N-6.11%. Found: C-73.60%; H-6.77%; N-6.20%.

(d) 2-Ethoxy-4-[N-{1-(5-chloro-2-piperidino-phenyl-1-propyl}-aminocarbonylmethyl]-benzoic acid Prepared from ethyl 2-ethoxy-4-[N-{1-(5-chloro-2-piperidino-phenyl)-1-propyl}-aminocarbonylmethyl]-benzoate.

Yield: 74% of theory. M.p. 115–118° C. Calculated: C-65.42%; H-6.81%; N-6.10%; Cl-7.72%. Found: C-65.54%; H-6.94%; N-5.81%; Cl-7.89%.

(e) 2-Ethoxy-4-[N-{1-(2-piperidino-phenyl)-1-propyl}-aminocarbonylmethyl]-benzoic acid Prepared from ethyl 2-ethoxy-4-[N-{1-(2-piperidino-phenyl-1-propyl}-aminocarbonylmethyl]-benzoate.

Yield: 73% of theory. M.p. 81–83° C. Calculated: C-70.73%; H-7.60%; N-6.60%. Found: C-70.90%; H-7.47%; N-6.77%.

(f) 2-Ethoxy-4-[N-{1-(2-piperidino-phenyl)-1-pentyl}-aminocarbonylmethyl]-benzoic acid Prepared from ethyl 2-ethoxy-4-[N-{1-(2-piperidino-pheny-1-pentyl}-aminocarbonylmethyl]-benzoate.

Yield: 92% of theory. M.p. 82–85° C. Calculated: C-71.65%; H-8.02%; N-6.19%. Found: C-71.45%; H-8.01%; N-6.13%.

(g) 2-Ethoxy-4-[N-{1-(2-pyrrolidino-phenyl)-1-butyl}-aminocarbonylmethyl]-benzoic acid Prepared from ethyl 2-ethoxy-4-[N-{1-(2-pyrrolidino-phenyl)-1-butyl}-aminocarbonylmethyl]-benzoate.

Yield: 77% of theory. M.p. 120–123° C. Calculated: C-70.73%; H-7.60%; N-6.60%. Found: C-70.71%; H-7.44%; N-6.33%.

(h) 2-Ethoxy-4-[N-{1-(2-(4-methyl-piperidino)-phenyl)-1-butyl}-aminocarbonylmethyl]-benzoic acid Prepared from ethyl 2-ethoxy-4-[N-{1-(2-(4-methyl-piperidino)-phenyl)-1-butyl}-aminocarbonylmethyl]-benzoate.

Yield: 71% of theory. M.p. 83–85° C. Calculated: C-71.65%; H-8.02%; N-6.19%. Found: C-71.60%; H-7.94%; N-6.09%.

(i) 2-Ethoxy-4-[N-{1-(2-hexamethyleneimino-phenyl)-1-butyl}-aminocarbonylmethyl]-benzoic acid Prepared from ethyl 2-ethoxy-4-[N-{1-(2-hexamethyleneimino-phenyl)-1-butyl}-aminocarbonylmethyl]-benzoate.

Yield: 81% of theory. M.p. 101–105° C. Calculated: C-71.65%; H-8.02%; N-6.19%. Found: C-71.31%; H-7.79%; N-6.18%.

(k) 2-Ethoxy-4-[N-{1-(6-chloro-2-piperidino-phenyl)-1-butyl}-aminocarbonylmethyl]-benzoic acid Prepared from ethyl 2-ethoxy-4-[N-{1-(6-chloro-2-piperidino-phenyl)-1-butyl}-aminocarbonylmethyl]-benzoate.

Yield: 82% of theory. M.p. 133–136° C. Calculated: C-66.02%; H-7.03%; N-5.92%; Cl-7.50%. Found: C-66.48%; H-7.47%; N-5.98%; Cl-7.88%.

(l) 2-Ethoxy-4-[N-{1-(4-methoxy-2-piperidino-phenyl)-1-butyl}-aminocarbonylmethyl]-benzoic acid Prepared from ethyl 2-ethoxy-4-[N-{1-(4-methoxy-2-piperidino-phenyl)-1-butyl}-aminocarbonylmethyl]-benzoate.

Yield: 81% of theory. M.p. 98–100° C. Calculated: C-69.21%; H-7.74%; N-5.98%. Found: C-69.12%; H-7.62%; N-5.78%.

(m) 2-Ethoxy-4-[N-{1-(5-methoxy-2-piperidino-phenyl)-1-butyl}-aminocarbonylmethyl]-benzoic acid Prepared from ethyl 2-ethoxy-4-[N-{1-(5-methoxy-2-piperidino-phenyl)-1-butyl}-aminocarbonylmethyl]-benzoate.

Yield: 74% of theory. M.p. 145–148° C. Calculated: C-69.21%; H-7.74%; N-5.98%. Found: C-69.00%; H-7.65%; N-5.89%.

(n) 2-Methoxy-4-[N-{1-(2-piperidino-phenyl)-1-butyl}-aminocarbonylmethyl]-benzoic acid Prepared from methyl 2-methoxy-4-[N-{1-(2-piperidino-phenyl)-1-butyl}-aminocarbonylmethyl]-benzoate.

Yield: 86% of theory. M.p. 140–143° C. Calculated: C-70.73%; H-7.60%; N-6.60%. Found: C-70.49%; H-7.58%; N-6.31%.

(o) 2-n-Propoxy-4-[N-{1-(2-piperidino-phenyl)-1-butyl}-aminocarbonylmethyl]-benzoic acid Prepared from n-propyl 2-n-propoxy-4-[N-{1-(2-piperidino-phenyl)-1-butyl}-aminocarbonylmethyl]-benzoate.

Yield: 89% of theory. M.p. 128–132° C. Calculated: C-71.65%; H-8.02%; N-6.19%. Found: C-71.40%; H-7.90%; N-6.47%.

(p) 2-Ethoxy-4-[N-(5-chloro-2-piperidino-benzyl)-aminocarbonylmethyl]-benzoic acid×0.5 H$_2$O Prepared from ethyl 2-ethoxy-4-[N-5-chloro-2-piperidino-benzyl)-aminocarbonylmethyl]-benzoate.

Yield: 93% of theory. M.p. 153–155° C. Calculated: C-62.79%; H-6.41%; N-6.36%; Cl-8.06%. Found: C-63.21%; H-6.34%; N-5.89%; Cl-8.46%.

(q) 2-Ethoxy-4-[N-(2-piperidino-benzyl)-aminocarbonylmethyl]-benzoic acid

Prepared from ethyl 2-ethoxy-4-[N-(2-piperidino-benzyl)-aminocarbonylmethyl]-benzoate.

Yield: 77% of theory. M.p. 108–109° C. Calculated: C-69.68%; H-7.12%; N-7.07%. Found: C-70.00%; H-7.99%; N-7.31%.

(r) 2-Hydroxy-4-[N-{1-(2-piperidino-phenyl)-1-butyl}-aminocarbonylmethyl]-benzoic acid Prepared from ethyl 2-hydroxy-4-[N-{1-(2-piperidino-phenyl)-1-butyl}-aminocarbonylmethyl]-benzoate.

Yield: 61% of theory. M.p. 136–138° C. Calculated: C-70,22%; H-7.37%; N-6.82%. Found: C-70.40%; H-7.64%; N-6.60%.

(s) 2-Isopropoxy-4-[N-{1-(2-piperidino-phenyl)-1-butyl}-aminocarbonylmethyl]-benzoic acid Prepared from ethyl 2-isopropoxy-4-[N-{1-(2-piperidino-phenyl)-1-butyl}-aminocarbonylmethyl]-benzoate.

Yield: 67% of theory. M.p. 115–118° C. Calculated: C-71.65%; H-8.02%; N-6.19%. Found: C-71.94%; H-7.96%; N-6.04%.

(t) 2-Allyloxy-4-[N-{1-(2-piperidino-phenyl)-1-butyl}-aminocarbonylmethyl]-benzoic acid Prepared from ethyl 2-allyloxy-4-[N-{1-(2-piperidino-phenyl)-1-butyl}-aminocarbonylmethyl]-benzoate.

Yield: 92% of theory. M.p. 110–112° C. Calculated: C-71.97%; H-7.61%; N-6.22%. Found: C-71.90%; H-7.62%; N-6.21%.

(u) 2-Benzyloxy-4-[N-{1-(2-piperidino-phenyl)-1-butyl}-aminocarbonylmethyl]-benzoic acid Prepared from ethyl 2-benzyloxy-4-[N-{1-(2-piperidino-phenyl)-1-butyl}-aminocarbonylmethyl]-benzoate.

Yield: 95% of theory. M.p. 161–163° C. Calculated: C-74.37%; N-7.25%; N-5.60%. Found: C-74.40%; N-7.44%; N-5.64%.

(v) (+)-2-Ethoxy-4-[N-{1-(2-piperidino-phenyl)-1-butyl}-aminocarbonylmethyl]-benzoic acid Prepared from ethyl (+)-2-ethoxy-4-[N-{1-(2-piperidino-phenyl)-1-butyl}-aminocarbonylmethyl]benzoate.

Yield: 81% of theory. M.p. 122–123° C. Calculated: C-71.21%; H-7.81%; N-6.39%. Found: C-71.19%; H-7.77%; N-6.29%. Specific rotation $[\alpha]_D^{20}$=4.75° (c=1.03 in methanol).

(w) 3-Methoxy-4-[N-{1-(2-piperidino-phenyl)-1-butyl}-aminocarbonylmethyl]-benzoic acid Prepared from methyl 3-methoxy-4-[N-{1-(2-piperidino-phenyl)-1-butyl}-aminocarbonylmethyl]-benzoate.

Yield: 64% of theory. M.p. 188–191° C. Calculated: C-70.73%; H-7.60%; N-6.60%. Found: C-70.88%; H-7.56%; N-6.59%.

(x) 3-Ethoxy-4-[N-{1-(2-piperidino-phenyl)-1-butyl}-aminocarbonylmethyl]-benzoic acid Prepared from ethyl 3-ethoxy-4-[N-{1-(2-piperidino-phenyl)-1-butyl}-aminocarbonylmethyl]-benzoate.

Yield: 79% of theory. M.p. 159–165° C. Calculated: C-71.21%; H-7.81%; N-6.39%. Found: C-71.32%; H-7.62%; N-6.24%.

(y) 3-Ethoxy-4-[N-{1-(4-methyl-2-piperidino-phenyl)-1-butyl}-aminocarbonylmethyl]-benzoic acid Prepared from ethyl 3-ethoxy-4-[N-{1-(4-methyl-2-piperidino-phenyl)-1-butyl}-aminocarbonylmethyl]-benzoate.

Yield: 71% of theory. M.p. 186–188° C. Calculated: C-71.65%; H-8.02%; N-6.19%. Found: C-71.70%; H-7.86%; N-6.26%.

(z) 3-Ethoxy-4-[N-{1-(6-methyl-2-piperidino-phenyl)-1-butyl}-aminocarbonylmethyl]-benzoic acid Prepared from ethyl 3-ethoxy-4-[N-{1-(6-methyl-2-piperidino-phenyl)-1-butyl}-aminocarbonylmethyl]-benzoate.

Yield: 65% of theory. M.p. 174–176° C. Calculated: C-71.65%; H-8.02%; N-6.19%. Found: C-72.00%; H-8.10%; N-5.91%.

(aa) 2-Ethoxy-4-[N-(4-methyl-α-phenyl-2-piperidino-benzyl)-aminocarbonylmethyl]-benzoic acid Prepared from ethyl 2-ethoxy-4-[N-(4-methyl-α-phenyl-2-piperidino-benzyl)-aminocarbonylmethyl]-benzoate.

Yield: 41% of theory. M.p. 127–129° C. Calculated: C-74.05%; H-7.04%; N-5.76%. Found: C-73.80%; H-7.09%; N-5.74%.

(ab) 2-Ethoxy-4-[N(6-methyl-α-phenyl-2-piperidino-benzyl)-aminocarbonylmethyl]-benzoic acid Prepared from ethyl 2-ethoxy-4-[N-(6-methyl-α-phenyl-2-piperidino-benzyl)-aminocarbonylmethyl]-benzoate.

Yield: 40% of theory. M.p. 118–121° C. Calculated: C-74.05%; H-7.04%; N-5.76%. Found: C-73.71%; H-6.92%; N-5.76%.

(ac) 2-Ethoxy-4-[N-{α-(4-methyl-phenyl)-2-piperidino-benzyl}-aminocarbonylmethyl]-benzoic acid Prepared from ethyl 2-ethoxy-4-[N-{α-(4-methyl-phenyl)-2-piperidino-benzyl}-aminocarbonylmethyl]-benzoate.

Yield: 94% of theory. M.p. 148–151° C. Calculated: C-74.05%; H-7.04%; N-5.76%. Found: C-74.20%; H-7.15%; N-5.81%.

(ad) 2-Methoxy-4-[N-{α-(4-chloro-phenyl)-2-piperidino-benzyl}-aminocarbonylmethyl]-benzoic acid Prepared from methyl 2-methoxy-4-[N-{α-(4-chloro-phenyl)-2-piperidino-benzyl}-aminocarbonylmethyl]-benzoate.

Yield: 77% of theory. M.p. 177–180° C. Calculated: C-68.21%; H-5.93%; N-5.68%; Cl-7.19%. Found: C-68.10%; H-5.78%; N-5.53%; Cl-7.43%.

(ae) 2-Ethoxy-4-[N-(α-phenyl-2-pyrrolidino-benzyl)-amino-carbonylmethyl]-benzoic acid Prepared from ethyl 2-ethoxy-4-[N-(α-phenyl-2-pyrrolidino-benzyl)-aminocarbonylmethyl]-benzoate.

Yield: 67% of theory. M.p. 141–143° C. Calculated: C-73.34%; H-6.59%; N-6.11%. Found: C-73.33%; H-6.74%; N-6.02%.

(af) 2-Methoxy-4-[N-(2-hexamethyleneimino-α-phenyl-benzyl)-aminocarbonylmethyl]-benzoic acid Prepared from methyl 2-methoxy-4-[N-(2-hexamethyleneimino-α-phenyl-benzyl)-aminocarbonylmethyl]-benzoate.

Yield: 90% of theory. M.p. 154–156° C. Calculated: C-73.70%; H-6.83%; N-5.93%. Found: C-73.70%; H-7.00%; N-5.95%.

(ag) 2-Ethoxy-4-[N-(2-hexamethylenaimino-α-phenyl-benzyl)-aminocarbonylmethyl]-benzoic acid Prepared from ethyl 2-ethoxy-4-[N-(2-hexamethyleneimino-α-phenyl-benzyl)-aminocarbonylmethyl]-benzoate.

Yield: 75% of theory. M.p. 139–141° C. Calculated: C-74.05%; H-7.04%; N-5.76%. Found: C-73.90%; H-7.14%; N-5.79%.

(ah) 2-Hydroxy-4-[N-(α-phenyl-2-piperidino-benzyl)-aminocarbonylmethyl]-benzoic acid Prepared from ethyl 2-hydroxy-4-[N-(α-phenyl-2-piperidino-benzyl)-aminocarbonylmethyl]-benzoate by hydrolysis with 4 equivalents of 1N sodium hydroxide in ethanol/dioxane.

Yield: 35% of theory. M.p. 222–224° C. Calculated: C-72.95%; H-6.35%; N-6.30%. Found: C-73.00%; H-6.64%; N-6.28%.

(ai) 2-n-Propoxy-4-[N-(α-phenyl-2-piperidino-benzyl)-aminocarbonylmethyl]-benzoic acid Prepared from n-propyl 2-n-propoxy-4-[N-(α-phenyl-2-piperidino-benzyl)-aminocarbonylmethyl]-benzoate.

Yield: 41% of theory. M.p. 168–170° C. Calculated: C-74.05%; H-7.04%; N-5.76%. Found: C-74.20%; H-7.19%; N-5.57%.

(ak) 2-Allyloxy-4-[N-(α-phenyl-2-piperidino-benzyl)-aminocarbonylmethyl]-benzoic acid Prepared from ethyl 2-allyloxy-4-[N-(α-phenyl-2-piperidino-benzyl)-aminocarbonylmethyl]-benzoate.

Yield: 69% of theory. M.p. 172–173° C. Calculated: C-74.35%; H-6.66%; N-5.78%. Found: C-74.11%; H-6.50%; N-5.74%.

(al) 2-Benzyloxy-4-[N-(α-phenyl-2-piperidino-benzyl)-aminocarbonylmethyl]-benzoic acid Prepared from ethyl 2-benzyloxy-4-[N-(α-phenyl-2-piperidino-benzyl)-aminocarbonylmethyl]-benzoate.

Yield: 72% of theory. M.p. 214–215° C. Calculated: C-76.38%; H-6.41%; N-5.24%. Found: C-76.18%; H-6.39%; N-5.36%.

(am) (−)-2-Ethoxy-4-[N-(α-phenyl-2-piperidino-benzyl)-aminocarbonylmethyl]-benzoic acid Prepared from ethyl (−)-2-ethoxy-4-[N-(α-phenyl-2-piperidino-benzyl)-aminocarbonylmethyl]-benzoate.

Yield: 89% of theory. M.p. 90–95° C. Calculated: C-73.70%; H-6.83%; N-5.93%. Found: C-73.59%; H-6.81%; N-5.83%. Specific rotation: $[\alpha]_D^{20}=-2.2°$ (c=1 in methanol).

(an) 3-Methoxy-4-[N-(α-phenyl-2-piperidino-benzyl)-amino-carbonylmethyl]-benzoic acid Prepared from methyl 3-methoxy-4-[N-(α-phenyl-2-piperidino-benzyl)-aminocarbonylmethyl]-benzoate.

Yield: 72% of theory. M.p. 220–221° C. Calculated: C-73.34%; H-6.59%; N-6.11%. Found: C-73.36%; H-6.46%; N-5.85%.

(ao) 3-Ethoxy-4-[N-(α-phenyl-2-piperidino-benzyl)-aminocarbonylmethyl]-benzoic acid Prepared from ethyl 3-ethoxy-4-[N-(α-phenyl-2-piperidino-benzyl)-aminocarbonylmethyl]-benzoate.

Yield: 70% of theory. M.p. 199–201° C. Calculated: C-73.70%; H-6.83%; N-5.93%. Found: C-73.50%; H-6.74%; N-5.94%.

(ap) 2-Ethoxy-4-[N-{1-(2-piperidino-phenyl)-1-heptyl}-aminocarbonylmethyl]-benzoic acid Prepared from ethyl 2-ethoxy-4-[N-{1-(2-piperidino-phenyl)-1-heptyl}-aminocarbonylmethyl]-benzoate.

Yield: 88% of theory. M.p. 71–73° C. Calculated: C-72.47%; H-8.39%; N-5.83%. Found: C-72.28%; H-8.56%; N-5.82%.

EXAMPLE 5

Sodium salt of 2-ethoxy-4-[N-{1-(2-piperidino-phenyl}-1-ethyl)-aminocarbonylmethyl]-benzoic acid×1.5 H₂O Prepared from ethyl 2-ethoxy-4-[N-{1-(2-piperidino-phenyl)-1-ethyl}-aminocarbonylmethyl]-benzoate analogous to Example 4. After purification by column chromatography the evaporation residue was dissolved in ethanol and mixed with 1 equivalent of 1N sodium hydroxide. By evaporation in vacuo and trituration with acetone, the crystalline sodium salt was obtained.

Yield: 76% of theory. M.p. 242–244° C. Calculated: C-62.738; H-7.01%; N-6.01%. Found: C-62.74%; H-7.17%; N-6.05%.

The following compounds were obtained by a procedure analogous to that described in Example 5:
(a) Sodium salt of 2-ethoxy-4-[N-{1-(4-methyl-2-piperidino-phenyl)-1-butyl}-aminocarbonylmethyl]-benzoic acid×0.5 $H_2O$ Prepared from ethyl 2-ethoxy-4-[N-{1-(4-methyl-2-piperidino-phenyl)-1-butyl}-aminocarbonylmethyl]-benzoate.

Yield: 72% of theory. M.p. 255–260° C. Calculated: C-67.06%; H-7.50%; N-5.79%. Found: C-66.94%; H-7.28%; N-5.50%.
(b) Sodium salt of 2-ethoxy-4-[N-{1-(6-methyl-2-piperidino-phenyl)-1-butyl}-aminocarbonylmethyl]-benzoic acid×2.5 $H_2O$ Prepared from ethyl 2-ethoxy-4-[N-{1-(6-methyl-2-piperidino-phenyl)-1-butyl}-aminocarbonylmethyl]-benzoate.

Yield: 81% of theory. M.p. 232–2240° C. Calculated: C-62.39%; H-7.75%; N-5.39%. Found: C-62.22%; H-7.46%; N-5.61%.
(c) Sodium salt of 2-ethoxy-4-[N-{1-(2-piperidino-phenyl)-1-butyl}-aminocarbonylmethyl]-benzoic acid Prepared from ethyl 2-ethoxy-4-[N-{1-(2-piperidino-phenyl 1-butyl}-aminocarbonylmethyl]-benzoate.

Yield: 87% of theory. M.p. 250–258° C. Calculated: C-67.79%; H-7.22%; N-6.08%. Found: C-67.60%; H-7.37%; N-6.04%.
(d) Sodium salt of 2-ethoxy-4-(α-phenyl-2-piperidino-benzyl)-aminocarbonylmethyl]-benzoic acid Prepared from ethyl 2-ethoxy-4-[N-(α-phenyl-2-piperidin benzyl)-aminocarbonylmethyl]-benzoate.

Yield: 89% of theory. M.p. 233–235° C. Caclulated: C-70.42% H-6.32%; N-5.67%. Found: C-70.20%; H-6.41%;. N-5.49%.

EXAMPLE 6

Ethyl 2-hydroxy-4-[N-(α-phenyl-2-piperidino-benzyl)-aminocarbonylmethyl]-benzoate 1 ml (10.4 mmols) of boron tribromide was added dropwise at –20° C. under anhydrous conditions to a stirred solution of 2 g (4 mmols) of ethyl 2-ethoxy-4-[N-(α-phenyl-2-piperidino-benzyl)-aminocarbonylmethyl]-benzoate in 20 ml of 1,2-dichloro ethane. The mixture was allowed to reach room temperature and was then stirred for 17 hours. It was then poured into ethano evaporated in vacuo, ice was added, and the resulting mixture was taken up in a mixture of chloroform and water. The organic phase was dried, filtered and evaporated in vacuo. The evaporation residue was purified by column chromatography on silica gel (toluene/ethyl acetate=5/1).

Yield: 0.37 g (21% of theory). M.p. 172–173° C. Calculated: C-73.70%; H-6.83%; N-5.93%. Found: C-73.95%; H-7.05%; N-6.12%.

The following compounds were obtained by a procedure analogous to that described in Example 6:
(a) 2-Hydroxy-4-[N-(α-phenyl-2-piperidino-benzyl)-aminocarbonylmethyl]-benzoic acid Prepared from 2-ethoxy-4-[N-(α-phenyl-2-piperidino-benzyl)-aminocarbonylmethyl]-benzoic acid.

Yield: 40% of theory. M.p. 221–223° C. Calculated: C-72.95%; H-6.35%; N-6.30%. Found: C-72.68%; H-6.45%; N6.49%.
(b) Ethyl 2-hydroxy-4-[N-{1-(2-piperidino-phenyl)-1-butyl}-aminocarbonylmethyl]-benzoate Prepared from ethyl 2-ethoxy-4-[N-{1-(2-piperidino-phenyl)-1-butyl}-aminocarbonylmethyl]-benzoate.

Yield: 19% of theory. M.P. 132–134° C.; Calculated: C-71.21; H-7.81; N-6.39; Found: C-71.43; H-7.91; N-6.55;
c) 2-Hydroxy-4-[N-(1-(2-pipridino-phenyl)-1-butyl)-aminocarbonylmethyl]-benzoic acid Prepared from 2-ethoxy-4-[N-(1-(2-piperidino-phenyl)-1-butyl)-aminocarbonylmethyl]-benzoic acid Yield: 42% of theory, M.P. 136–137° C.; Calculated: C-70.22%; H-7.37%; N-6.82%. Found: C-70.19%; H-7.39%; N-6.99%.

EXAMPLE 7

Tert.butyl 2-ethoxy-4-[N-{1-2-piperidino-phenyl)-1-butyl}-aminocarbonylmethyl]-benzoate A mixture of 1.9 g (9.6 mmols) of N,N'-dicyclohexyl-carbodiimide, 1.06 ml (11.2 mmols) of absolute tert.butanol and 0.020 g (0.20 mmol) of copper(I) chloride was stirred for 60 hours at room temperature. Then, 6.6 ml of methylene chloride were added, and the resulting solution was added dropwise to a solution of 0.44 g (1 mmol) of 2-ethoxy-4-[N-{1-(2-piperidinophenyl)-1-butyl}-aminocarbonyl-methyl]-benzoic acid in 15 ml of methylene chloride. After 60 hours' stirring at 20° C., the precipitate which had formed was filtered off, washed with methylene chloride, and the methylene chloride solution was evaporated in vacuo. The evaporation residue was purified by column chromatography on silica gel (chloroform/ethyl acetate=9/1).

Yield: 0.30 g (60% of theory). M.p. 74–77° C. (from petroleum ether). Calculated: C-72.84%; H-8.56%; N-5.66%. Found: C-73.00%; H-8.65%; N-5.79%.

EXAMPLE 8

Ethyl 2-benzyloxy-4-[N-(α-phenyl-2-piperidino-benzyl)-aminocarbonylmethyl]-benzoate 0.10 g (2.3 mmols) of sodium hydride (55% in oil) was added to a solution of 1.1 g (2.3 mmols) of ethyl 2-hydroxy-4-[N-(α-phenyl-2-piperidino-benzyl)-aminocarbonyl-methyl]-benzoate in 10 ml of anhydrous dimethylformamide and the resulting mixture was stirred for half an hour at room temperature. Then a solution of 0.27 ml (2.3 mmols) of benzyl bromide in 5 ml of anhydrous dimethylformamide was added dropwise, and the resulting mixture was stirred for 5 hours at room temperature. It was the evaporated in vacuo, the residue was taken up in a mixture of dilute sodium hydroxide and chloroform, and the organic phase was dried, filtered and evaporated in vacuo. The evaporation residue was recrystallized from acetonitrile.

Yield: 0.9 g (69.5% of theory). M.p. 156–157° C. Calculated: C-76.84%; H-6.81%; N-4.98%. Found: C-76.94%; H-6.95%; N-4.87%.

The following compounds were obtained by a procedure analogous to that described in Example 8:
(a) Ethyl 2-allyloxy-4-[N-(α-phenyl-2-piperidino-benzyl)-aminocarbonylmethyl]-benzoate Prepared from ethyl 2-hydroxy-4-[N-(α-phenyl-2-piperidino-benzyl)-aminocarbonylmethyl]-benzoate, using allyl bromide.

Yield: 46% of theory. M.p. 117–119° C. Calculated: C-74.97%; H-7.08%; N-5.47%. Found: C-74.90%; H-7.14%; N-5.38%.

(b) Ethyl 2-isopropoxy-4-[N-{1-(2-piperidino-phenyl)-1-butyl}-aminocarbonylmethyl]-benzoate Prepared from ethyl 2-hydroxy-4-[N-{1-(2-piperidino-phenyl)-1-butyl}-aminocarbonylmethyl]-benzoate, using 1.5 equivalents of isopropyl bromide at 150° C.

Yield: 56% of theory. M.p. 98–99° C. Calculated: C-72.47%; H-8.39%; N-5.83%. Found: C-72.60%; H-8.60%; N-5.75%.

(c) Ethyl 2-allyloxy-4-[N-{1-(2-piperidino-phenyl)-1-butyl}-aminocarbonylmethyl]-benzoate Prepared from ethyl 2-hydroxy-4-[N-{1-(2-piperidino-phenyl)-1-butyl}-aminocarbonylmethyl]-benzoate, using allyl bromide.

Yield: 72% of theory. M.p. 105–106° C. Calculated: C-72.77%; H-8.00%; N-5.85%. Found: C-72.90%; H-7.90%; N-5.87%.

(d) Ethyl 2-benzyloxy-4-[N-{1-(2-piperidino-phenyl)-1-butyl}-aminocarbonylmethyl]-benzoate Prepared from ethyl 2-hydroxy-4-[N-{1-(2-piperidino-phenyl)-1-butyl}-aminocarbonylmethyl]-benzoate, using benzyl bromide.

Yield: 80% of theory. M.p. 135–136° C. Calculated: C-74.97%; H-7.63%; N-5.30%. Found: C-75.20%; H-7.78%; H-5.59%.

EXAMPLE 9 n-Propyl 2-n-propoxy-4-[N-(α-phenyl-2-piperidino-benzyl)-aminocarbonylmethyl]-benzoate Prepared from 2-hydroxy-4-[N-(α-phenyl-2-piperidino-benzyl)-aminocarbonylmethyl]-benzoic acid analogous to Example 8, using 2 equivalents of sodium hydride and 2 equivalents of n-propyl bromide.

Yield: 45% of theory. M.p. 118–120° C. Calculated: C-74.97%; H-7.63%; N-5.30%. Found: C-75.20%; H-7.80%; N-5.41%.

The following compound was obtained by a procedure analogous to that described in Example 9:

(a) n-Propyl 2-n-propoxy-4-[N-{1-(2-piperidino-phenyl)-1-butyl}-aminocarbonylmethyl]-benzoate Prepared from n-propyl 2-hydroxy-4-[N-{1-(2-piperidino-phenyl)-1-butyl}-aminocarbonylmethyl]-benzoate.

Yield: 39% of theory. M.p. 89–90° C. Calculated: C-72.84%; H-8.56%; N-5.66%. Found: C-72.95%; H-8.77%; N-5.59%.

EXAMPLE 10

Ethyl 2-ethoxy-4-[N-(2-piperidino-benzyl)-aminocarbonylmethyl]-benzoate 1.0 g (2.18 mmols) of ethyl 2-ethoxy-4-[N-(5-chloro-2-piperidino-benzyl)-aminocarbonylmethyl]-benzoate was hydrogenated in 20 ml of ethanol with 0.5 g of 10% palladium-on-charcoal at 50° C. under 1 bar of hydrogen for 45 minutes. The reaction mixture was filtered through diatomaceous earths, the filtrate was evaporated in vacuo, and the residue was purified by colurin chromatography on silica gel (chloroform/methanol—10/1).

Yield: 0.71 g (77% of theory). M.p. 83–84° C. (from petroleum ether). Calculated: C-70.73%; H-7.60%; N-6.60%. Found: C-70.89%; H-7.66%; N-6.76%.

The following compound was obtained by a procedure analogous to that described in Example 10:

(a) Ethyl 2-ethoxy-4-[N-{1-(2-piperidino-phenyl)-1-propyl}-aminocarbonylmethyl]-benzoate Prepared from ethyl 2-ethoxy-4-[N-{1-(5-chloro-2-piperidino-phenyl)-1-propyl}-aminocarbonylmethyl]-benzoate.

Yield: 74% of theory. M.p. 115–117° C. Calculated: C-71.65%; H-8.02%; N-6.19%. Found: C-71.47%; H-8.11%; N-6.25%.

EXAMPLE 11

2-Ethoxy-4-[N-{1-(2-piperidino-phenyl)-3-methyl-1-butyl}-aminocarbonylmethyl]-benzoic acid (form A)

(a) 2-Ethoxy-4-[N-{1-(2-piperidino-phenyl)-3-methyl-1-buten-1-yl}-aminocarbonylmethyl]-benzoic acid.

Prepared from ethyl 2-ethoxy-4-[N-{1-(2-piperidino-phenyl)-3-methyl-1-buten-1-yl}-aminocarbonylmethyl]-benzoate.

Yield: 85% of theory. M.p. 110–113° C. Calculated: C-71.91%; H-7.61%; N-6.22%. Found: C-71.92%; H-7.80%; N-5.98%.

(b) 0.21 g (0.39 mmol) of 2-ethoxy-4-[N-{1-(2-piperidino-phenyl)-3-methyl-1-buten-1-yl}-aminocarbonylmethyl]-benzoic acid were hydrogenated in 10 ml of absolute ethanol with 0.10 g of 10% palladium-on-charcoal at 50° C. and a pressure of 1 bar of hydrogen for 7 hours. The reaction mixture was then filtered through diatomaceous earth, the reaction filtrate was evaporated in vacuo, and the residue was purified by column chromatography on silica gel (chloroform/methanol=10/1).

Yield: 0.10 g (47% of theory). M.p. 90–92° C.: (recrystallized from acetone/petroleum ether). Calculated: C-71.65%; H-8.02%; N-6.19%. Found: C-71.50%; H-8.12%; N-6.45%.

2-Ethoxy-4-[N-{1-(2-piperidino-phenyl)-3-methyl-1-butyl}-aminocarbonylmethyl]-benzoic acid, is also obtained in other solid forms when it is crystallized from other solvents or mixtures of solvents. Form (B), which has a melting point of 140 to 142° C., is obtained by crystallization from an ethanol/water mixture. The foamy form (C), which has a melting point range from 75 to 85° C., is obtained from the 1:1 methanol adduct (melting point: 85 to 90° C.), which occurs upon cyrstallization from methanol, by heating at 60° C. in vacuc (5 Torr) over phosphorus pentoxide, whereby the methanol is removed.

Figure 1B:
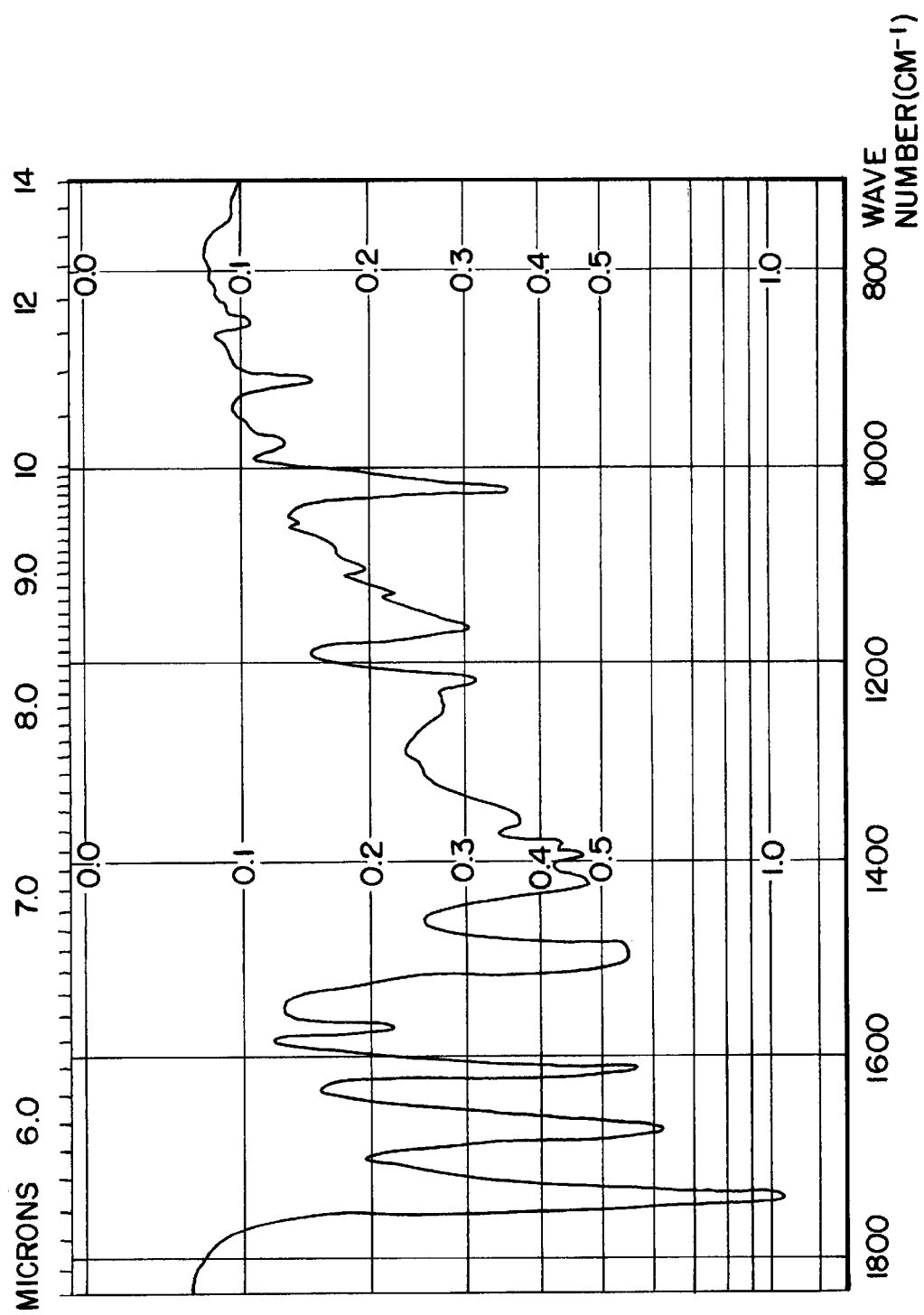
Figure 2A:
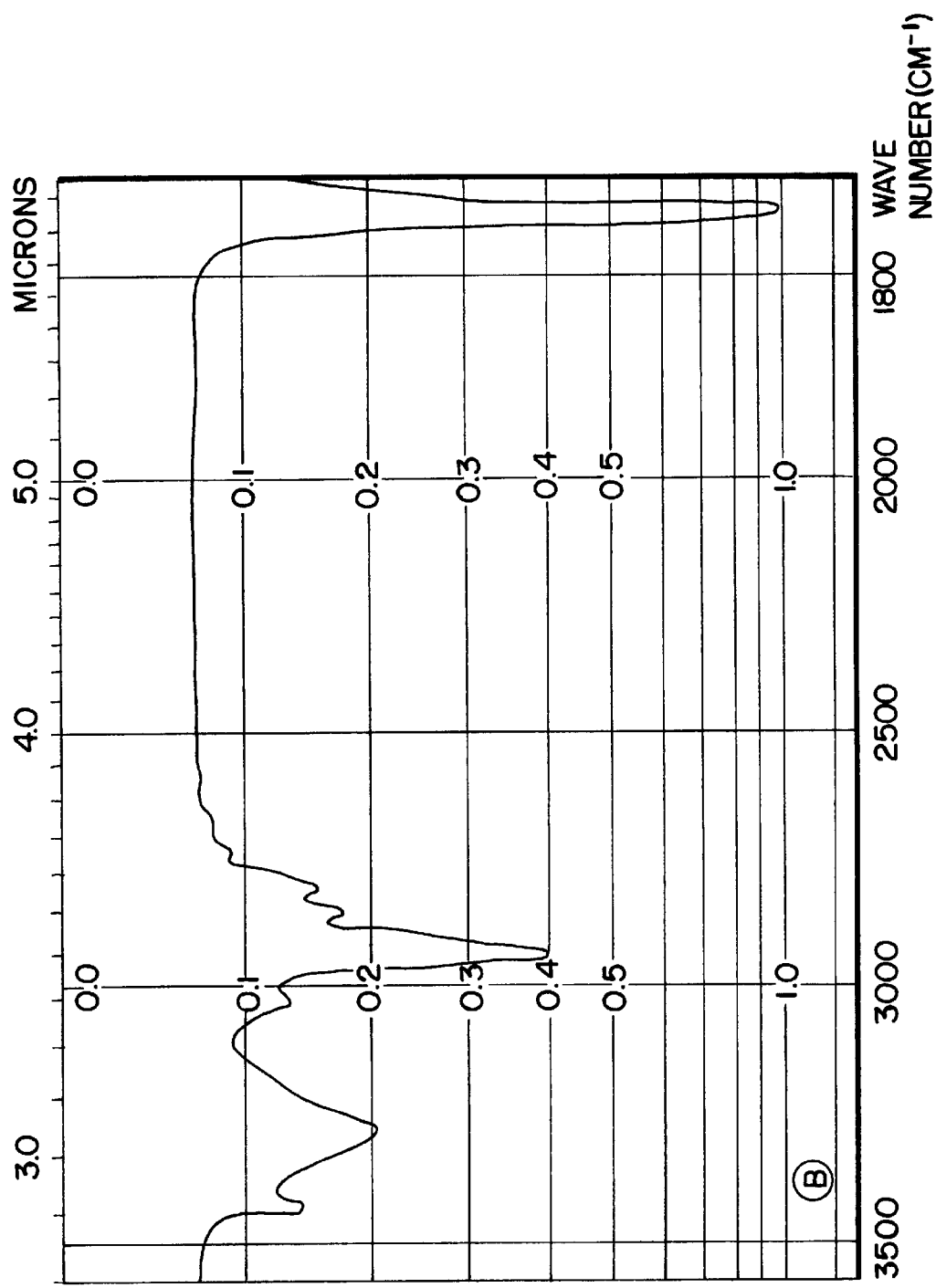
FIG. 2: 2-Ethoxy-4-[N-{1-(2-piperidino-phenyl)-3-methyl-1-butyl}-aminocarbonylmethyl]-benzoic acid (form B); dissolved in methylene chloride (IR)
Figure 2B:
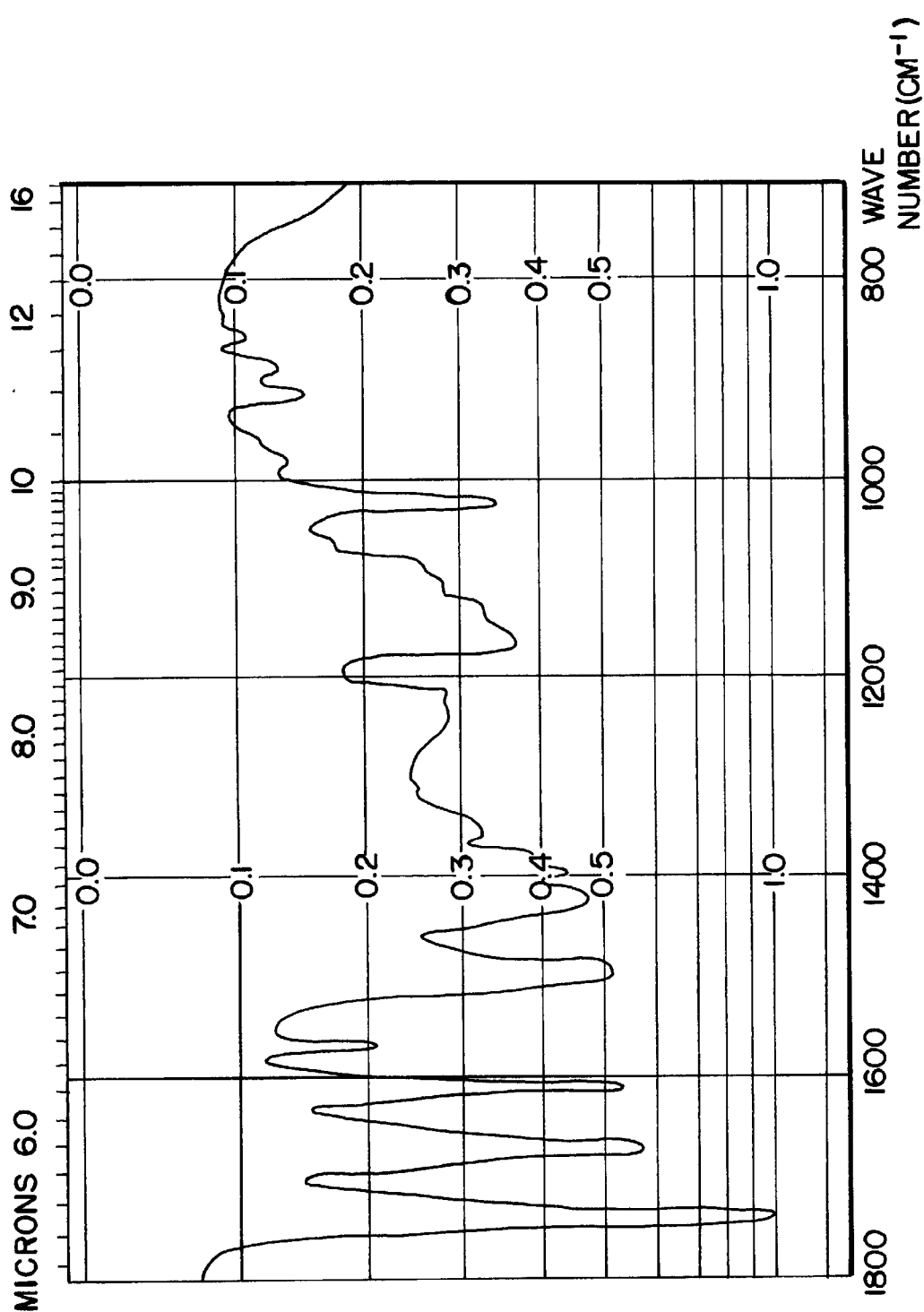
Figure 3A:
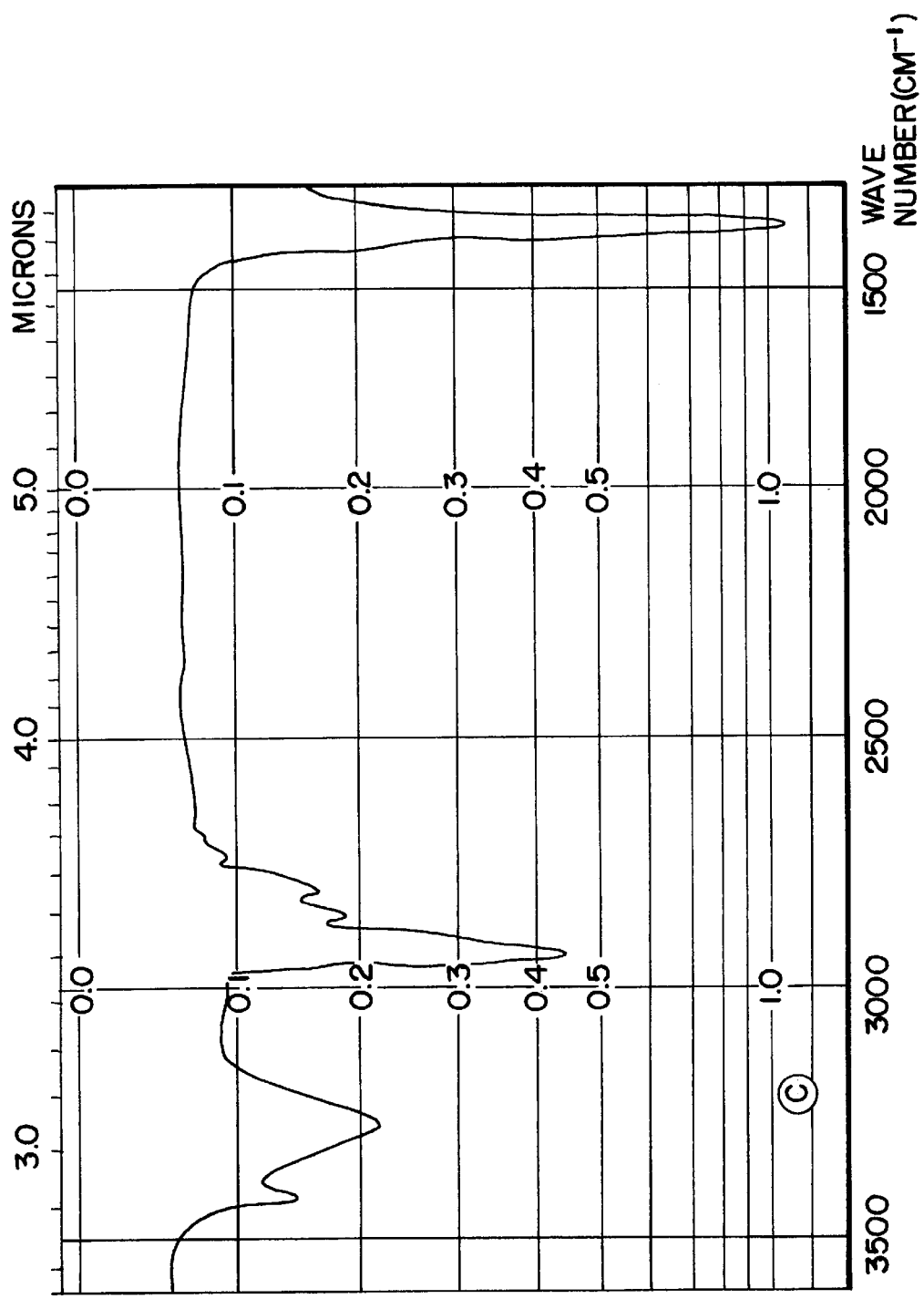
FIG. 3: 2-Ethoxy-4-[N-{1-(2-piperidino-phenyl)-3-methyl-1-butyl}-aminocarbonylmethyl]-benzoic acid (form C); dissolved in methylene chloride (IR)
Figure 3B:
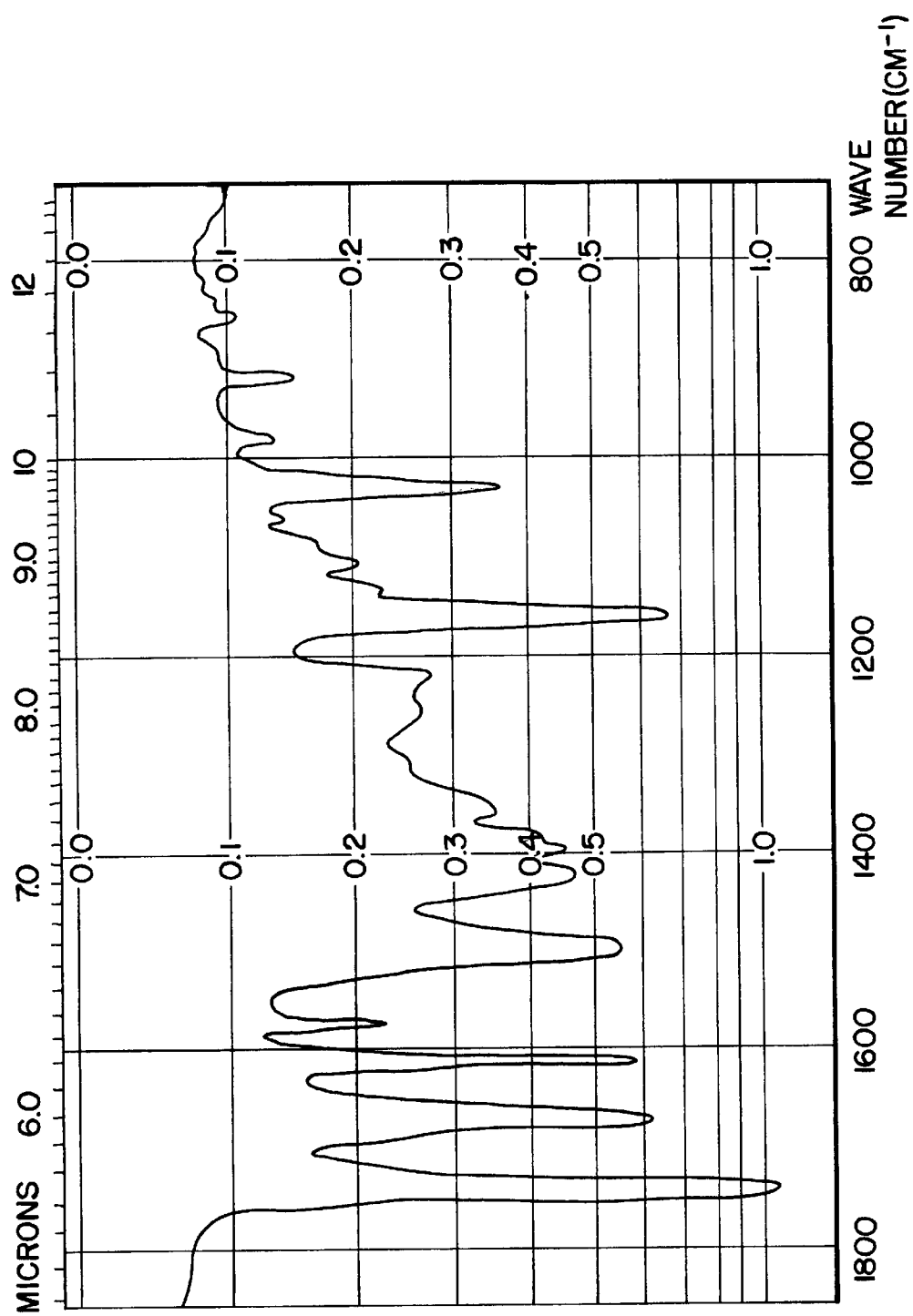
Figure 4A:
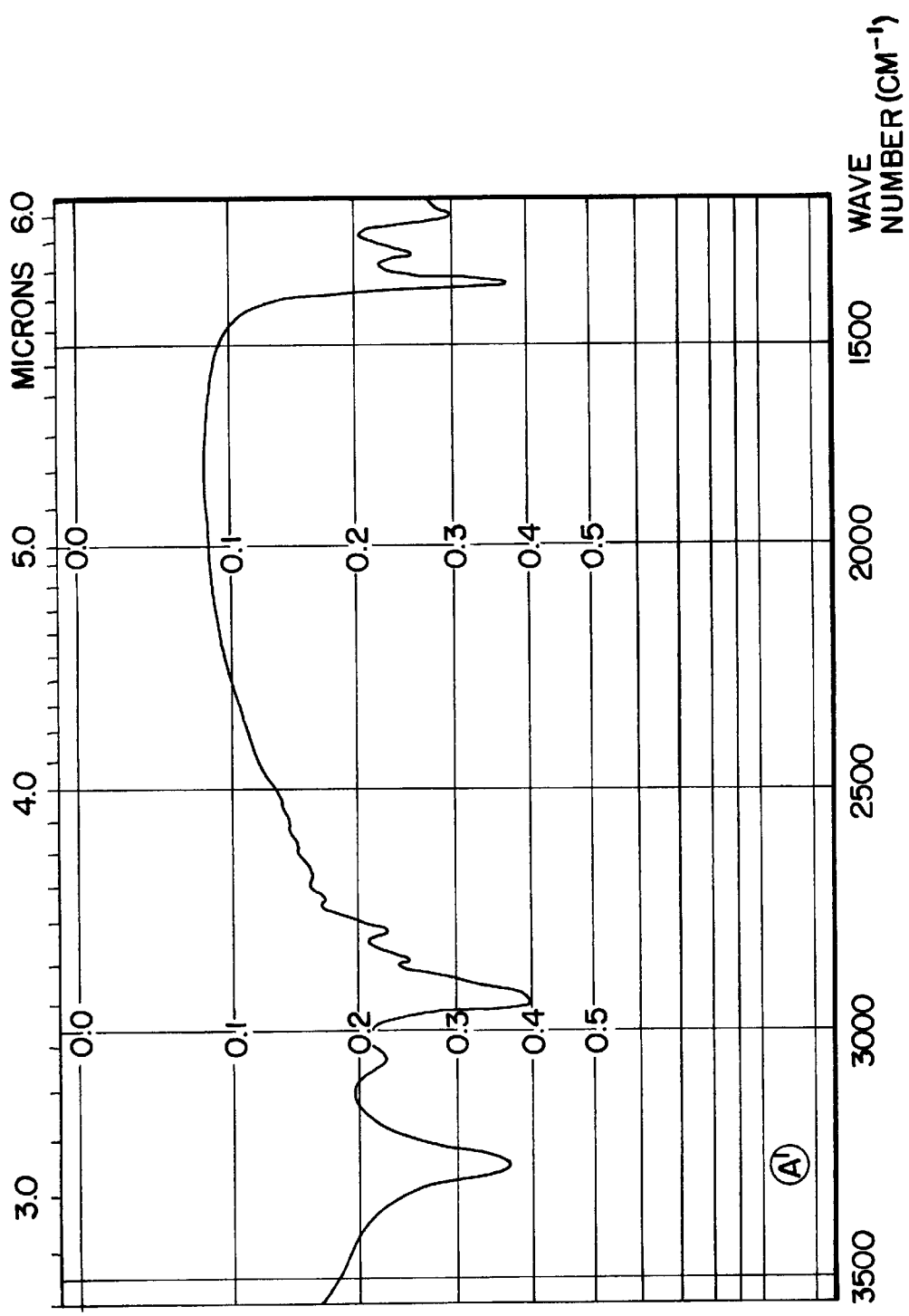
FIG. 4: 2-Ethoxy-4-[N-{1-(2-piperidino-phenyl)-3-methyl-1-butyl}-aminocarbonylmethyl]-benzoic acid (form A); solid form (IR)
Figure 4B:
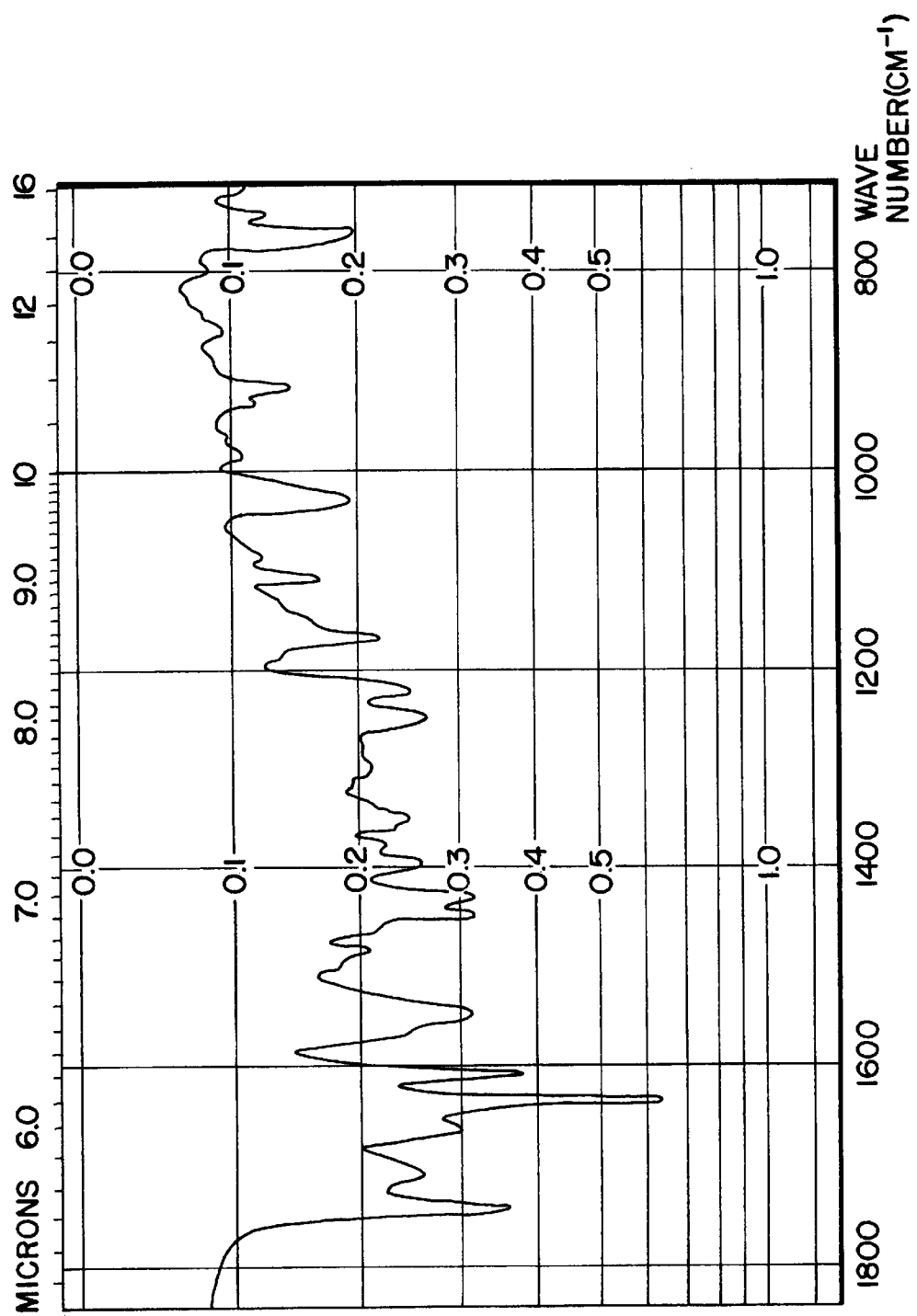
Figure 5A:
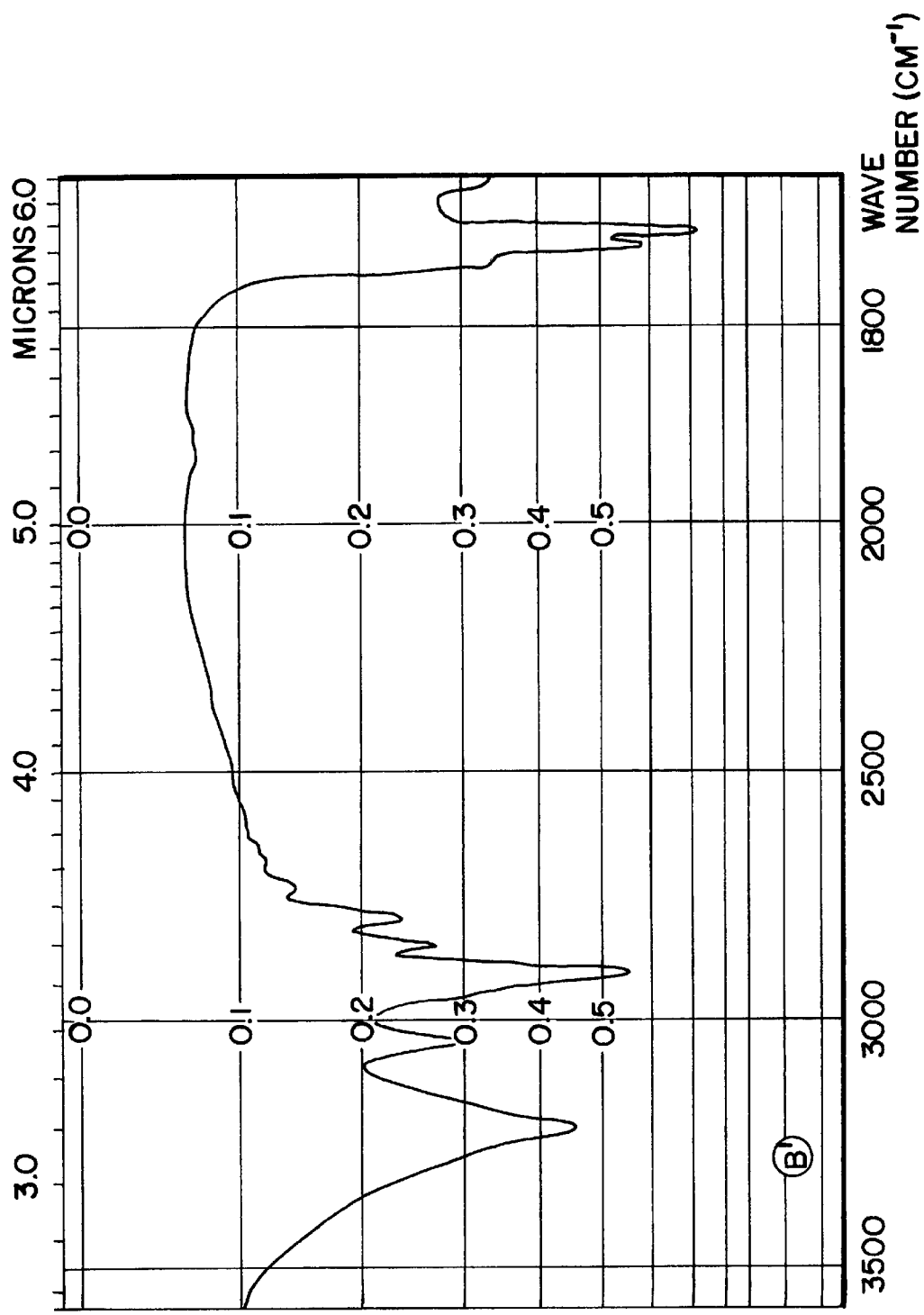
FIG. 5: 2-Ethoxy-4-[N-{1-(2-piperidino-phenyl)-3-methyl-1-butyl}-aminocarbonylmethyl]-benzoic acid (form B); solid form (IR)
Figure 5B:
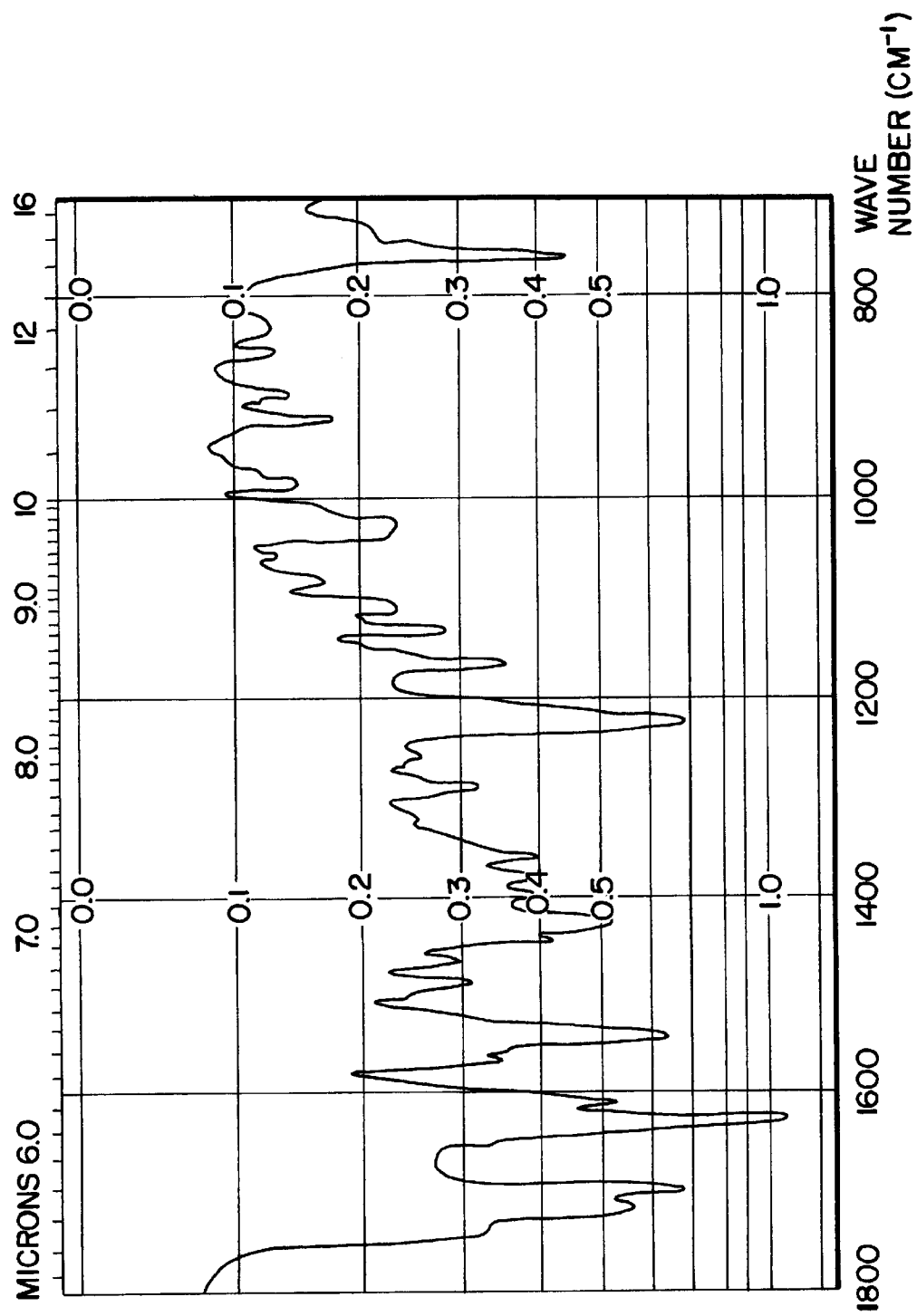
Figure 6A:
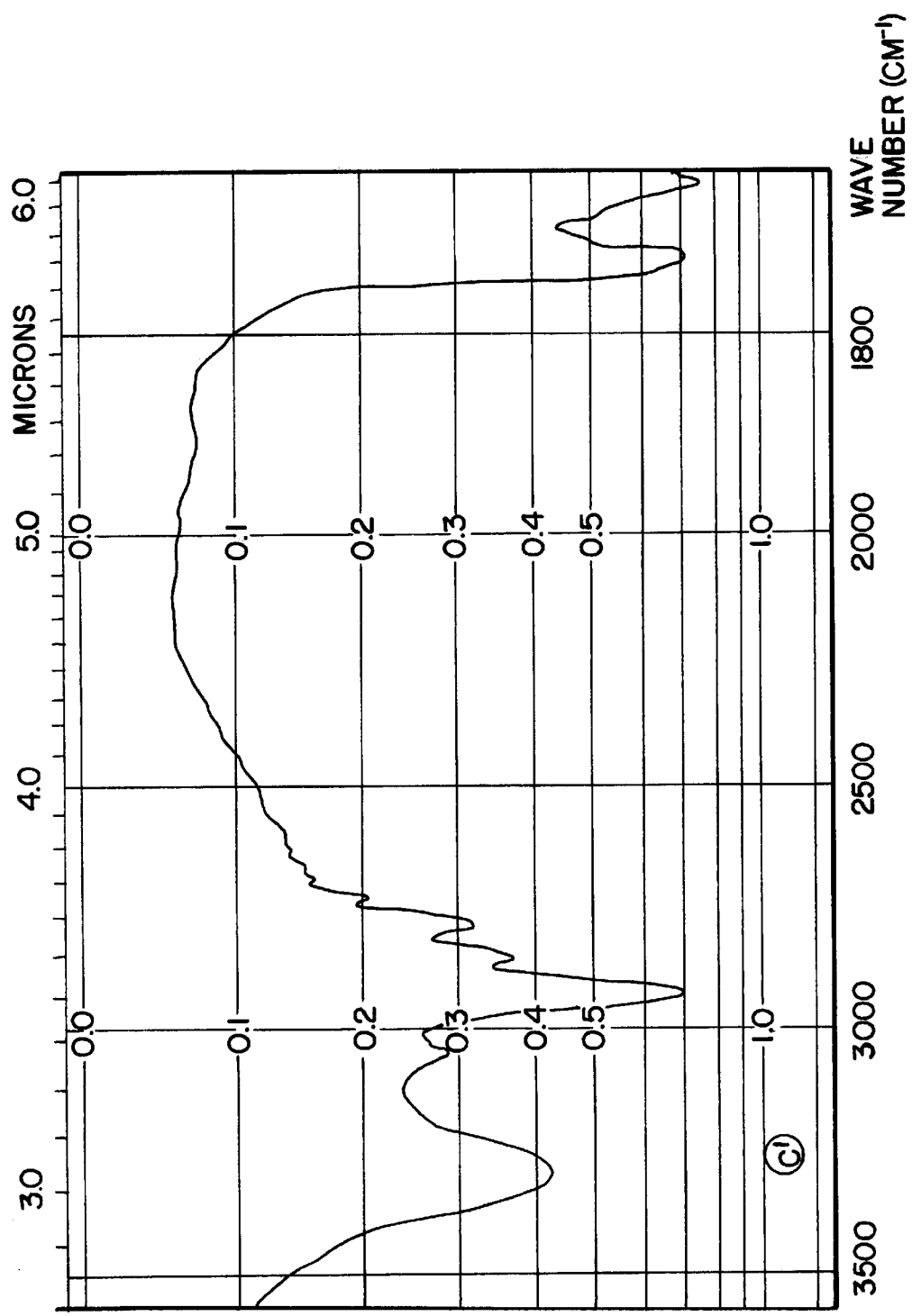
FIG. 6: 2-Ethoxy-4-[N-{1-(2-piperidino-phenyl)-3-methyl-1-butyl}-aminocarbonylmethyl]-berizoic acid (form C); solid form (IR)
Figure 6B:
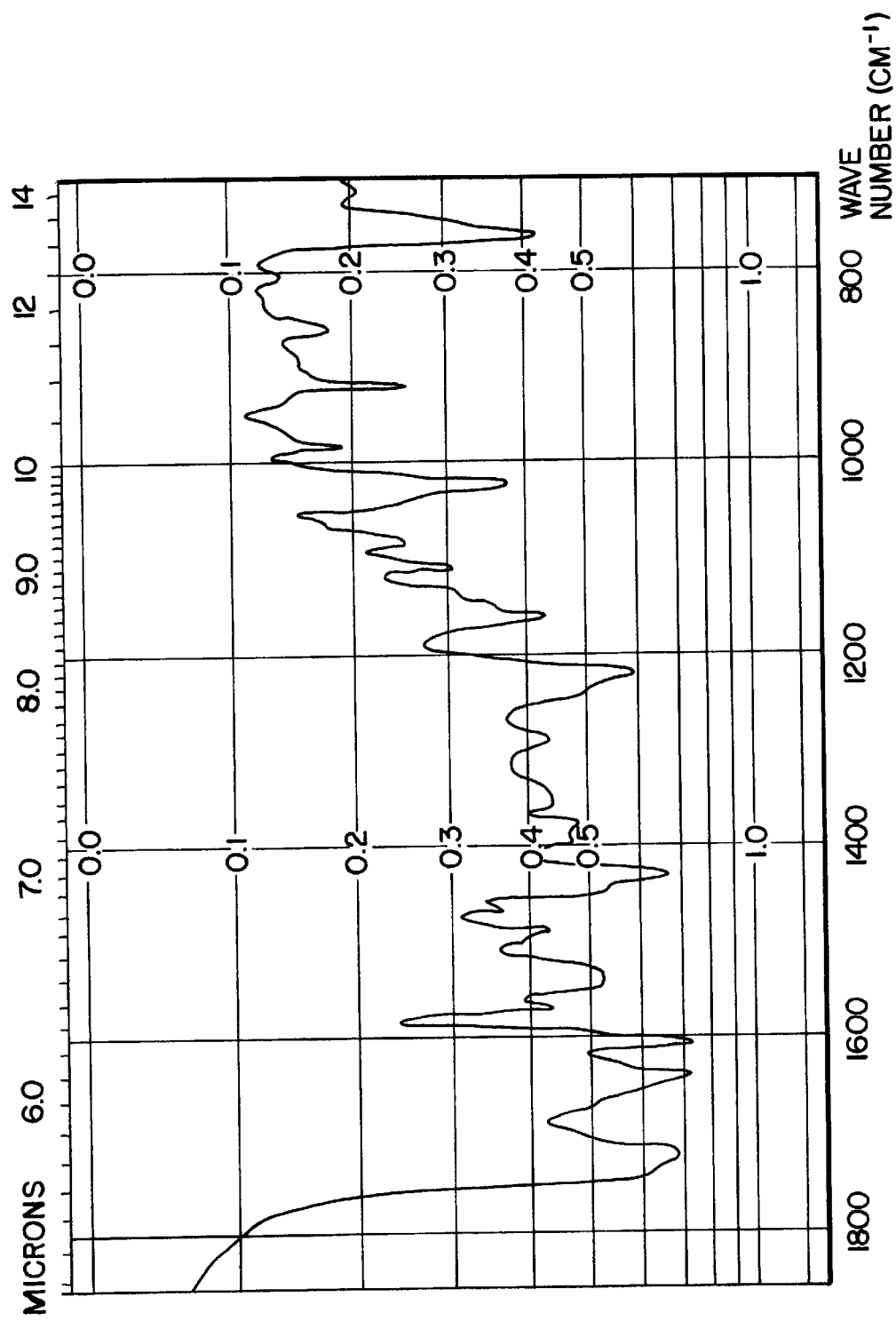

In the dissolved state these forms are identical, as is evident from the corresponding solution spectra, for instance the IR-spectra in methylene chloride shown in FIGS. 1, 2 and 3 of the attached drawings. However, in the solid state, the three forms differ in their melting characteristics and their solid spectra, for instance as shown by the corresponding IR-KBr-spectra in FIGS. 4, 5 and 6 of the attached drawings.

In order to measure infra-red absorption, forms (A), (B) and (C) were dissolved in methylene chloride (40 mg of substance per ml of methylene chloride), or intimately triturated with potassium bromide and then compressed hydraulically to form a tablet (approx. 1 mg of substance/300 mg of KBr).

In the case of the solutions, the IR-spectra were measured with an IR-spectrometer (Perkin Elmer Tyoe 299) in a cell of sodium chloride (layer thickness 0.2 mm) by comparison with a pure methylene chloride solution and, in the case of the potassium bromide tablets, with an IR-spectrometer (Perkin Elmer Type 298) by comparison with air.

The three solid forms can be converted into one another by suitable recrystallization and drying. Thus, the lowmelting-point form (A) is obtained by recrystallizing the high-melting-point form (B) from acetone/petroleum ether and the high-melting-point form (B) is obtained by recrystallizing the low-melting-point form (A) from ethanol/water. By recrystallizing the high-melting-point form (B) from methanol, a 1:1 adduct with methanol is obtained, and from this the foamy form (C) is obtained by removing the methanol.

Irrespective of the particular process which is used to synthesize 2-Ethoxy-4-[N-{1-(2-piperidino-phenyl)-3-methyl-1-butyl}-aminocarbonylmethyl]-benzoic acid, therefore, the high-melting-point or low-melting-point or foamy form can be obtained, as desired, by a suitable choice of solvent or mixture of solvents during crystallization and by suitable drying. This is important in the practical use of the solid forms, whether or not they are accompanied by galenic excipient in pharmaceutical compositions, particularly for lowering blood sugar in the treatment of Type II diabetes; this is because different solid forms may have different shelf lives and/or different absorption characteristics in vivo and may thus give a different pattern of biological activity.

2-Ethoxy-4-[N-{1-(2-piperidino-phenyl)-3-methyl-1-butyl}-aminocarbonylmethyl]-benzoic acid may be obtained by the methods described hereinabove, but preferably by reacting 3-methyl-1-(2-piperidino-phenyl)-1-butylamine with a compound of the formula

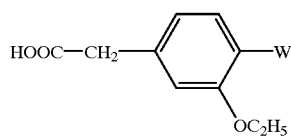

(XI)

wherein W is carboxyl or carboxyl protected by a protective group or with a reactive derivative thereof, optionally prepared in the reaction mixture, followed, if necessary, by removal of the protective group, and the solid forms (B) and (C) are obtained by suitable subsequent crystallization, suitable final recrystallization and/or drying.

Examples of reactive dreivatives of a compound of the formula XI include the esters such as the methyl, ethyl and benzyl esters thereof, the thioesters such as the methylthio and ethylthioesters, the halides such as the acid chloride, the anhydrides and imidazolides thereof.

The reaction is advantageously carried out in a solvent such as methylene chloride, chloroform, carbon tetrachloride, ether, tetrahydrofuran, dioxane, benzene, toluere, acetonitrile or dimethylformamide, optionally in the presence of an acid-activating agent or a dehydrating agent, for instance in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole, N,N'-thionyldiimidazole or triphenylphosphine/carbon tetrachloride, or in the presence of an amino group activating agent, such as phosphorus trichloride and optionally in the presence of an inorganic base such as sodium carbonate or a tertiary organic base such as triethylamine or pyridine, which may simultaneously serve as solvent, at temperatures between −25 and 250° C., but preferably at temperatures between −10° C. and the boiling point of the solvent which is used. The reaction may also be carried out without a solvent, and any water formed during the reaction may be removed by azeotropic distillation, for instance by heating with toluene, using a water trap, or by adding a drying agent such as magnesium sulfate or a molecular sieve.

The subsequent removal of the protective group is preferably carried out by hydrolysis, either in the presence of an acid such as hydrochloric, sulfuric, phosphoric or trichloroacetic acid, or in the presence of a base such as sodium hydroxide or potassium hydroxide, in a suitable solvent such as water, methanol, methanol/water, ethanol, ethanol/water water, water/isopropanol or water/dioxane at temperatures between −10 and 120° C., for instance at temperatures between room temperature and the boiling point of the reaction mixture.

A tert.butyl protective group may also be removed thermally, optionally in an inert solvent such as methylene chloride, chloroform, benzene, toluene, tetrahydrofuran or dioxane, and preferably in the presence of a catalytic quantity of an acid such as p-toluenesulfonic, sulfuric, phosphoric or polyphosphoric acid.

Moreover, a benzyl protective group may also be remove, by hydrogenation in the presence of a hydrogenation catalyst such as palladium-on-charcoal in a suitable solvent such as methanol, ethanol, ethanol/water, glacial acetic acid, ethyl acetate, dioxane or dimethylformamide.

The subsequent crystallization is carried out in situ from the reaction mixture containing ethanol/water or, as a final recrystallization, by dissolving the reaction product in a mixture of ethanol and water, optionally while heating, and cooling, optionally accompanied by trituration and/or seeding (form B), or by dissolving the reaction product in acetone and adding petroleum ether (form A), or by dissolving the reaction product, optionally while heating in methanol, subsequent cooling of the solution accompanied by trituration and/or seeding, and heating the isolated solid methanol adducts preferably in vacuo, in the presence of a drying agent such as phosphorus pentoxide (form C).

Like the other compounds of the formula I, solid forms (A), (B) and (C) of 2-Ethoxy-4-[N-{1-(2-piperidino-phenyl)-3-methyl-1-butyl}-aminocarbonylmethyl]-benzoic acid may also be converted into their salts, particularly their non-toxic, pharmacologically acceptable table salts with inorganic or organic acids or bases. Suitable acids for this purpose are, for example, hydrochloric, hydrobromic, sulfuric, phosphoric, lactic, citric, trataric, succinic, maleic or fumaric acid, and suitable bases are sodium hydroxide, potassium hydroxide, calcium hydroxide, cyclohexylamine, ethanolamine, diethanolam triethanolamine, ethylenediamine or lysine.

The melting points in Examples 12–16 were determined in an Electrothermal® melting point apparatus with visual observation of the sample of product in a capillary tube fused at one end.

EXAMPLE 12

Ethyl 2-ethoxy-4-[N-{1-(2-piperidino-phenyl)-3-methyl-1-butyl}-aminocarbonylmethyl]-benzoate 3 g (11.9 mmols) of 3-ethoxy-4-ethoxycarbonyl-phenylacetic acid, 3.7 g (14.3 mmols) of triphenylphosphine, 3.3 ml (23.8 mmols) of triethylamine and 1.15 ml (11.9 mmols) of carbon tetrachloride were added successively to a solution of 2.9 g (11.9 mmols) of 3-methyl-1-(2-piperidino-phenyl)-1-butylamin in 29 ml of acetonitrile. The mixture was then stirred for 15 hours at room temperature, the solvent was removed in vacuo, and the residue was taken up in a mixture of ethyl acetate and water. The organic phase was dried over sodium sulfate, filtered and concentrated by evaporation in vacuo. The evaporation residue was purified by column chromatography on silaca gel (toluene/acetone=10/1).

Yield: 4.9 g (85% of theory). M.p. 143–145° C. (petroleum ether). Calculated: C-72.47%; H-8.39%; N-5.83%. Found: C-72.37%; H-8.45%; N-6.07%.

EXAMPLE 13

High-melting-point form (B) of 2-ethoxy-4-[N-{1-(2-piperidino-phenyl)-3-methyl-1-butyl}-aminocarbonylmethyl]-benzoic acid A mixture of 4.7 g (9.7 mmols) of ethyl 2-ethoxy-4-[(N-{1-(2-piperidino-phenyl)-3-methyl-1-butyl)-aminocarbonylmethyl]-benzoate and 14.7 ml of 1N sodium hydroxide was stirred in 47 ml of ethanol for 2 hours at 60° C., then neutralized with 14.7 ml of 1N hydrochloric acid and cooled to 0° C. The mixture was filtered to remove the precipitated colorless cyrstals, and the crystals were washed with ice water and with a little ice cold ethanol and then dried at 100° C./1 Torr.

Yield: 3.9 g (88% of theory). M.p. 140–142° C. Calculated: C-71.65%; H-8.02%; N-6.19%. Found: C-71.90%; H-8.08%; N-6.34%.

Upon further recrystallization from ethanol/water (2/1) the melting point remained constant.

EXAMPLE 14

Low-melting-point form (A) of 2-ethoxy-4-[N-{1-(2-piperidino-phenyl)-3-methyl-1-butyl}-aminocarbonylmethyl]-benzoic acid 1.0 g of the high-melting-point form (B) of 2-ethoxy-4-[N-{1-(2-piperidino-phenyl)-3-methyl-1-butyl}-aminocarbonylmethyl]-benzoic acid was dissolved at room temperature in 5 ml of acetone, and 5 ml of petroleum ether (m.p. 60–70° C.) were added. Upon trituration, crystallization gradually set in. The same quantity of petroleum ether was added again, and after crystallization had ended, the mixture was filtered. The crystals were washed with petroleum ether, and the almost colorless crystals were dried for 2 hours at 60° C./0.1 Torr.

Yield: 0.7 g. M.p. 95–98° C. (clear beginning at 135° C.). Calculated: C-71.65%; H-8.02%; N-6.19%. Found: C-71.80%; H-8.04%; N-5.92%.

The IR-spectra for this form (see FIGS. 1 and 4) are identical to the IR-spectra for the form (A), melting point 90–92° C., described in Example 11(b) above.

EXAMPLE 15

High-melting-point form (B) of 2-ethoxy-4-[N-{1-(2-piperidino-phenyl)-3-methyl-1-butyl}-aminocarbonylmethyl]-benzoic acid 1.0 g of the low-melting-point form (A) of 2-ethoxy-4-[N-{1-(2-piperidino-phenyl)-3-methyl-1-butyl}-aminocarbonylmethyl[-benzoic acid was dissolved in 10 ml of ethanol/water (2/1) while heating over a steam bath. The solution was then cooled to 0° C., whereupon crystallization began. The mixture was filtered, and the residue was washed with a little ice-cold ethanol and dried at 100° C./1 Torr.

Yield: 0.8 g. M.p. 140–142° C.

EXAMPLE 16

Foamy form (C) of 2-ethoxy-4-[N-{1-(2-piperidino-phenyl)-3-methyl-1-butyl}-aminocarbonylmethyl]-benzoic acid 1.5 g of the high-melting-point form (B) of 2-ethoxy-4-[N-{1-(2-piperidino-phenyl)-3-methyl-1-butyl}-aminocarbonylmethyl]-benzoic acid was dissolved in 5 ml of methanol while heating. The solution was then cooled to 0° C. with trituration. The crystals precipitated thereby were separated by filtration, washed with a little cold methanol, and dried for 2 hours at 60° C./0.1 Torr.

Yield of adduct (with 1×CH$_3$OH): 1.2 g. M.p. 85–90° C. Calculated: (×1° CH 3OH): C-69.39%; H-8.32%; N-5.78%. Found: C-69.20%; H-8.20%; N-5.92%.

The adduct was converted into the methanol-free foamy form (C) by heating for 24 hours at 60° C./5 Torr over phosphorus pentoxide. Melting range: 75–85° C. Calculated: C-71.65%; H-8.02%; N-6.19%. Found: C-71.82%; H-8.06%; N-6.03%.

EXAMPLE 17

Ethyl 2-ethoxy-4-[N-{1-(2-piperidino-phenyl)-3-methyl-1-butyl}-aminocarbonylmethyl]-benzoate Prepared from ethyl 2-ethoxy-4-[N-{1-(2-piperidino-phenyl)-3-methyl-1-buten-1-yl}-aminocarbonylmethyl]-benzoate, melting point 125–126° C., which in turn was prepared from (2-piperidino-phenyl)-isobutyl-ketimine and 3-ethoxy-4-ethoxycarbonyl-phenyl-acetic acid analogous to Example 1.

Yield: 51% of theory. M.p. 139–141° C. Calculated: C-72.47%; H-8.39%; N-5.83%. Found: C-72.30%; H-8.20%; N-5.87%.

EXAMPLE 18

2-Ethoxy-4-[N-(α-phenyl-2-piperidino-benzyl)-aminocarbonylmethyl]-benzyl alcohol A solution of 1.8 g (3.6 mmols) of ethyl 2-ethoxy-4-[N-(α-phenyl-2-piperidino-benzyl)-aminocarbonylmethyl]-benzoate in 20 ml of absolute tetrahydrofuran was added dropwise at −5° C. to a mixture of 0.28 g (7.4 mmols) of lithium aluminum hydride and 50 ml of absolute tetrahydrofuran, and the resulting mixture was stirred for 3 hours at 0° C. It was then diluted with absolute ether, and 4N sodium hydroxide was added. The mixture was filtered through diatomaceous earth, the filtrate was evaporated in vacuo, and the residue was purified by column chromatography on silica gel (toluene/ethyl acetate=2/1).

Yield: 0.51 g (31% of theory). M.p. 133–135° C. Calculated: C-75.95%; H-7.47%; N-6.11%. Found: C-75.97%; H-7.55%; N-5.95%.

The following compound was obtained by a procedure analogous to that described in Example 18:

(a) 2-Ethoxy-4-[N-{1-(2-piperidino-phenyl)-1-butyl}-aminocarbonylmethyl]-benzyl alcohol Prepared from ethyl 2-ethoxy-4-[N-{1-(2-piperidino-phenyl)-1-butyl}-aminocarbonylmethyl]-benzoate by reduction with lithium borohydride in boiling tetrahydrofuran in the presence of 10% of trimethyl borate.

Yield: 68% of theory. M.p. 112–115° C. Calculated: C-73.55%; H-8.55%; N-6.60%. Found: C-73.60%; H-8.38%; N-6.69%.

EXAMPLE 19

2-Ethoxy-4-[N-(α-phenyl-2-piperidino-benzyl)-amino-carbonylmethyl]-benzaldehyde

A solution of 0.4 g (0.87 mmol) of 2-ethoxy-4-[N-(α-phenyl-2-piperidino-benzyl)-aminocarbonylmethyl]-benzyl alcohol was added dropwise at room temperature to a stirred solution of 0.28 g (1.3 mmols) of pyridinium chlorochromate in 5 ml of chloroform. The reaction mixture was stirred overnight at room temperature, evaporated in vacuo, the residue was mixed with ether, the etheral mixture was filtered the filtrate was evaporated in vacuo, and the residue was purified by column chromatography on silica gel (toluene/ethyl acetate=2/1).

Yield: 0.16 g (40% of theory). M.p. 154–156° C. Calculated: C-76.29%; H-7.06%; N-6.14%. Found: C-76.30%; H-7.15%; N-6.10%.

The following compound was obtained by a procedure analogous to that described in Example 19:
(a) 2-Ethoxy-4-[N-{1-(2-piperidino-phenyl)-1-butyl}-aminocarbonylmethyl]-benzaldehyde Prepared from 2-ethoxy-4-[N-{1-(2-piperidino-phenyl)-1-butyl}-aminocarbonylmethyl]-benzyl alcohol.

Yield: 47% of theory. M.p. 109–111° C. Calculated: C-73.90%; H-8.11%; N-6.63%. Found: C-74.22%; H-8.14%; N-6.73%.

EXAMPLE 20

2-Ethoxy-4-[N-(α-phenyl-2-piperidino-benzyl)-aminocarbonylmethyl-benzaldehyde 0.67 g (5.6 mmols) of sodium carbonate was heated together with 6 ml of ethylene glycol on an oil bath at 170° C., and then, while rapidly stirring, 0.70 g (1.1 mmols) of $N^1$-[2-ethoxy-4-{N-(α-phenyl-2-piperidino-benzyl)-aminocarbonylmethyl}-benzoyl]-$N^2$-tosyl-hydrazine were added thereto within a minute; a violent evolution of gas was observed. Then, the mixture was heated for 2 minutes more at 170° C. and then poured immediately over ice. The aqueous mixture was extracted with ether, and the extract was dried, filtered and evaporated in vacuo. The evaporation residue was purified by column chromatography on silica gel (toluene/ethyl acetate=2/1).

Yield: 0.25 g (50% of theory). M.p. 153–156° C. Calculated: C-76.29%; H-7.06%; N-6.14%. Found: C-76.42%; H-7.33%; N-6.28%.

The following compound was obtained by a procedure analogous to that described in Example 20:
(a) 2-Ethoxy-4-[N-{1-(2-piperidino-phenyl)-1-butyl}-aminocarbonylmethyl]-benzaldehyde Prepared from $N^1$-[2-ethoxy-4-[N-{1-(2-piperidino-phenyl)-1-butyl}-aminocarbonylmethyl]-benzoyl]-$N^2$-tosyl-hydrazine.

Yield: 51% of theory. M.p. 108–111° C. Calculated: C-73.90%; H-8.11%; N-6.63%. Found: C-73.79%; H-8.29%; N-6.75%.

EXAMPLE 21

Benzyl 2-ethoxy-4-[N-{1-(2-piperidino-phenyl)-1-butyl}-aminocarbonylmethyl]-benzoate 0.35 g (0.8 mnol) of 2-ethoxy-4-[N-{1-(2-piperidino-phenyl)-1-butyl}-aminocarbonylmethyl]-benzoic acid was refluxed together with 0.15 g (0.9 mmol) of N,N'-carbonyldiimidazole in 15 ml of absolute tetrahydrofuran for 2 hours. Then, 1.03 ml (10 mmols) of benzyl alcohol were added, and the mixture was refluxed for 3.5 hours. The reaction mixture was then evaporated in vacuo, and the residue was purified by column chromatography on silica gel (chloroform/acetone=9/1).

Yield: 0.10 g (23.6% of theory). M.p. <20° C. Calculated: Mol peak m/e=528. Found: Mol peak m/e=528.

EXAMPLE 22

Ethyl (+)-2-ethoxy-4-[N-{1-(2-piperidino-phenyl)-1-butyl}-aminocarbonylmethyl]-benzoate and Ethyl (−)-2-ethoxy-4-[N-{1-(2-piperidino-phenyl)-1-butyl}-aminocarbonylmethyl]-benzoate 28 mg of ethyl (±)-2-ethoxy-4-[N-{1-(2-piperidino-phenyl)-1-butyl}-aminocarbonylmethyl]-benzoate were added in 0.02 mg-portions to a chiral phase HPLC column made by the Baker Co., in which (R)-N-3,5-dinitrobenzoyl-phenylglycine was covalently bonded to aminopropyl-silica gel (5 μm particle size, spherical, pore size 60 Å; 4.6 mm internal diameter, 25 cm in length).

Flow agent: hexane/ethanol=100/5. Flow rate: 0.75 ml/minute. Temperature: 22° C.

The fractions eluted at 31.2 minutes and at 32.9 minute (UV detection at 254 nm) were separately recovered, collected and evaporated in vacuo.

The following was obtained from the 31.2-minute eluate:
7.5 mg of ethyl (+)-2-ethoxy-4-[N-{1-(2-piperidino-phenyl)-1-butyl}-aminocarbonylmethyl]-benzoate.

M.p. 117–119° C. Specific rotation: $[α]_D^{20}$=+7.0° (c=1.03 in methanol).

The following was obtained from the 32.9-minute eluate:
9.4 mg of ethyl (−)-2-ethoxy-4-[N-{1-(2-piperidino-phenyl)-1-butyl}-aminocarbonylmethyl]-benzoate.

m.p. 115–117° C. Specific rotation: $[α]_D^{20}$=−6.9° (c=1.02 in methanol).

Analogous to Example 22,
(a) Ethyl (±)-2-ethoxy-4-[N-(α-phenyl-2-piperidino-benzyl)-aminocarbonylmethyl]-benzoate
was separated into its (+) enantiomer and its (−) enantiomer.

EXAMPLE 23

Ethyl 2-acetoxy-4-[N-{1-(2-piperidino-phenyl)-1-butyl}-amino-carbonylmethyl]-benzoate A mixture of 0.20 g (0.46 mmol) of ethyl 2-hydroxy-4-[N-{1-(2-piperidino-phenyl)-1-butyl}-aminocarbonylmethyl]-benzoate, 0.34 ml (3.65 mmols) of acetic acid anhydride and 20 μl of concentrated sulfuric acid was stirred for 40 hours at 70° C. The mixture was then evaporated in vacuo, the residue was taken up in a mixture of water and ether, and neutralized with sodium carbonate. The etheral phase was separated, and the aqueous phase was extracted twice with ethyl acetate. The combined organic extracts were dried, filtered and evaporated in vacuo. The evaporation residue was purified by column chromatography on silica gel (toluene/acetone=10/1).

Yield: 50% of theory. M.p. 133–135° C. (from petroleum ether). Calculated: C-69.98%; H-7.55%; N-5.83%. Found: C-69.75%; H-7.32%; N-5.74%.

The following compounds were obtained by a procedure analogous to that described in Example 23:
(a) 2-Acetoxy-4-[N-{1-(2-piperidino-phenyl)-1-butyl}-amino-carbonylmethyl]-benzoic acid Prepared from 2-hydroxy-4-[N-{1-(2-piperidino-phenyl)-1-butyl}-aminocarbonylmethyl]-benzoic acid.

Yield: 12% of theory. M.p. 125–127° C. Calculated: Mol peak m/e=452. Found: Mol peak m/e=452.
(b) Ethyl 2-acetoxy-4-[N-(α-phenyl-2-piperidino-benzyl)-aminocarbonylmethyl]-benzoate Prepared from ethyl 2-hydroxy-4-[N-(α-phenyl-2-piperidino-benzyl)-aminocarbonylmethyl]-benzoate.

Yield: 23.5% of theory. M.p. 163–166° C. Calculated: C-72.35%; H-6.66%; N-5.44%. Found: C-72.41%; H-6.75%; N-5.31%.
(c) 2-Acetoxy-4-[N-(α-phenyl-2-piperidino-benzyl)-aminocarbonylmethyl]-benzoic acid Prepared from 2-hydroxy-4-[N-(α-phenyl-2-piperidino-benzyl)-aminocarbonylmethyl]-benzoic acid.

Yield: 17% of theory. M.p. 126–128° C. Calculated: C-71.58%; H-6.21%; N-5.76%. Found: C-71.77%; H-6.57%; N-5.81%.

EXAMPLE 24

2-Ethoxy-4-[N-{1-(2-piperidino-phenyl)-1-butyl}-aminocarbonylmethyl]-toluene

A mixture of 0.54 g (1.2 mmols) of 2-ethoxy-4-[N-{1-(2-piperidino-phenyl)-1-butyl}-aminocarbonylmethyl]-benzyl chloride (melting point 114–115° C., prepared from 2-ethoxy-4-[N-{1-(2-piperidino-phenyl)-1-butyl}-aminocarbonylmethyl-be alcohol and thionyl chloride in chloroform) and 10 ml of absolute dioxane was hydrogenated for 3 hours at 20° C. and a pressure of 5 bar hydrogen. The reaction mixture was then evaporated in vacuo, and the residue was taken up in a mixture of ethyl acetate and aqueous sodium carbonate. The organic phase was dried, filtered and evaporated in vacuo. The evaporation residue was purified by column chromatography on silica gel (chloroform/acetone=19/1).

Yield: 0.23 g (47% of theory). M.p. 107–108° C. Calculated C-76.43%; H-8.88%; N-6.86%. Found: C-76.40%; H-8.88%; N-6.90%.

EXAMPLE 25

2-Ethoxy-4-[N-{1-(2-piperidino-phenyl)-1-butyl}-aminocarbonylmethyl]-benzoic acid 100 mg (0.20 mmol) of tert.butyl 2-ethoxy-4-[N-{1-(2-piperidino-phenyl)-1-butyl}-aminocarbonyl]-benzoate were refluxed in 5 ml of benzene together with a few crystals of p-toluene-sulfonic acid hydrate for half a day. The desired product was obtained, as confirmed by thin-layer chromatography, by the $R_f$-value and mass spectrum.

M.p. 87–89° C. Calculated: m/e=438. Found: m/e=438.

EXAMPLE 26

2-Ethoxy-4-[N-{1-(2-piperidino-phenyl)-1-butyl}-aminocarbonylmethyl]-benzoic acid 0.25 g (0.47 mmcl) of benzyl 2-ethoxy-4-[N-{1-(2-piperidino-phenyl)-1-butyl}-aminocarbonylmethyl]-benzoate was hydrogenated in 10 ml of ethanol with 0.12 g of 10% palladium-on-charcoal at 50° C. and a pressure of 5 bar of hydrogen. After 5 hours the catalyst was filtered off through diatomaceous earth, and the filtrate was evaporated in vacuo. The evaporation residue was crystallized from petroleum ether/ethanol.

Yield: 0.14 g (70% of theory). M.p. 87–90° C. Calculated: C-71.21%; H-7.81%; N-6.39%. Found: C-71.46%; H-7.95%; N-6.51%.

EXAMPLE 27

Ethyl 2-ethoxy-4-[N-{1-(2-piperidino-phenyl)-1-n-hexyl}-aminocarbonylmethyl]-benzoate Prepared from 1-(2-piperidino-phenyl)-1-n-hexylamine and 3-ethoxy-4-ethoxycarbonyl-phenylacetic acid analogous to Example 1.

Yield: 43% of theory. M.p. 101–105° C. Calculated: C-72.84%; H-8.56%; N-5.66%. Found: C-72.72%; H-8.52%; N-5.63%.

EXAMPLE 28

2-Ethoxy-4-[N-{1-(2-piperidino-phenyl)-1-n-hexyl}-aminocarbonylmethyl]-benzoic acid Prepared from ethyl 2-ethoxy-4-[N-{1-(2-piperidino-phenyl)-1-n-hexyl}-aminocarbonylmethyl]-benzoate analogous to Example 4.

Yield: 77% of theory. M.p. 117–120° C. Calculated: C-72.07%; H-8.21%; N-6.00%. Found: C-72.00%; H-8.06%; N-5.90%.

EXAMPLE 29

[2-Ethoxy-4-[N-(1-(2-piperidino-phenyl)-1-butyl)-aminocarbonylmethyl]-phenyl]-acetonitrile To a solution of 2-ethoxy-4-[N-(1-(2-piperidino-phenyl)-1-butyl)-aminocarbonylmethyl]-benzyl chloride (2 g; 4.5 mmol)[prepared from 2-ethoxy-4-[N-(1-(2-piperidino-phenyl)-1-butyl)-aminocarbonylmethyl]-benzyl alcohol with thionyl chloride in chloroform), is added sodium cyanide (0.255 g, 5.2 mmol), dissolved in water (2.2 ml), and the phase transfer catalyst benzyl tributylammonium chloride (0.069 g, 0.22 mmol) and the mixture is stirred for 5 days at ambient temperature. Then, further phase transfer catalyst (0.069 g) is added, together with a few small grains of potassium iodide and sodium cyanide (0.2 g) in water (1 ml) and the mixture is stirred for a further 24 hours; then the same amounts of these three components are added again and the mixture is stirred for a further 12 hours. Methylene chloride (40 ml) is added and the mixture is extracted twice with water. The methylene chloride phase is dried over sodium sulphate/potassium carbonate, filtered and concentrated by evaporation in vacuo. The evaporation residue is purified by column chromatography on silica gel (toluene/ethyl acetate=5/1).

Yield: 1.53 g, Melting point: 116–118° C. (methylene chloride/ether); Calculated: C, 74.79; H, 8.14; N, 9.69; Found: 74.86; 8.19; 9.42.

EXAMPLE 30

[2-Ethoxy-4-[N-(α-phenyl-2-piperidino-benzyl)-aminocarbonylmethyl]-phenyl]-acetonitrile A solution of 2-ethoxy-4-[N-(α-phenyl-2-piperidino-benzyl)-aminocarbonylmethyl]-benzyl chloride (2.6 g, 5.45 mmol) in dimethylsulphoxide (10 ml) is added dropwise at 50–60° C. to sodium cyanide (0.32 g, 6.5 mmol) in dimethylsulphoxide (40 ml). The mixture is then stirred for 5 hours at 60° C., added to water and extracted with chloroform. The extract is concentrated by evaporation in vacuo. The residue is purified by column chromatography on silica gel (toluene/ethyl acetate=5/1).

Yield: 1.2 g, Melting point: 145–148° C.; Calculated: C, 77.05; H, 7.11; N, 8.99; Found: 76.92, 7.05, 8.78.

EXAMPLE 31

Ethyl [2-ethoxy-4-[N-(1-(2-piperidino-phenyl)-1-butyl)-aminocarbonylmethyl]-phenyl]-acetate Dry hydrogen chloride is introduced for 3 hours into a stirred and boiling solution of [2-ethoxy-4-[N-(1-(2-piperidino-phenyl)-1-butyl)-aminocarbonylmethyl]-phenyl]-acetonitrile (1.3 g, 3 mmol) in absolute ethanol (30 ml). The mixture is then evaporated down in vacuo, water (25 ml) is added to the evaporation residue and this is stirred for 15 minutes at 50° C. The mixture is adjusted to a pH of 7 by the addition of solid sodium hydrogen carbonate and is extracted three times with ethyl acetate. The ccnbined organic extracts are shaken once with water, then dried over sodium sulphate/potassium carbonate, filtered and concentrated by evaporation in vacuo. The evaporation residue is purified by column chromatography on silica gel (chloroform/ethyl acetate=9/1).

EXAMPLE 32

Methyl [2-ethoxy-4-[N-(α-phenyl-2-piperidino-benzyl)-amino-carbonylmethyl]-phenyl]-acetate Dry hydrogen chloride is introduced for 4 hours into a stirred and refluxed solution of [2-ethoxy-4-(N-(α-phenyl-2-piperidino-benzyl)-aminocarbonylmethyl]-phenyl]-acetonitrile (1.2 g, 2.57 mmol) in methanol (20 ml). The mixture is then concentrated by evaporation, added to water and extracted with chloroform. The extract is dried and filtered and concentrated by evaporation in vacuo. The evaporation residue is purified by column chromatography on silica gel (toluene/ethyl acetate=4/1).

Yield: 340 mg, Melting point: 136–138° C. (acetonitrile/water); Calculated: molecular peak m/e=500; Found: molecular peak m/e=500

EXAMPLE 33

[2-Ethoxy-4-[N-(1-(2-piperidino-phenyl)-1-butyl-aminocarbonylmethyl-]-phenyl]-acetic acid A 1N sodium hydroxide solution (2.8 ml) is added to ethyl [2-ethoxy-4-[N-(1-(2-piperidino-phenyl)- 1-butyl-aminocarbonylmethyl]-phenyl]-acetate (0.67 g, 1.4 mmol) in ethanol (10 ml) and stirred for 4 hours at ambient temperature. Then the mixture is evaporated down in vacuo at 50° C. Water and a few drops of methanol are added to the evaporation residue which is then adjusted to pH 6 with 1N acetic acid. It is cooled in ice, whereupon a precipitate is formed. This is filtered off and recrystallised from ethanol.

Yield: 0.47 g, Melting point: 158–159° C. (ethanol); Calculated: C, 71.65; H, 8.02; N, 6.19; Found: 71.35; 8.30; 6.21.

EXAMPLE 34

[2-Ethoxy-4-[N-(α-phenyl-2-piperidino-benzyl)-aminocarbonylmethyl]-phenyl]-acetic acid Prepared analogously to Example 5 by alkaline saponification of methyl [2-ethoxy-4-[N-(α-phenyl-2-piperidino-benzyl)-aminocarbonylmethyl]-phenyl]-acetate Melting point: 146–148° C.; Calculated: C, 74.05; H, 7.04; N, 5.76; Found: 73.70; 7.00; 5.85.

EXAMPLE 35

Ethyl 2-ethoxy-4-[N-(1-(2-piperidino-phenyl)-1-butyl)-aminocarborylmethyl]-cinnamate A solution of ethyl diethyl-phosphono-acetate (1.68 g, 7.5 mmol) in absolute dioxan (3 ml) is slowly added dropwise, with vigorous stirring, to a suspension of 55% sodium hydride (in oil) (0.327 g, 7.5 mmol) in absolute dioxan (4 ml). After the reaction has died down the mixture is heated to 80° C. for a further 45 minutes. It is then cooled to ambient temperature, a solution of 2-ethoxy-4-[N-(1-(2-piperidino-phenyl)-1-butyl)-aminocarbonyl-methyl]-benzaldehyde (2.11 g, 5 mmol) [prepared from the corresponding benzyl alcohol by oxidation with pyridinium chlorochromate in chloroform] in absolute dioxan (4 ml) is added dropwise thereto and the mixture is heated for 2 hours at 50° C. The reaction mixture is poured onto ice/water and extracted with chloroform. The organic extract is dried and filtered and evaporated down in vacuo. The evaporation residue is purified by column chromatography on silica gel (chloroform/ethyl acetate=19/1).

Yield: 1.64 g, Melting point: 130–131° C. (ether); Calculated: C, 73.14; H, 8.18; N, 5.69; Found: 73.36; 8.34; 5.75.

EXAMPLE 36

2-Ethoxy-4-[N-(1-(2-piperidino-phenyl)-1-butyl)-aminocarbonylmethyl]-cinnamic acid nitrile Prepared analogously to Example 7 from 2-ethoxy-4-[N-(1-(2-piperidino-phenyl)-1-butyl)-aminocarbonylmethyl]-benzaldehyde with diethylphosphono-acetonitrile.

Melting point: 125–128° C. (petroleum ether); Calculated: C, 75.47; H, 7.92; N, 9.43; Found: 75.40; 7.95; 9.24.

EXAMPLE 37

Ethyl 2-ethoxy-4-[N-(α-phenyl-2-piperidino-benzyl)-amino-carbonylmethyl]-cinnamate Under a nitrogen atmosphere, 50% sodium hydride (0.19g, 8 mmol) is added to a stirred solution of ethyl diethylphosphono-acetate (1.8 g, 8 mmol) in absolute 1,2-dimethoxy-ethane (10 ml). Then a solution of 2-ethoxy-4-[N-(α-phenyl-2-piperidino-benzyl)-aminocarbonylmethyl]-benzaldehyde (2 g, 4.4 mmol) in absolute 1,2-dimethoxy-ethane (15 ml) is added and the mixture is stirred for 30 minutes at ambient temperature. It is concentrated by evaporation in vacuo and the evaporation residue is distributed between water and chloroform. The chloroform extract is dried and filtered and concentrated by evaporation in vacuo. The evaporation residue is purified by column chromatography on silica gel (toluene/ethyl acetate=5/1).

Yield: 0.37 g, Melting point: 111–113° C. (cyclohexane); Calculated: C, 75.26; H, 7.27; N, 5.32; Found: 75.14; 7.32; 5.25.

EXAMPLE 38

2-Ethoxy-4-[N-(1-(2-piperidino-phenyl)-1-butyl)-aminocarbonylmethyl]-cinnamic acid A solution of ethyl 2-ethoxy-4-[N-{1-(2-piperidino-phenyl)-1-butyl)-aminocarbonyl-methyl]-cinnamate (0.49 g, 1 mmol) in ethanol (10 ml) is stirred together with 1N sodium hydroxide solution (2 ml) for 3 days at ambient temperature. The mixture is then concentrated by evaporation in vacuo, water and a few drops of methanol are added to the evaporation residue and this is then adjusted to pH 6 with 1N acetic acid. The precipitate is filtered off, dried and recrystallised from ethyl acetate.

Yield: 0.37 g, Melting point: 175–177° C. (decomp.); Calculated: C, 72.39; H, 7.81; N, 6.03; Found: 72.50; 7.88; 6.06.

EXAMPLE 39

2-Ethoxy-4-[N-(α-phenyl-2-piperidino-benzyl)-aminocarbonylmethyl]-cinnamic acid

Ethyl 2-ethoxy-4-[N-(α-phenyl-2-piperidino-benzyl)-aminocarbonylmethyl]-cinnamate (330 mg, 0.62 mmol) is dissolved in ethanol (10 ml) and, after the addition of 4N sodium hydroxide solution (4 ml), stirred for 3 hours at 50° C. Then the mixture is neutralized with 4N hydrochloric acid (4 ml), diluted with water and, filtered off from the precipitate. It is then recrystallized from aqueous ethanol.

(Page start: Yield: 1.0 g, Melting point: 91–93° C. (petroleum ether); Calculated: C, 72.47; H, 8.39; N, 5.83; Found: 72.73; 8.68; 5.71.)

Yield: 210 mg, Melting point: 181° C.; Calculated: C, 74.67; H, 6.87; N, 5.62; Found: 74.72; 6.76; 5.42.

EXAMPLE 40

Ethyl 3-[2-ethoxy-4-[N-(1-(2-piperidino-phenyl)-1-butyl)-aminocarbonylmethyl]-phenyl]-propionate A solution of of ethyl 2-ethoxy-4-[N-(1-(2-piperidino-phenyl)-1-butyl)-aminocarbonylmethyl]-cinnamate (0.54 g, 1.1 mmol) in ethanol (15 ml) is hydrogenated for 1 hour at ambient temperature and under 3 bars of hydrogen on 10% palladium/charcoal (0.1 g). The mixture is filtered, concentrated by evaporation in vacuo and the evaporation residue is crystallized from petroleum ether.

Yield: 0.30 g, Melting point: 71–73° C.; Calculated: C, 72.84; H, 8.56; N, 5.66; Found: 73.19; 8.54; 5.70.

EXAMPLE 41

Ethyl 3-[2-ethoxy-4-[N-(α-phenyl-2-piperidino-benzyl)-aminocarbonylmethyl]-phenyl]-propionate Prepared analogously to Example 12 by catalytic hydrogenation of ethyl 2-ethoxy-4-[N-(αphenyl-2-piperidino-benzyl)-aminocarbonylmethyl]-cinnamate and subsequent purification by column chromatography on silica gel (cyclohexane/ethyl acetate/methanol=6/1/0.5).

Melting point: 130° C. (ethanol/water); Calculated: C, 74.97; H, 7.63; N, 5.30; Found: 74.65; 7.61; 5.15.

EXAMPLE 42

3-(2-Ethoxy-4-[N-(1-(2-piperidino-phenyl)-1-butyl)-aminocarbonylmethyl]-phenyl]-propionic acid Prepared analogously to Example 12 by catalytic hydrogenation of 2-ethoxy-4-[N-(1-(2-piperidino-phenyl)-1-butyl)-aminocarbonylmethyl]-cinnamic acid.

Melting point: 112–114° C.; Calculated: C, 72.07; H, 8.21; N, 6.00; Found: 72.30; 8.42; 6.19.

EXAMPLE 43

3-[2-Ethoxy-4-[N-(1-(2-piperidino-phenyl)-1-butyl)-aminocarbonylmethyl]-phenyl]-propionitrile Prepared analogously to Example 12 by catalytic hydrogenation of 2-ethoxy-4-[N-(1-( 2-piperidino-phenyl)-1-butyl)-aminocarbonylmethyl]-cinnamic acid nitrile.

Melting point: 102–103° C. (petroleum ether); Calculated: molecular peak m/e=447; Found: molecular peak m/e=447

EXAMPLE 44

3-[2-Ethoxy-4-[N-(1-(2-piperidino-phenyl)-1-butyl)-aminocarbonylmethyl]-phenyl]-propionic acid Prepared analogously to Example 5 by alkaline saponification of ethyl 3-[2-ethoxy-4-[N-(1-(2-piperidino-phenyl)-1-butyl)-aminocarbonylmethyl]-phenyl]-propionate and subsequent purification by column chromatography (chloroform/methanol=9/1).

Melting point: 112–115° C. (petroleum ether); Calculated: C, 72.07; H, 8.21; N, 6.00; Found: 72.40; 8.21; 6.03.

EXAMPLE 45

3-[2-Ethoxy-4-[N-(α-phenyl-2-piperidino-benzyl)-aminocarbonylmethyl]-phenyl]-propionic acid Prepared analogously to Example 5 by alkaline saponification of ethyl 3-[2-ethoxy-4-[N-(α-phenyl-2-piperidino-benzyl)-aminocarbonylmethyl]-propionate.

Melting point: 74° C.; Calculated: C, 74.37; H, 7.25; N, 5.60; Found: 74.29; 7.31; 5.27.

EXAMPLE 46

3-(2-Ethoxy-4-[N-(1-(2-piperidino-phenyl)-1-butyl)-aminocarbonylmethyl]-phenyl]-propionitrile At ambient temperature, p-toluenesulphonic acid chloride (45.8 mg, 0.24 mmol) is added to a mixture of 3-[2-ethoxy-4-[N-(1-(2-piperidino-phenyl)-1-butyl)-aminocarbonylmethyl]-phenyl]-propionic acid amide, (56 mg, 0.12 mmol) melting point 153–155° C. [prepared from the corresponding propionic acid by reacting with carbonyldiimidazole and then with ammonia in tetrahydrofuran] and absolute pyridine (0.044 ml). The mixture is stirred for 45 minutes at 20° C. and for 2 hours at 50 to 60° C. After cooling, water is added, the mixture is made alkaline with concentrated ammonia and extracted three times with chloroform. The combined chloroform extracts are washed with water, dried over sodium sulphate, filtered and concentrated by evaporation in vacuo. The evaporation residue is purified by column chromatography on silica gel (chloroform/ethyl acetate=9/1).

Yield: 11 mg, Calculated: molecular peak m/e=447; Found: molecular peak m/e=447

EXAMPLE 47

Ethyl 2-ethoxy-4-[N-(α-cyclohexylmethyl-2-piperidino-benzyl)-aminocarbonylmethyl]-benzoate To a solution of α-cyclohexylmethyl-2-piperidino-benzylamine (1.13 g, 3.96 mmol) in acetonitrile (11 ml) are added, successively, 3-ethoxy-4-ethoxycarbonyl-phenyl acetic acid (1 g, 3.96 mmol), of triphenylphosphine (1.25 g, 4.76 mmol), triethylamine (1.11 ml, 7.92 mmol) and carbon tetrachloride (0.38 ml, 3.96 mmol) and the mixture is stirred for 15 hours at ambient temperature. It is then concentrated by evaporation in vacuo and partitioned between ethyl acetate and water. The organic extract is dried and filtered and concentrated by evaporation in vacuo. The evaporation residue is purified by column chromatography on silica gel (toluene/acetone=10/1).

Yield: 1.4 g, Melting point: 95–97° C. (petroleum ether/cyclohexane=1/1); Calculated: C, 73.81; H, 8.52; N, 5.38; Found: 73.98; 8.49; 5.61.

EXAMPLE 48

Ethyl 2-ethoxy-4-[N-(α-benzyl-2-piperidino-benzyl)-aminocarbonylmethyl]-benzoate Prepared analogously to Example 19 from α-benzyl-2-piperidino-benzylamine and 3-ethoxy-4-ethoxycarbonyl-phenylacetic acid.

Melting point: 102–105° C. (petroleum ether); Calculated: C, 74.68; H, 7.44; N, 5.44; Found: 74.73; 7.68; 5.39.

EXAMPLE 49

2-Ethoxy-4-[N-(α-cyclohexylmethyl-2-piperidino-benzyl)-aminocarbonylmethyl]-benzoic acid Ethyl 2-ethoxy-4-[N-(α-cyclohexyl-methyl-2-piperidino-benzyl)-aminocarbonylmethyl]-benzoate (1.15 g, 2.21 mmol) in ethanol (12 ml) are stirred together with 1N sodium hydroxide solution (3.3 ml) for 2 hours at 50° C. Then 1N hydrochloric acid (3.3 ml) is added and the mixture is cooled in ice. The precipitate formed is filtered off, washed with a little ice cold ethanol and dried in vacuo at 100° C.

Yield: 0.9 g, Melting point: 153–156° C.; Calculated: C, 73.14; H, 8.18; N, 5.69; Found: 73.30; 8.17; 5.66.

EXAMPLE 50

2-Ethoxy-4-[N-(α-benzyl-2-piperidino-benzyl)-aminocarbonylmethyl]-benzoic acid

Prepared analogously to Example 21 by alkaline saponification of ethyl 2-ethoxy-4-[N-(α-benzyl-2-piperidino-benzyl)-3minocarbonylmethyl]-benzoate.

Melting point: 100–105° C.; Calculated: C, 74.05; H, 7.04; N, 5.76; Found: 73.77; 7.10; 5.50.

EXAMPLE 51

Ethyl 2-ethoxy-4-[N-(α-ethoxycarbonyl-2piperidino-benzyl)-aminocarbonylmethyl]-benzoate To a mixture of (2-piperidino-phenyl)-glycine-ethyl ester-dihydrochloride (2 g, 5.96 mmol) in acetonitrile (12 ml) are added successively 3-ethoxy-4-ethoxycarbonyl-phenyl-acetic acid, (1.52g, 5.96 mmol) triphenylphosphine (1.77 g, 6.75 mmol), triethylamine (2.45 ml, 17.9 mmol) and carbon tetrachloride (0.57 ml, 5.96 mmol) and the mixture is stirred overnight at ambient temperature. It is then concentrated by evaporation in vacuo and partitioned between chloroform and water. The organic extract is dried and filtered and concentrated by evaporation in vacuo. The evaporation residue is purified by column chromatography on silica gel (toluene/acetone=4/1).

Yield: 1.2 g, Melting point: 100–103° C. (ether); Calculated: C, 67.72; H, 7.31; N, 5.64; Found: 67.87; 7.46; 5.61.

EXAMPLE 52

Benzyl 2-ethoxy-4-[N-(α-ethoxycarbonyl-2-piperidino-benzyl)-aminocarbonylmethyl]-benzoate Prepared analogously to Example 23 from (2-piperidino-phenyl)-glycine-ethyl ester-dihydrochloride and 3-ethoxy-4-benzyloxycarbonyl-phenyl acetic acid.

Melting point: 90–93° C.; Calculated: molecular peak m/e=558; Found: molecular peak m/e=558

EXAMPLE 53

Benzyl 2-ethoxy-4-[N-(α-methoxycarbonyl-2-piperidino-benzyl)-aminocarbonylmethyl]-benzoate Prepared analogously to Example 23 from (2-piperidino-phenyl)-glycine-methyl ester-dihydrochloride and 3-ethoxy-4-benzyloxycarbonyl-phenyl acetic acid.

Melting point: 100–102° C. (ether); Calculated: C, 70.57; H, 6.66; N, 5.14; Found: 70.46; 6.67; 5.14.

EXAMPLE 54

Benzyl 2-ethoxy-4-[N-(α-propoxycarbonyl-2-piperidino-benzyl)-aminocarbonylmethyl]-benzoate Prepared analogously to Example 23 from (2-piperidino-phenyl)-glycine-n-propylester-dihydrochloride and 3-ethoxy-4-benzyloxycarbonyl-phenylacetic acid.

Melting point: 100–102° C. (petroleum ether); Calculated: C, 71.31; H, 7.04; N, 4.89; Found: 71.62; 7.01; 4.97.

EXAMPLE 55

Benzyl 2-ethoxy-4-[N-(α-isopropoxycarbonyl-2-piperidino-benzyl)-aminocarbonylmethyl]-benzoate Prepared analogously to Example 23 from (2-piperidino-phenyl)-glycine-isopropylester-dihydrochloride and 3-ethoxy-4-benzyloxycarbonyl-phenylacetic acid.

Melting point: 85–88° C. (acetone/petroleum ether); Calculated: C, 71.31; H, 7.04; N, 4.89; Found: 71.64; 7.10; 4.77.

EXAMPLE 56

Ethyl 4-[N-(α-ethoxycarbonyl-2-piperidino-benzyl)-aminocarbonylmethyl]-2-hydroxy-benzoate Prepared analogously to Example 23 from (2-piperidino-phenyl)-glycine-ethylester-dihydrochloride and 4-ethoxycarbonyl-3-hydroxy-phenylacetic acid.

Melting point: 107–110° C. (petroleum ether); Calculated: C, 66.65; H, 6.88; N, 5.98; Found: 66.60; 6.86; 6.03.

EXAMPLE 57

Ethyl 2-ethoxy-4-[N-(α-hydroxymethyl-2-piperidino-benzyl)-aminocarbonylmethyl]-benzoate First, 3-ethoxy-4-ethoxycarbonyl-phenylacetic acid (2.52 g, 10 mmol) and N,N'-carbonyldiimidazole (1.62 g, 10 mmol) are heated to 70° C. for 45 minutes in absolute tetrahydrofuran (15 ml). A solution of 2-hydroxy-1-(2-piperidino-phenyl)-1-ethylamine (2.07 g, 9.4 mmol) [prepared by reducing (2-piperidino-phenyl)-glycine-ethylester with lithium aluminium hydride in ether] in absolute tetrahydrofuran (7 ml) is added thereto and the mixture is refluxed for 1 hour. After standing overnight it is diluted with ethyl acetate (50 ml) and shaken twice with water (30 ml). The organic phase is dried and filtered and concentrated by evaporation in vacuo. The evaporation residue is purified by column chromatography on silica gel (chloroform/methanol=19/1).

Yield: 2.4 g, Melting point: 127–128° C. (acetone); Calculated: C, 68.70; H, 7.54; N, 6.16; Found: 68.80; 7.58; 6.15.

EXAMPLE 58

Benzyl 2-ethoxy-4-[N-(α-hydroxymethyl-2-piperidino-benzyl)-aminocarbonylmethyl]-benzoate Prepared analogously to Example 29 from 3-ethoxy-4-benzyloxycarbonyl-phenylacetic acid and 2-hydroxy-1-(2-piperidino-phenyl)-1-ethylamine.

Melting point: 89–91° C. (acetone/ether); Calculated: C, 72.07; H, 7.02; N, 5.42; Found: 72.10; 7.15; 5.29.

EXAMPLE 59

2-Ethoxy-4-[N-(α-carboxy-2-piperidino-benzyl)-amino-carbonylmethyl]-benzoic acid Ethyl 2-ethoxy-4-[N-(α-ethoxycarbonyl-2-piperidino-benzyl)-aminocarbonylmethyl]-benzoate (0.45 g, 0.9 mmol) in ethanol (5 ml) is stirred together with 1N sodium hydroxide solution (2.7 ml) for 2 hours at 50° C. Then 1N hydrochloric acid (2.7 ml) is added and the mixture is concentrated by evaporation in vacuo. The evaporation residue is partitioned between water and chloroform. The combined chloroform extracts are shaken once with water, then the organic phase is dried, filtered and evaporated down in vacuo. The evaporation residue is crystallized with ether.

Yield: 0.27 g, Melting point: 222–225° C. (decomp.); Calculated: C, 65.44; H, 6.41; N, 6.36; Found: 65.58; 6.59; 6.28.

EXAMPLE 60

4-[N-(α-Carboxy-2-piperidino-benzyl)-aminocarbonylmethyl]-2-hydroxy-benzoic acid Prepared analogously to Example 31 by alkaline saponification of ethyl 4-[N-(α-ethoxycarbonyl-2-piperidino-benzyl)-aminocarbonylmethyl]-2-hydroxy-benzoate.

Melting point: 220–228° C.; Calculated: C, 64.07; H, 5.87; N, 5.79; Found: 63.84; 5.95; 7.13.

EXAMPLE 61

2-Ethoxy-4-[N-(α-hydroxymethyl-2-piperidino-benzyl)-aminocarbonylmethyl]-benzoic acid Prepared analogously to Example 31 by alkaline saponification of ethyl 2-ethoxy-4-[N-(α-hydroxymethyl-2-piperidino-benzyl)-aminocarbonylmethyl]-benzoate and purification by column chromatography on silica gel (chloroform/ethanol=95/5).

Melting point: 80–81° C. (decomp. sintering from 75° C.); Calculated: molecular peak m/e=426; Found: molecular peak m/e=426

EXAMPLE 62

Ethyl 2-ethoxy-4-[N-(α-carboxy-2-piperidino-benzyl)-amino-carbonylmethyl]-benzoate Ethyl 2-ethoxy-4-[N-(α-ethoxycarbonyl- 2-piperidino-benzyl)-aminocarbonylmethyl]-benzoate (0.45 g, 0.9 mmol) in ethanol (5 ml) is stirred together with 1N sodium hydroxide solution (0.90 ml) for 4 hours at ambient temperature. Then 1N hydrochloric acid (0.90 ml) is added and the mixture is evaporated down in vacuo. The residue is partitioned between water and chloroform, the chloroform solution is dried and filtered and concentrated by evaporation in vacuo. The evaporation residue is purified by column chromatography on silica gel (chloroform/ethanol=5/1).

Yield: 0.23 g, Melting point: 177–180° C. (ether); Calculated: C, 66.65; H, 6.88; N, 5.98; Found: 66.65; 7.11; 5.79.

EXAMPLE 63

Ethyl 4-[N-(α-carboxy-2-piperidino-benzyl)-aminocarbonyl-methyl]-2-hydroxy-benzoate Prepared analogously to Example 34 by alkaline saponification of ethyl 4-[N-(α-ethozycarbonyl-2-piperidino-benzyl}-aminocarbonylmethyl]-2-hydroxy-benzoate.

Melting point: 156–159° C. (ether); Calculated: C, 65.44; H, 6.41; N, 6.36; Found: 65.66; 6.38; 6.33.

EXAMPLE 64

Benzyl 2-ethoxy-4-[N-(α-carboxy-2-piperidino-benzyl)-aminocarbonylmethyl]-benzoate Prepared analogously to Example 34 by alkaline saponification of benzyl 2-ethoxy-4-[N-(α-methoxycarbonyl-2-piperidino-benzyl)-aminocarbonyl methyl]-benzoate in dioxan.

Melting point: 140–142° C.; Calculated: C, 70.17; H, 6.46; N, 5.28; Found: 70.21; 6.50; 5.31.

EXAMPLE 65

Ethyl 2-ethoxy-4-[N-(α-acetoxymethyl-2-piperidino-benzyl)-aminocarbonylmethyl]-benzoate To a solution of of ethyl 2-ethoxy-4-[N-(α-hydroxymethyl-2-piperidino-benzyl)-aminocarbonylmethyl]-benzoate (0.227 g, 0.5 mmol) and absolute triethylamine (0.126 ml, 0.9 mmol) in absolute chloroform (3 ml), a solution of acetyl chloride (0.063 ml, 0.9 mmol) in absolute chloroform (1 ml) is added dropwise. After 4 days' stirring at ambient temperature the mixture is diluted with chloroform, washed with dilute aqueous sodium bicarbonate solution, the chloroform solution is dried and filtered and evaporated down in vacuo. The evaporation residue is purified by column chromatography on silica gel (chloroform/acetone=4/1).

Yield: 0.17 g, Melting point: 107–109° C. (ether/petroleum ether); Calculated: C, 67.72; H, 7.31; N, 5.64; Found: 67.70; 7.48; 5.74.

EXAMPLE 66

Benzyl 2-ethoxy-4-[N-(α-acetoxymethyl-2-piperidino-benzyl)-aminocarbonylmethyl]-benzoate Prepared analogously to Example 37 from benzyl 2-ethoxy-4-[N-(α-hydroxymethyl-2-piperidino-benzyl)-aminocarbonylmethyl]-benzoate with acetyl chloride. Calculated: molecular peak m/e=558; Found: molecular peak m/e=558

EXAMPLE 67

Benzyl 2-ethoxy-4-[N-(α-propionyloxymethyl-2-piperidino-benzyl)-aminocarbonylmethyl]-benzoate Prepared analogously to Example 37 from benzyl 2-ethoxy-4-[N-(α-hydroxymethyl-2-piperidino-benzyl)-aminocarbonylmethyl]-benzoate with propionyl chloride.

Melting point: 73–74° C.; Calculated: C, 71.31; H, 7.04; N, 4.89; Found: 71.20; 7.10; 4.61.

EXAMPLE 68

2-Ethoxy-4-[N-(α-ethoxycarbonyl-2-piperidino-benzyl)-aminocarbonylmethyl]-benzoic acid A solution of benzyl 2-ethoxy-4-[N-(α-ethoxycarbonyl-2-piperidino-benzyl)-aminocarbonylmethyl]-benzoate (0.140 g, 0.25 mmol) in ethanol (1.4 ml) is hydrogenated with 10% palladium/charcoal (0.03 g)for 4.5 hours at 50° C. under 5 bar of hydrogen. The mixture is filtered, evaporated down in vacuo and the evaporation residue is purified by column chromatography on silica gel (chloroform/methanol=10/1).

Yield: 0.041 g, Meltng point: 115–118° C. (petroleum ether); Calculated: molecular peak m/e=468; Found: molecular peak m/e=468

EXAMPLE 69

2-Ethoxy-4-[N-(α-methoxycarbonyl-2-piperidino-benzyl)-aminocarbonylmeethyl-benzoic acid Prepared analogously to Example 40 by catalytic hydrogenation of benzyl 2-ethoxy-4-[N-(α-methoxycarbonyl-2-piperidino-benzyl)-aminocarbonylmethyl]-benzoate in methanol.

Melting point: 147–150° C. (decomp.) (ether); Calculated: C, 66.06; H, 6.65; N, 6.16; Found: 66.28; 6.56; 5.90.

EXAMPLE 70

2-Ethoxy-4-[N-(α-n-propoxycarbonyl-2-piperidino-benzyl)-aminocarbonylmethyl]-benzoic acid Prepared analogously to Example 40 by catalytic hydrogenation of benzyl 2-ethoxy-4-[N-(α-n-propoxycarbonyl-2-piperidino-benzyl)-aminocarbonylmethyl]-benzoate in n-propanol.

Melting point: 122–125° C. (ether/petroleum ether=1/1); Calculated: C, 67.20; H, 7.10; H, 5.80; Found: 67.39; 7.24; 5.78.

EXAMPLE 71

2-Ethoxy-4-[N-(α-isopropoxycarbonyl-2piperidino-benzyl)-aminocarbonylmethyl]-benzoic acid Prepared analogously to Example 40 by catalytic hydrogenation of benzyl 2-ethozy-4-[N-(α-isopropoxycarbonyl-2-piperidino-benzyl)-aminocarbonylmethyl]-benzoate in isopropanol.

Melting point: 149–151° C. (acetone/petroleum ether); Calculated: C, 67.20; H, 7.10; N, 5.80; Found: 67.50; 6.99; 5.78.

EXAMPLE 72

2-Ethoxy-4-[N-(α-acetoxymethyl-2piperidino-benzyl)-aminocarbonylmethyl]-benzoic acid Prepared analogously to Example 40 by catalytic hydrogenation of benzyl 2-ethoxy-4-[N-(α-acetoxymethyl-2-piperidino-benzyl)-aminocarbonylmethyl]-benzoate in ethanol.

Calculated: molecular peak m/e=468; Found: molecular peak m/e=468

EXAMPLE 73

2-Ethoxy-4-[N-(α-propionyloxymethyl-2-piperidino-benzyl)-aminocarbonylmethyl]-benzoic acid Prepared analogously to Example 40 by catalytic hydrogenation of benzyl 2-ethoxy-4-[N-(α-propionyloxymethyl-2-piperidino-benzyl)-aminocarbonylmethyl]-benzoate in ethanol.

Melting point: 64–67° C. (ethanol/water); Calculated: molecular peak m/e=482; Found: molecular peak m/e=482

EXAMPLE 74

2-Hydroxy-4-[N-(α-isopropoxycarbonyl-2-piperidino-benzyl)-aminocarbonylmethyl]-benzoic acid Boron tribromide (0.04 ml, 0.414 mmol) is added at −20° C. with the exclusion of moisture to a stirred solution of 2-ethoxy-4-[N-(α-isopropoxycarbonyl-2-piperidino-benzyl)-amino-carbonylmethyl]-benzoic acid (0.20 g, 0.414 mmol) in 1,2-dichloroethane (5 ml). The mixture is allowed to come up to ambient temperature and is then stirred for 2 hours. It is poured into isopropanol, the mixture is concentrated by evaporation in vacuo, water is added and the mixture is extracted with chloroform. The organic extract is dried and filtered and evaporated down in vacuo. The evaporation residue is purified by column chromatography on silica gel (chloroform methanol/glacial acetic acid −5/1/0.01).

Yield: 0.14 g, Melting point: 190–200° C. (ether); Calculated: molecular peak m/e=454; Found: molecular peak m/e=454

EXAMPLE 75

Ethyl 2-ethoxy-4-[N-(α-ethoxymethyl-2-piperidino-benzyl)-aminocarbonylmethyl]-benzoate Ethyl 2-ethoxy-4-[N-(α-hydroxymethyl-2-piperidino-benzyl)-aminocarbonylmethyl]-benzoate (0.64 g, 1.4 mmol) is added with stirring at ambient temperature to sodium hydride (0.061 g, 1.4 mmol) (55% in oil) in absolute tetrahydrofuran (6.4 ml). The mixture is stirred for 1 hour, then ethyl iodide (0.113 ml, 1.4 mmol) is added and the mixture is stirred for a further 16 hours at ambient temperature. Then ethanol (2 ml) is added and the mixture is evaporated down in vacuo. The evaporation residue is partitioned between chloroform and water. The organic phase is washed twice with water, dried, filtered and concentrated by evaporation in vacuo. The evaporation residue is purified by column chromatography on silica gel (chloroform/acetone a 17/3).

Yield: 0.05 g, Melting point: 85–87° C. (petroleum ether); Calculated: molecular peak m/e=482; Found: molecular peak m/e=482

EXAMPLE 76

2-Ethoxy-4-[N-(α-ethoxymethyl-2-piperidino-benzyl)-aminocarbonylmethyl]-benzoic acid Prepared analogously to Example 31 by alkaline saponification of ethyl 2-ethoxy-4-[N-(α-ethoxymethyl-2-piperidino-benzyl)-aminocarbonylmethyl]-benzoate.

Calculated: molecular peak m/e=454; Found: molecular peak m/e=454

EXAMPLE 77

4-[N-(α-Carboxy-2-piperidino-benzyl)-aminocarbonylmethyl]-2-hydroxy-benzoic acid Prepared analogously to Example 46 by reacting 2-ethoxy-4-[N-(α-isopropoxycarbonyl-2-piperidino-benzyl)-aminocarbonylmethyl]-benzoic acid with 2.5 equivalents of boron tribromide in methylene chloride.

Melting point: 220–230° C. (water); Calculated: C, 64.07; H, 5.87; N, 6.79; Found: 64.21; 5.99; 6.81.

EXAMPLE 78

3-(2-Ethoxy-4-[N-(1-(2-piperidino-phenyl)-1-butyl)-aminocarbonylmethyl]-phenyl]-propionitrile Magnesium chips (0.11 g, 4.5 mmol) are added to 2-ethoxy-4-[N-(1-(2-piperidino-phenyl)-1-butyl)-aminocarbonylmethyl]-cinnamic acid nitrile (0.05 g, 0.11 mmol) in methanol (1.1 ml) and the mixture is stirred for 45 minutes at 25° C. and for 1 hour at 0° C. It is then cooled to 0° C. and mixed with of 1N hydrochloric acid (4.5 ml). It is diluted with water, filtered over kieselguhr and extracted with chloroform. The chloroform extract is washed with aqueous sodium bicarbonate solution, dried and filtered and concentrated by evaporation in vacuo. The evaporation residue is purified by column chromatography on silica gel (chloroform/ethyl acetate=9/1).

Yield: 0.015 g, Melting point: 102–104° C. (petroleum ether); Calculated: molecular peak m/e=447; Found: molecular peak m/e=447

EXAMPLE 79

[2-Ethoxy-4-[N-(1-(2-piperidino-phenyl)-3-methyl-1-butyl)-aminocarbonylmethyl]-phenyl]-acetonitrile Prepared analogously to Example 1 from 2-ethoxy-4-[N-(1-(2-piperidino-phenyl)-3-methyl-1-butyl)-aminocarbonylmethyl]benzyl chloride with sodium cyanide.

Melting point: 135–136° C.; Calculated: C, 75.13; H, 8.33; N, 9.39; Found: 75.12; 8.18; 9.18.

EXAMPLE 80

Ethyl 2-ethoxy-4-[N-(α-cyclopropylmethyl-2-piperidino-benzyl)-aminocarbonylmethel]-benzoate Prepared analogously to Example 19 from α-cyclopropylmethyl-2-piperidino-benzylamine and 3-ethoxy-4-ethoxycarbonyl-phenylacetic acid.

Melting point: 126–127° C.; Calculated : C, 72.77; H, 8.00; N, 5.85; Found: 72.85; 7.74; 5.84.

EXAMPLE 81

2-Ethoxy-4-[N-(α-cyclopropylmethyl-2-piperidino-benzyl)-aminocarbonylmethyl]-benzoic acid hemihydrate Prepared analogously to Example 21 by alkaline saponification of ethyl 2-ethoxy-4-[N-(α-cyclopropylmethyl-2-piperidino-benzyl)-aminocarbonylmethyl]-benzoate.

Melting point: 103–104° C.; Calc. (×0.5 $H_2O$): C, 70.55; H, 7.68; N, 6.10; Found: 70.67; 7.67; 6.37.

EXAMPLE 82

Ethyl 2-ethoxy-4-[N-(α-cyclobutylmethyl-2-piperidino-benzyl)-aminocarbonylmethyl]-benzoate Prepared analogously to Example 19 from α-cyclobutylmethyl-2-piperidino-benzylamine and 3-ethoxy-4-ethoxycarbonyl-phenyl acetic acid.

Melting point: 116–118° C.; Calculated: C, 73.14; H, 8.18; N, 5.69; Found: 73.14; 8.32; 5.64.

EXAMPLE 83

2-Ethoxy-4-[N-(α-cyclobutylmethyl-2-piperidino-benzyl)-aminocarbonylmethyl]-benzoic acid Prepared analogously to Example 21 by alkaline saponifcation of ethyl 2-ethozy-4-[N-(α-cyclobutylmethyl-2-piperidino-benzyl)-aminocarbonylmethyl]-benzoate.

Melting point: 140–142° C.; Calculated: C, 72.39; H, 7.81; N, 6.03; Found: 72.15, 7.79; 5.97.

EXAMPLE 84

Ethyl 2-ethoxy-4-[N-(α-cyclopentylmethyl-2-piperidino-benzyl)-aminocarbonylmethyl]-benzoate Prepared analogously to Example 19 from α-cyclopentylmethyl-2-piperidino-benzylamine and 3-ethoxy-4-ethoxycarbonyl-phenyl-acetic acid.

Melting point: 120–210° C.; Calculated: C, 73.49; H, 8.36; N, 5.53, Found: 73.31; 8.55; 5.39.

EXAMPLE 85

2-Ethoxy-4-[N-(α-cyclopentylmethyl-2-piperidino-benzyl)-aminocarbonylmethyl]-benzoic acid Prepared analogously to Example 21 by alkaline saponification of ethyl 2-ethox-4-[N-(α-cyclopentyl-methyl-2-piperidino-benzyl)-aminocarbonylmethyl]-benzoate.

Melting point: 85–88° C.; Calculated: C, 72.77; H, 8.00; N, 5.85; Found: 72.50; 8.02; 6.03.

EXAMPLE 86

Ethyl 2-ethoxy-4-[N-(2-piperidino-α-(tetrahydrofuran-2-yl-methyl)-benzyl)-aminocarbonylmethyl]-benzoate Prepared analogously to Example 19 from 2-piperidino-α-(tetrahydrofuran-2-yl-methyl)-benzylamine and 3-ethoxy-4-ethoxycarbonyl-phenyl-acetic acid.

Melting point: 111–113° C.; Calculated: C, 70.84; H, 7.93; N, 5.51; Found: 70.76; 7.73; 5.51.

EXAMPLE 87

2-Ethoxy-4-[N-(2-piperidino-α-(tetrahydrofuran-2-ylmethyl)-benzyl)-aminocarbonylmethyl]-benzoic acid Prepared analogously to Example 21 by alkaline saponification of ethyl 2-ethoxy-4-[N-(2-piperidino-α-(tetrahydrofuran-2-yl-methyl)-benzyl)-aminocarbonylmethyl]-benzoate.

Melting point: 121–123° C.; Calculated: C, 69.98; H, 7.55; N, 5.83; Found: 69.90; 7.78; 5.71.

EXAMPLE 88

Ethyl 2-ethoxy-4-[N-(α-cycloheptylmethyl-2-piperidino-benzyl)-aminocarbonylmethyl]-benzoate Prepared analogously to Example 19 from α-cycloheptylmethyl-benzylamine and 3-ethoxy-4-ethoxycarbonyl-phenylacetic acid.

Melting point: 96–98° C.; Calculated: C, 74.12; H, 8.67; N, 5.24; Found: 74.40; 8.87; 5.39.

EXAMPLE 89

2-Ethoxy-4-[N-(α-cycloheptylmethyl-2-piperidino-benzyl)-aminocarbonylmethyl]-benzoic acid Prepared analogously to Example 21 by alkaline saponification of ethyl 2-ethoxy-4-[N-(α-cycloheptylmethyl-2-piperidino-benzyl)-aminocarbonylmethyl]-benzoate.

Melting point: 127–130° C.; Calculated: C, 73.49; H, 8.36; N, 5.53; Found: 73.54; 8.62; 5.47.

EXAMPLE 90

Ethyl 2-ethoxy-4-[N-(α-cyclohexylmethyl-2-piperidino-benzyl)-aminocarbonylmethyl]-benzoate
a) Ethyl 2-ethoxy-4-[N-(α-(cyclohexyl-methylidene)-2-piperidino-benzyl)-aminocarbonylmethyl]-benzoate Prepared analogously to Example 19 from α-cyclohexylmethyl-(2-piperidino-phenyl)-ketimine and 3-ethoxy-4-ethoxycarbonyl-phenylacetic acid.

Melting point: 85–88° C.; Calculated: C, 74.10; H, 8.16; N, 5.10; Found: 74.37; 8.00; 5.45.

According to the 80 MHz-$^1$H-NMR spectrum ($CDCl_3$) there is a mixture of E/Z=½. [Olefinic H: (E) D 6.26, (Z) 5.42 ppm].
b) Ethyl 2-ethoxy-4-[N-(α-cyclohexylmethyl-2-piperidino-benzyl)-aminocarbonylmethyl]-benzoate Prepared analogously to Example 12 by catalytic hydrogenation of ethyl 2-ethoxy-4-[N-(α-(cyclohexyl-methylidene)-2-piperidino-benzyl)-aminocarbonylmethyl]-benzoate Melting point: 95–97° C.; Calculated: C, 73.81; H, 8.52; N, 5.38; Found: 73.92; 8.74; 5.29.

EXAMPLE 91

2-Ethoxy-4-[N-(α-cyclohexylmethyl-2piperidino-benzyl)-aminocarbonylmethyl)-benzoic acid a) 2-Ethoxy-4-(α-(cyclohexyl-methylidene)-2-piperidino-benzyl)-aminocarbonylmethyl]-benzoic acid Prepared analogously to Example 21 by alkaline saponification of ethyl 2-ethoxy-4-[N-(α-(cyclohexyl-methylidene)-2-piperidino-benzyl)-aminocarbonylmethyl]-benzoate.

Melting point: 95–100° C.; Calculated: C, 73.44; H, 7.81; N, 5.71; Found: 73.38; 7.73; 5.75.

b) 2-Ethoxy-4-[N-(α-cyclohexylmethyl-2-piperidino-benzyl)-aminocarbonylmethyl]-benzoic acid Prepared analogously to Example 12 by catalytic hydrogenation of 2-ethoxy-4-[N-(α-(cyclohexyl-methylidene)-2-piperidino-benzyl)-aminocarbonylmethyl]-benzoic acid.

Melting point: 154–156° C.; Calculated: C, 73.14; H, 8.18; N, 5.69; Found: 73.31; 8.25; 5.71.

EXAMPLE 92

Ethyl 2-ethoxy-4-[N-(1-(2-piperidino-phenyl)-3-buten-1-yl)-aminocarbonylmethyl]-benzoate Prepared analogously to Example 19 from 1-(2-piperidino-phenyl)-3-buten-1-yl-amine and 3-ethoxy-4-ethoxycarbonyl-phenylacetic acid.

Melting point: 110–112° C.; Calculated: C, 72.39; H, 7.81; N, 6.03; Found: 72.10; 7.66; 5.94.

EXAMPLE 93

2-Ethoxy-4-[N-(1-(2-piperidino-phenyl)-3-buten-1-yl)-aminocarbonylmethyl]-benzoic acid Prepared analogously to Example 21 by alkaline saponification of ethyl 2-ethoxy-4-[N-(1-(2-piperidino-phenyl)-3-buten-1-yl)-aminocarbonylmethyl]-benzoate.

Melting point: 92–95° C.; Calculated: C, 71.53; H, 7.39; N, 6.42; Found: 71.27; 7.42; 6.42.

EXAMPLE 94

Ethyl 2-ethoxy-4-[N-(1-(2-piperidino-phenyl)-3-methyl-3-buten-1-yl)-aminocarbonylmethyl]-benzoate Prepared analogously to Example 19 from 3-methyl-1-(2-piperidino-phenyl)-3-buten-1-yl)-amine and 3-ethoxy-4-ethoxycarbonyl-phenylacetic acid.

Melting point: 126–128° C.; Calculated: C, 72.77; H, 8.00; N, 5.65; Found: 72.82; 8.22; 5.78.

EXAMPLE 95

2-Ethoxy-4-[N-(1-(2-piperidino-phenyl)-3-methyl-3-buten-1-yl)-aminocarbonylrethyl]-benzoic acid Prepared analogously to Example 21 by alkaline saponification of ethyl 2-ethoxy-4-[N-(1-(2-piperidino-phenyl)-3-methyl-3-buten-1-yl)-aminocarbonylmethyl]-benzoate.

Melting point: 64–66° C.; Calculated: C, 71.97; H, 7.61; N, 6.22; Found: 71.70; 7.50; 5.98.

EXAMPLE 96

Ethyl 2-ethoxy-4-[N-(1-(2-piperidino-phenyl)-3-methyl-2-buten-1-yl)-aminocarbonylmethyl]-benzoate[with 25% of ethyl 2-ethoxy-4-[N-(1-(2-piperidino-phenyl)-3-methyl-1-butyl)-aminocarbonylmethyl]-benzoate]

Prepared analogously to Example 19 from 3-methyl-1-(2-piperidino-phenyl)-2-buten-1-yl-amine [containing 25% of 3-methyl-1-(2-piperidino-phenyl)-1-butylamine] and 3-ethoxy-4-ethoxycarbonyl-phenylacetic acid.

Melting point: 141–142° C.; Calculated: C, 72.77; H, 8.00; N, 5.85; Found: 72.60; 7.77; 5.73.

The mixing ratio of 75/25 is obtained from the corresponding ratio of intensities of the particularly characteristic signals in the 400 MHz-$^1$H-NMR spectrum (CDCl$_3$). The position of the signals is: 3-methyl-2-buten-1-yl compound: olefinic H: 5.25 (d), CH$_3$: 1.64 (s) and 1.77 (s), benzylic >CH— 6.00 (t). benzylic CH$_2$—: 3.52 ppm (s) 3-methyl-1-butyl compound: CH$_3$: 0.90 (d). benzylic >CH— 5.35 (m), benzylic —CH$_2$—: 3.54 ppm (s).

EXAMPLE 97

2-Ethoxy-4-[N-(1-(2-piperidino-phenyl)-3-methyl-2-buten-1-yl)-aminocarbonylmethyl]-benzoic acid [containing 25% of 2-ethoxy-4-[N-(1-(2-piperidino-phenyl)-3-methyl-1-butyl)-aminocarbonylmethyl]-benzoic acid]

Prepared analogously to Example 21 by alkaline saponification of the corresponding ethyl ester mixture from Example 58.

Melting point: 154–156° C.; Calculated: C, 71.97; H, 7.61; N, 6.22; Found: 71.80; 7.57; 5.98.

EXAMPLE 98

Ethyl 2-ethoxy-4-[N-(1-(2-piperidino-phenyl)-3-butyn-1-yl)-aminocarbonylmethyl]-benzoate Prepared analogously to Example 19 from 1-(2-piperidino-phenyl)-3-butyn-1-yl-amine and 3-ethoxy-4-ethosycarbonyl-phenylacetic acid.

Melting point: 86–90° C.; Calculated: C, 72.70; H, 7.41; N, 6.06; Found: 72.60; 7.40; 6.04.

EXAMPLE 99

2-Ethoxy-4-[N-(1-(2piperidino-phenyl)-3-butyn-1-yl)-aminocarbonyl-methyl]-benzoic acid Prepared analogously to Example 21 by alkaline saponification of ethyl 2-ethoxy-4-[N-(1-(2-piperidino-phenyl)-3-butyn-1-yl)-aminocarbonylmethyl]-benzoate.

Melting point: 66–69° C.; Calculated: C, 71.87; H, 6.96; N, 6.45; Found: 71.60; 6.95; 6.38.

EXAMPLE 100

Ethyl 2-ethoxy-4-[N-(1-(2-piperidino-phenyl)-4-penten-1-yl)-aminocarbonylmethyl]-benzoate Prepared analogously to Example 19 from 1-(2-piperidino-phenyl)-4-penten-1-yl-amine and 3-ethoxy-4-ethoxycarbonyl-phenylacetic acid.

Melting point: 117–120° C.; Calculated: C, 72.77; H, 8.00; N, 5.85; Found: 72.73; 7.97; 6.07.

EXAMPLE 101

2-Ethoxy-4-[N-(1-(2-piperidino-phenyl)-4-penten-1-yl)-aminocarbonylmethyl]-benzoic acid Prepared analogously to Example 21 by alkaline saponification of ethyl 2-ethoxy-4-[N-(1-(2-piperidino-phenyl)-4-penten-1-yl)-aminocarbonylmethyl benzoate.

Melting point: 82–85° C.; Calculated: C, 71.97; H, 7.61; N, 6.22; Found: 71.97; 7.59; 5.98.

EXAMPLE 102

Ethyl 2-ethoxy-4-[N-(1-(2-piperidino-α-(tetrahydropyran-2-yl-methyl)-benzyl)-aminocarbonyl-methyl]-benzoate Prepared analogously to Example 19 from 2-piperidino-α-(tetrahydropyran-2-yl-methyl)-benzylamine and 3-ethoxy-4-ethoxycarbonyl-phenylacetic acid.

Melting point: 82–85° C.; Calculated: C, 71.24 98.10; N, 5.36; Found: 71.28; 7.96; 5.29.

EXAMPLE 103

2-Ethoxy-4-[N-(1-(2-piperidino-α-(tetrahydropyran-2-yl-methyl)-benzyl)-aminocarbonylmethyl]benzoic acid Prepared analogously to Example 21 by alkaline saponification of ethyl 2-ethoxy-4-[N-(1-(2-piperidino-α-(tetrahydropyran-2-yl-methyl)-benzyl-aminocarbonyl-methyl]-benzoate.

Melting point: 140–142° C. (sinters from 70° C., partial softening at 105° C.); Calculated C, 70.42; H, 7.74; N, 5.66; Found H 7.88; N, 5.40

Ethyl 2-ethoxy-4-[N-(α-cyclohexylmethyl-2-piperidino-benzyl)-aminocarbonylmethyl]-benzoate At 23–25° C., a solution of ethyl 2-ethoxy-4-cyanomethyl-benzoate (2.35 g, 10 mmol) and α-cyclohexylmethyl-2-piperidino-benzyl alcohol(2.88 g, 10 mmol) in o-dichlorobenzene (15 ml) is added dropwise to a mixture of concentrated sulphuric acid (15 ml) and o-dichlorobenzene (15 ml). The mixture is stirred for 2 hours at ambient temperature. The o-dichlorobenzene phase is then separated off and the residue is added to ice. After being made alkaline with soda solution, it is extracted with chloroform. The extracts are dried over sodium sulphate and concentrated by evaporation. The residue is purified by column chromatography on silica gel (toluene/acetone=10/1).

Yield: 1.1 g Melting point: 95–97° C.; Calculated: C, 73.81; H, 8.52; N, 5.38; Found: 73.95; 8.64; 5.42.

EXAMPLE 105

Benzyl 2-ethoy-4-[N-(αmethoxycarbonyl-2piperidino-benzyl)-aminocarbonylmethyl]-benzoate Potassium carbonate (2.28 g, 2 mmol) is added to a solution of benzyl 2-ethoxy-4-[N-(α-carboxy-2-piperidino-benzyl)-aminocarbonylmethyl]-benzoate (1.06 g, 2 mmol) in anhydrous dimethyl formamide (i ml). The mixture is stirred for 10 minutes at ambient temperature, then methyl iodide (0.125 ml, 2 mmol) is added and the resulting mixture is stirred overnight at ambient temperature. It is filtered and the filtrate is concentratedby evaporation to dryness in vacuo. The evaporation residue is partitioned between aqueous sodium bicarbonate solution (pH-g) and methylene chloride. The organic phase was poured over sodium sulphate, filtered and concentrated by evaporation in vacuo. The evaporation residue is purified by column chromatography on silica gel (toluenelacetone=4/1) and crystallized from ether/petroleum ether.

Yield: 0.56 g; Melting point: 100–102° C.; Calculated: C, 70.57; H, 6.66; N, 5.14; Found: 70.69; 6.71; 5.29.

EXAMPLE 106

(S) 2-Ethoxy-4-[N-(1-(2-piperidino-phenyl)-3-methyl-1-butyl)-aminocarbonylmethyl]benzoic acid
a) (S)-3-Methyl-1-(2-piperidino-phenyl)-1-butylamine Equimolar quantities of racemic 3-methyl-1-(2-piperidino-phenyl)-1-butylamine and of N-acetyl-L-glutamic acid were refluxed in aceton, whereby methanol was added in such an amount to yield a clear solution.

After cooling over night up to 20° C., the obtained crystals were suction filtered and twice washed with aceton cooled to −15° C. The obtained product [M.p.: 163–166° C.; $[\alpha]_D^{20}$=+ 0,286° (c=1 in methanol)] was recrystallised from aceton under addition of methanol, whereby (S)-3-methyl-1-(2-piperidino-phenyl)-1-butylamine as N-acetyl-L-glutamic acid addition salt was obtained in a yield of 60,4% of theory.

M.p.: 168–171° C.; $[\alpha]_{20}^D$=+0,356° (c=1 in methanol)

The free amine was obtained after reacting with sodium hydroxide solution.

b) (S) Ethyl 2-ethoxy-4-[N-(1-(2-piperidino-phenyl)-3-methyl-1-butyl)-aminocarbonylmethyl]benzoate Prepared from (S)-3-Methyl-1-(2-piperidino-phenyl)-1-butyl-amine and 3-ethoxy-4-ethoxycarbonyl-phenylacetic acid analogously to Example 1.

Yield: 77% of theory, M.p.: 121–123° C. (petroleum ether/aceton =7/1), $[\alpha]_D^{20}$=+7.82° (c=1 in methanol)

c) (S) 2-Ethoxy-4-[N-(1-(2-piperidino-phenyl)-3-methyl-1-butyl)-aminocarbonylmethyl]benzoic acid Prepared from (S) Ethyl 2-ethoxy-4-[N-(1-(2-piperidino-phenyl)-3-methyl-1-butyl)-aminocarbonylmethyl)benzoate by saponification analogously to Example 4.

Yield: 75,9% of theory, M.p.: 102–104° C. (petroleum ether/toluene), $[\alpha]_{20}^D$=+7.80° (c=1,025 in methanol).

The compounds of the present invention, that is, those embraced by formula I above, including forms (A), (3) and (C) of 2-ethoxy-4-[N-(1-(2-piperidino-phenyl)-3-methyl-1-butyl}-aminocarbonylmethyl]-benzoic acid, their enantiomers and the non-toxic, pharmacologically acceptable salts formed with inorganic or organic acids or bases, have useful pharmacodynamic properties. More particularly, they have a favorable effect on the intermediate metabolism and exhibit hypoglycemic activity in warm-blooded animals such as rats.

The hypoglycemic activity of the compounds of the instant invention was ascertained by the standard pharmacological test method described below, and the table which follows shows the results of this test for a few represents species of the genus, where A=2-methoxy-4-[N-{1-(2-piperidino-phenyl)-1-ethyl}-aminocarbonylmethyl]-benzoic acid, B=2-ethoxy-4-[N-{1-(2-piperidino-phenyl)-1-butyl}-aminocarbonylmethyl]-benzoic acid, C=2-methoxy-4-[N-(α-phenyl-2-piperidino-benzyl)-aminocarbonymethyl]-benzoic acid, D=2-ethoxy-4-[N-(α-phenyl-2-piperidino-benzyl)-aminocarbonylmethyl]-benzoic acid, E=(+)-2-ethoxy-4-[N-{1-(2-piperidino-phenyl)-1-butyl}-aminocarbonylmethyl]-benzoic acid, F=2-ethoxy-4-[N-{1-(2-piperidino-phenyl)-1-ethyl}-aminocarbonylmethyl]-benzoic acid, G=sodium 2-ethoxy-4-[N-{1-(2-pyrrolidino-phenyl)-1-butyl}-aminocarbonylmethyl]-benzoate, H=2-ethoxy-4-[N-{1-(2-hexamethyleneimino-phenyl)-1-butyl}-aminocarbonylmethyl]-benzoic acid, I=2-methoxy-4-[N-{1-(2-piperidino-phenyl)-1-butyl}-aminocarbonylmethyl]-benzoic acid, K=2-n-propoxy-4-[N-{1-(2-piperidino-phenyl)-1-butyl}-aminocarbonylmethyl]-benzoic acid, L=2-ethoxy-4-[N-{1-(2-piperidino-phenyl)-1-pentyl}-aminocarbonylmethyl]-benzoic acid, M=2-ethoxy-4-[N-(4-methyl-α-phenyl1-2-piperidino-benzyl)-aminocarbonylmethyl]-benzoic acid, N=from (B) of 2-ethoxy-4-[N-{1-(2-piperidino-phenyl)-3-methyl-1-butyl}-aminocarbonylmethyl]-benzoic acids O=[2-ethoxy-4-[N-(1-(2-piperidino-phenyl)-1-butyl)-aminocarbonylmethyl]-phenyl]-acetonitrile, P=[2-ethoxy-4-[N-(α-phenyl-2-piperidino-benzyl)-aminocarbonylmethyl]-phenyl]acetonitrile, Q=2-ethoxy-4-[N-(α-cyclohexylmethyl-2-piperidino-benzyl)-aminocarbonyl-methyl]-benzoic acid, R=2-ethoxy-4-[N-(α-ethoxycarbonyl-2-piperidino-benzyl)-aminocarbonylmethyl]-benzoic acid, S=2-ethoxy-4-[N-(α-methoxycarbonyl-2-piperidino-benzyl)-aminocarbonylmethyl]-benzoic acid, T=2-ethoxy-4-[N-(α-isopropoxycarbonyl-2-piperidino-benzyl)-aminocarbonylmethyl]benzoic acid, U=2-ethoxy-4-[N-(α-cyclopropylmethyl-2-piperidino-benzyl)-aminocarbonylmethyl]benzoic acid, V=2-ethoxy-4-[N-(α-(tetrahydrofuran-2-yl-methyl)-2-piperidino-benzyl)-aminocarbonylmethyl]benzoic acid, W=2-ethoxy-4-[N-(1-(2-piperidino-phenyl)-3-buten-1-yl)-aminocarbonylmethyl]benzoic acid, X=2-ethoxy-4-[N-(1-(2-piperidino-phenyl)-3-methyl-3-buten-1-yl)-aminocarbonylmethyl]benzoic acid and Y=2-ethoxy-4-[N-(1-(2-piperidino-phenyl)-3-butyn-1-yl)-aminocarbonylmethyl]benzoic acid, Test for Hypoglycemic Activity The hypoglycemic activity of the test compounds was ascertained on female rats of a particular strain weighing from 180–220 g which had been fasted for 24 hours before the start of the test. The test compounds were suspended in 1.5% methyl cellulose immediately before the start of the test and administered by esophageal tube.

Blood samples were taken immediately before the administration of the test compound and 1, 2, 3 and 4 hours afterwards, in each case from the retroorbital Venous plexus. 50 μl of each sample were deproteinated with 0.5 ml of 0.33 N perchloric acid and centrifuged. The glucose in the supernatant fluid was measured using the hexokinase method with the aid of an analytical photometer. The statistical evaluation was made using the t-test according to Student with p=0.05 as the limit of significance.

The following tables show the change in glucose content in percent compared with the control:

TABLE I

| Compound | 1 mg/kg | | | | 0.5 mg/kg | | | |
|---|---|---|---|---|---|---|---|---|
|  | 1 | 2 | 3 | 4 h | 1 | 2 | 3 | 4 h |
| A | −37 | −46 | −23 | −14 | | | | |
| B | −38 | −49 | −38 | −33 | −43 | −36 | −34 | −35 |
| C | −38 | −41 | −38 | −34 | | | | |
| D | −42 | −54 | −37 | −34 | | | | |
| E | | | | | −40 | −39 | −36 | −36 |
| F | −44 | −44 | −40 | −30 | | | | |
| G | | | | | −40 | −33 | −30 | −17 |
| H | | | | | −42 | −34 | −18 | n.s. |
| I | | | | | −42 | −39 | −37 | −30 |
| K | | | | | −34 | −36 | −24 | n.s. |
| L | | | | | −42 | −45 | −38 | −39 |
| M | −44 | −41 | −35 | −27 | | | | |
| O | −29 | −37 | −35 | −34 | | | | |
| P | −12 | −10 | −14 | −14 | | | | |

TABLE I-continued

| Compound | 1 mg/kg | | | | 0.5 mg/kg | | | |
|---|---|---|---|---|---|---|---|---|
|  | 1 | 2 | 3 | 4 h | 1 | 2 | 3 | 4 h |
| Q | | | | | −22 | −47 | −45 | −45 |
| R | −33 | −17 | n.s. | n.s. | | | | |
| S | −42 | −35 | −28 | −18 | | | | |
| T | −36 | −21 | −18 | n.s. | | | | |
| U | | | | | −45 | −45 | −36 | −36 |
| V | | | | | −46 | −25 | −13 | −10 |
| W | | | | | −42 | −39 | −28 | −35 |
| X | | | | | −44 | −41 | −31 | −28 |
| Y | | | | | −33 | −18 | −11 | n.s. | n.s. = not statistically significant

TABLE II

| Compound | 0.1 mg/kg | | | |
|---|---|---|---|---|
|  | 1 | 2 | 3 | 4 h |
| N | −38 | −44 | −41 | −40 |

In the tests for hypoglycemic activity, no toxic side effects were observed, even at a dosage of 10 mg/kg p.o., with any of these compounds.

The novel compounds are virtually non-toxic; for example, after a single dose of 2,000 mg/kg p.o. (suspension in 1% methyl cellulose) of compounds 3 and D to 5 male and 5 female mice, only one animal in this group died during the observation period of 14 days.

The toxic effect of a single dose of compound N administered orally (suspended in 1% methyl cellulose) was tested in male and female mice of our own strain weighing from 20–26 g over an observation period of 14 days.

TABLE III

| Compound | Approximate acute toxicity |
|---|---|
| N | >1000 mg/kg p.o. (0 out of 6 animals died) |

By virtue of their pharmacological properties, the compounds of the present invention are useful for the treatment of diabetes mellitus.

For pharmaceutical purposes the compounds of the present invention are administered to warm-blooded animals perorally or parenterally as active ingredients in customary pharmaceutical compositions, that is, compositions consisting essential of an inert pharmaceutical carrier and an effective amount of the active ingredient, such as tablets, coated pills, capsule wafers, powders, solutions, suspensions, emulsions, syrups and the like. An effective amount of the compounds of the present invention is from 0.014 to 0.71 mgm/kg body weight, preferably 0.035 to 0.29 mgm/kg body weight, once or twice daily.

The following examples illustrate a few pharmaceutical compositions comprising a compound of the present invention as an active ingredient and represent the best modes contemplated of using the invention. The parts are parts by weight unless otherwise specified.

EXAMPLE 107

Tablets containing 5 mg of 2-ethoxy-4-[N-{1-(2-piperidino-phenyl)-3-methyl-1-butyl}-aminocarbonylmethyl]-benzoic acid, form (B)

The tablet composition is compounded from the following ingredients:

| Active ingredient | (1) | 5.0 parts |
|---|---|---|
| Corn starch | (2) | 62.0 parts |
| Lactose | (3) | 48.0 parts |
| Polyvinylpyrrolidone | (4) | 4.0 parts |
| Magnesium stearate | (5) | 1.0 parts |
| | | 120.0 parts |

Preparation:

Ingredients (1), (2), (3) and (4) are mixed together and moistened with water. The moist mixture is passed through a 1.5 ma mesh screen and dried at about 45° C. The dry granular is passed through a 1.0 mm mesh screen and mixed with ingredient (5). The finished mixture is compressed into 120 mg-tablets.

EXAMPLE 108

Coated tablets containing 2.5 mg of 2-ethoxy-4-[N-{1-(2-piperidino-phenyl)-3-methyl-1-butyl}-aminocarbonylmethyl]-benzoic acid, form (A)

The tablet core composition is compounded from the following ingredients:

| Active ingredient | (1) | 2.5 parts |
|---|---|---|
| Potato starch | (2) | 44.0 parts |
| Lactose | (3) | 30.0 parts |
| Polyvinylpyrrolidone | (4) | 3.0 parts |
| Magnesium stearate | (5) | 0.5 parts |
| | | 80.0 parts |

Preparation:

Ingredients (1), (2), (3) and (4) are thoroughly mixed and moistened with water. The moist mass is passed through a 1 mm-mesh screen, dried at about 45° C., and the granulate is then passed through the same screen. After ingredient (5) has been added, convex 80 mg-tablet cores are compressed in a tablet-making machine. The tablet cores thus produced are covered in known manner with a coating consisting essentially of sugar and talc. The finished tablets are polished with wax Weight of each coated tablet: 120 mg.

EXAMPLE 109

Tablets containing 10 mg of 2-ethoxy-4-[N-(α-phenyl-2-piperidino-benzyl)-aminocarbonylmethyl]-benzoic acid The tablet composition is compounded from the following ingredients:

| Active ingredient | 10.0 parts |
|---|---|
| Powdered lactose | 70.0 parts |
| Corn starch | 31.0 parts |
| Polyvinylpyrrolidone | 8.0 parts |
| Magnesium stearate | 1.0 parts |
| | 120.0 parts |

Preparation:

The mixture of active ingredient, lactose and corn starch is moistened with a 20% solution of polyvinylpyrrolidone in water. The moist mass is passed through a 1.5 mm mesh screen and dried at 45° C. The dried granulate is passed through a 1 mm mesh screen and is homogeneously mixed with magnesium stearate. The composition is compressed into 120 mg-tablets.

EXAMPLE 110

Coated tablets containing 5 mg of 2-ethoxy-4-[N-{1-(2-piperidino-phenyl)-3-methyl-1-butyl}-aminocarbonylmethyl]-benzoic acid The tablet core composition is compounded from the following ingredients:

| Active ingredient | 5.0 parts |
|---|---|
| Secondary calcium phosphate | 70.0 parts |
| Corn starch | 50.0 parts |
| Polyvinylpyrrolidone | 4.0 parts |
| Magnesium stearate | 1.0 parts |
| | 130.0 parts |

Preparation:

The mixture of active ingredient, calcium phosphate and corn starch is moistened with a 15% solution of polyvinylpyrrolidone in water. The moist mass is passed through a 1 mm mesh screen, dried at 45° C. and then passed through the same screen. After adding the magnesium stearate, 130 mg-tablet cores are compressed from the mixture.

A coating of sugar and talc is applied in known manner to the cores thus produced. The finished coated tablets are polished with wax.

Weight of coated tablet: 180 mg.

Any one of the other compounds embraced by formula I, including forms (A), (B) and (C) of 2-ethoxy-4-[N-{1-(2-piperidino-phenyl)-3-methyl-1-butyl}-aminocarbonylmethyl]-benzoic acid, an enantiomer thereof or a non-toxic, pharmacologically acceptable salt thereof may be substituted for the particular active ingredient in Examples 29 through 32. Likewise, the amount of active ingredient in these illustrative examples may be varied to achieve the dosage unit range set forth above, and the amounts and nature of the inert pharmaceutical carrier ingredients may be varied to meet particular requirements.

EP-B-147850 describes inter alia the racemate of 2-ethoxy-4-[N-[1-(2-piperidino-phenyl)-3-methyl-1-butyl] aminocarbonylmethyl]-benzoic acid (Code No.: AG-EE 388 ZW) of the formula

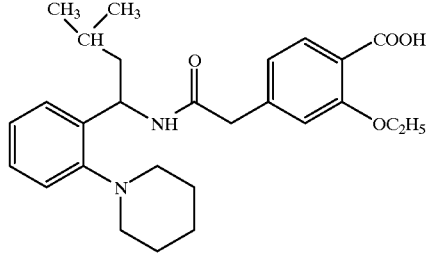

and EP-B-207331 describes two other polymorphous forms of this compound. This compound and the physiologically acceptable salts thereof have valuable pharmacological properties, namely an effect on the intermediate metabolism, but more particularly the effect of lowering blood sugar.

The two enantiomers of this compound, namely (S)(+)-2-ethoxy-4-[N-[1-(2-piperidino-phenyl)-3-methyl-1-butyl] aminocarbonylmethyl]-benzoic acid (Code No.: AG-EE 623 ZW) and (R)(−)-2-ethoxy-4-[N-[1-(2-piperidino-phenyl)-3- methyl-1-butyl]aminocarbonylmethyl]-benzoic acid (Code No.: AG-EE 624 ZW) have been tested for their blood sugar-lowering effect on female rats, bred by the applicants, weighing 180 to 220 g which had been kept fasting 24 hours before the start of the experiment. The substances to be investigated were suspended in 1.5% methylcellulose immediately before the start of the test and administered into the oesophagus.

Blood samples were taken immediately before administration of the substance and 1, 2, 3, 4, 5 and 6 hours thereafter, from the retroorbital venous plexus, in each case. 50 μl of blood were deproteinated with 0.5 ml of 0.33 N perchloric acid and centrifuged. Glucose was measured in the supernatant by the hexokinase method using an analytical photometer. The statistical evaluation was carried out using the Student's t-test with p=0.05 as the limit of significance.

Table 1 which follows contains the statistically significant values as percentage deviations from the control:

TABLE 1

| Substance | 1 | 2 | 3 | 4 | 5 | 6 hours |
|---|---|---|---|---|---|---|
| AG-EE 623 ZW 0.015 mg/kg p.o. | −17 | −36 | −37 | −32 | −35 | −35 |
| AG-EE 624 ZW 1.0 mg/kg p.o. | n.s. | n.s. | n.s. | n.s. | — | — | n.s. = statistically not significant
— = not measured

It is found that the (S)-enantiomer (AG-EE 623 ZW) is the effective enantiomer and its effect lasts longer than 6 hours in the rat.

On the basis of these findings in the rat, it seems appropriate to use exclusively AG-EE 623 ZW in humans, thereby reducing the dose by 50%, compared with the dose of AG-EE 388 ZW. This has been confirmed in humans, as explained hereinafter. However, it was also found in the human studies that AG-EE 623 ZW has surprising pharmacokinetic properties which could not have been foreseen on the basis of the AG-EE 388 ZW data. AG-EE 623 ZW thus has surprising therapeutic advantages over the racemate AG-EE 388 ZW.

More specifically, the studies which follow were carried out on healthy male volunteers in whom the levels of glucose and active substance in the course of time were determined:

In study 1 (randomised, double blind, group comparison), 12 test subjects, in a fasting state, were given in the morning a placebo capsule or a capsule containing 2 mg of micronised AG-EE 388 ZW. 5.5 hours after oral administration, a standard lunch (L) was eaten, 7 hours after administration a snack (S) was eaten and LO hours after administration a standard evening meal (D) was eaten. Blood samples were taken at different times. The glucose concentrations were determined from whole blood using the hexokinase method (see above). The concentrations of AG-EE 388 ZW were determined from the plasma using a non-stereoselective HPLC method with electrochemical detection and a detection limit of 5 ng/ml (see A. Greischel, K. Beschke, H. Rapp and W. Roth in Journal of Chromatography, Biomedical Applications entitled "Quantitation of the New Hypoglycemic Agent AG-EE 388 ZW in Human Plasma by Automated High-Performance Liquid Chromatography with Electrochemical Detection"; submitted).

Table 2 which follows contains the average glucose levels found in the subject group as a percentage deviation from the placebo group as well as the average AG-EE 388 ZW concentrations in ng/ml together with the standard deviation (SD) in the subject group.

TABLE 2

| (Study 1) | | | |
|---|---|---|---|
| Time after administration | Glucose [%] deviation | Concentration AG-EE 388 ZW [ng/ml] | |
| [hours] | from placebo | mean | SD |
| 0 | n.s. | 0.0 | 0.0 |
| 0.50 | n.s. | 55.8 | 32.9 |
| 0.75 | −9 | 82.9 | 17.9 |
| 1.00 | −17 | 82.8 | 15.3 |
| 1.50 | −27 | 64.7 | 8.2 |
| 2.00 | −24 | 58.3 | 12.0 |
| 2.50 | −19 | — | — |
| 3.00 | n.s. | 29.4 | 7.6 |
| 4.00 | −24 | 16.3 | 6.9 |
| 5.00 | −9 | 9.0 | 6.2 |
| 5.50-(L) | n.s. | — | — |
| 6.00 | n.s. | 4.2 | 4.5 |
| 7.00-(S) | n.s. | — | — |
| 8.00 | −5 | 1.2 | 2.9 |
| 9.00 | n.s. | — | — |
| 10.00-(D) | n.s. | 0.0 | 0.0 | n.s. = statistically not significant
— = not measured
(L) = lunch
(S) = snack
(D) = dinner It is found that the level of active substance reaches the detection limit after 5 hours and that the duration of activity of AG-EE 388 ZW is about 5 hours. There is thus a good correlation between the plasma level curve of AG-EE 388 ZW and the blood sugar-lowering effect.

In study 2 (randomised, open, crossover) 12 test subjects, in a fasting state, were given in the morning either a capsule containing 2 mg of micronised AG-EE 388 ZW or a spray-dried tablet containing 2 mg of AG-EE 388 ZW. 2 hours after oral administration a standard breakfast (B) was eaten, 5 hours after administration a standard lunch (L) was eaten and 10.5 hours after administration a standard evening meal (D) was eaten. Blood samples were taken at various times. The glucose was measured in whole blood and the concentration of the active substance was measured in the plasma as in study 1.

Table 3 which follows contains the average glucose levels found in mmol/l after administration of capsules or tablets together with the standard deviations and the average AG-EE 388 ZW concentrations in ng/ml together with the standard deviations (SD).

TABLE 3

| (Study 2) | | | | | | | | |
|---|---|---|---|---|---|---|---|---|
| Time after administration | Glucose [mmol/l] | | | | Concentration AG-EE 388 ZW [ng/ml] | | | |
| | Capsule | | Tablet | | Capsule | | Tablet | |
| [hours] | mean | SD | mean | SD | mean | SD | mean | SD |
| 0 | 5.0 | 0.2 | 4.9 | 0.3 | 0.0 | 0.0 | 0.0 | 0.0 |
| 0.20 | 5.0 | 0.3 | 5.0 | 0.4 | 0.9 | 3.1 | 15.0 | 14.3 |
| 0.33 | 4.9 | 0.3 | 4.9 | 0.4 | 17.5 | 12.3 | 55.6 | 36.0 |
| 0.50 | 4.8 | 0.3 | 4.6 | 0.5 | 44.9 | 21.5 | 75.6 | 34.6 |
| 0.75 | 4.6 | 0.3 | 4.4 | 0.5 | 66.4 | 20.6 | 83.5 | 25.5 |
| 1.00 | 4.4 | 0.4 | 4.1 | 0.5 | 73.7 | 15.5 | 81.3 | 22.5 |
| 1.50 | 3.9 | 0.6 | 3.8 | 0.4 | 65.1 | 16.9 | 65.9 | 17.5 |
| 2.00-(B) | 3.7 | 0.3 | 3.8 | 0.2 | 50.8 | 13.5 | 51.3 | 14.9 |

TABLE 3-continued (Study 2)

| Time after administration [hours] | Glucose [mmol/l] | | | | Concentration AG-EE 388 ZW [ng/ml] | | | |
|---|---|---|---|---|---|---|---|---|
| | Capsule | | Tablet | | Capsule | | Tablet | |
| | mean | SD | mean | SD | mean | SD | mean | SD |
| 3.00 | 4.4 | 1.0 | 4.7 | 0.9 | 27.9 | 8.1 | 32.4 | 12.8 |
| 4.00 | 4.0 | 0.6 | 4.2 | 0.3 | 16.8 | 5.1 | 19.1 | 8.0 |
| 5.00-(L) | 4.2 | 0.4 | 4.2 | 0.5 | 12.2 | 3.4 | 13.2 | 6.1 |
| 6.00 | 4.8 | 0.8 | 5.2 | 0.7 | 7.8 | 4.3 | 9.5 | 5.7 |
| 9.00 | 5.0 | 0.3 | 5.0 | 0.5 | 3.3 | 3.5 | 5.2 | 3.6 |
| 10.50-(D) | — | — | — | — | — | — | — | — |
| 24.00 | 4.9 | 0.2 | 4.8 | 0.2 | 0.0 | 0.0 | 0.0 | 0.0 |

— = not measured

The AG-EE 388 ZW-level rises rather more rapidly after administration of the tablet and reaches its peak somewhat earlier than after administration of a capsule. The detection limit of AG-EE 398 ZW is reached after about 6 hours. In accordance with the plasma level curve the blood sugar-lowering effect sets in rapidly. The glucose levels return to their original level after 6 hours.

In study 3 (open, crossover) a single test subject in a fasting state took a capsule containing 2 mg or 4 mg of micronised AG-EE 388 ZW or 2 mg of AG-EE 623 ZW or a placebo capsule on four different days. The test subject continued to fast throughout the duration of the experiment. Blood samples were taken at different times. The glucose was measured in whole blood and the active substance concentration was determined in plasma according to study 1.

Table 4 which follows contains the glucose levels found as a percentage deviation from the level measured at time 0 and the active substance concentrations are shown in ng/ml.

AG-EE 623 ZW tends to set in more quickly (0.5 hours) than 4 mg of AG-EE 388 ZW (about 1.0 hour) and after 2 mg of AG-EE 623 ZW it reaches the maximum more quickly (1.5 hours) than after 4 mg of AG-EE 388 ZW (2.0 h). After the administration of 4 mg of AG-EE 388 ZW or 2 mg of AG-EE 623 ZW the blood sugar-lowering effect after reaching the peak slowly decreases virtually identically until the end of the test period is reached (8 hours). As is shown by a comparison with the placebo data, there still seems to be some blood sugar-lowering effect 8 hours after administration.

A look at the concentration of active substance gives the following picture: after the administration of 2 or 4 mg of AG-EE 388 ZW the maximum concentration of active substance is 82 or 150 ng/ml, respectively. The peaks are reached after 1.75 and 1.50 hours, respectively, i.e. rather earlier than the peak reductions in blood sugar after 2.0 hours. After 4 mg, 18 ng per ml of active substance can still be detected in the plasma 8 hours after administration. After the administration of 2 mg of AG-EE 623 ZW the maximum level is unexpectedly low at 22 to 24 ng/ml; it reaches only about one third of the level (82 ng/ml) which is found after the same dose of AG-EE 388 ZW. The level of active substance falls below the detection limit extremely quickly.

In order to check the results of study 3, particularly the low concentration of active substance and the surprisingly rapid fall in the active substance concentration (in view of the relatively long duration of effect) after the administration of AG-EE 623 ZW, study 4 was carried out (not randomised, open, double-blind at each dosage compared with placebo, group comparison). 6 test subjects in a fasting state were given in the morning 0.5 mg, 1.0 or 2.0 mg of AG-EE 623 ZW in the form of a spray-dried tablet or tablets or a placebo tablet or tablets prepared analogously. 0.25 hours after oral administration a standard breakfast (B) was eaten, 5.5 hours

TABLE 4

(Study 3)

| Time after administration [hours] | Glucose [%] deviation against t = 0 | | | | Active substance concentration [ng/ml] | | |
|---|---|---|---|---|---|---|---|
| | Placebo | 2 mg AG-EE 388 | 4 mg AG-EE 388 | 2 mg AG-EE 623 | 2 mg AG-EE 388 | 4 mg AG-EE 388 | 2 mg AG-EE 623 |
| 0 | 0 | 0 | 0 | 0 | — | 0 | — |
| 0.50 | −2 | 0 | −3 | −10 | 11 | 0 | — |
| 0.75 | 2 | 0 | −1 | −14 | 16 | 10 | — |
| 1.00 | −6 | −5 | −7 | −18 | 40 | 72 | — |
| 1.25 | 0 | −12 | −15 | −29 | 44 | 130 | 0 |
| 1.50 | −2 | −18 | −21 | −43 | 68 | 150 | 22 |
| 1.75 | −3 | −23 | −32 | −40 | 82 | 148 | 24 |
| 2.00 | −2 | −29 | −38 | −33 | 82 | 141 | 7 |
| 2.50 | −2 | −27 | −34 | −33 | 80 | 119 | 0 |
| 3.00 | 1 | −21 | −28 | −31 | 72 | 109 | 0 |
| 3.50 | −4 | — | −24 | — | 59 | 84 | 0 |
| 4.00 | 1 | −17 | −26 | −20 | 32 | 71 | 0 |
| 5.00 | −2 | −17 | −24 | −22 | 0 | 64 | — |
| 6.00 | −5 | −16 | −23 | −28 | — | 49 | 0 |
| 7.00 | −7 | — | −20 | −22 | — | 21 | 0 |
| 8.00 | −10 | — | −25 | −26 | — | 18 | — |

— = not measured

Table 4 shows that, as expected, 4 mg of AG-EE 388 ZW lower the blood glucose more sharply than 2 mg of AG-EE 388 ZW and that the maximum lowering after 4 mg of AG-EE 388 ZW (−38%) and after 2 mg of AG-EE 623 ZW (−43%) is virtually identical. However, the effect of 2 mg of after administration a standard lunch (L) was eaten and 10 hours after administration a standard evening meal (D) was eaten. Blood samples were taken at different times. The glucose concentrations were determined from whole blood according to study 1. The AG-EE 623 ZW concentrations in the plasma were determined by a stereospecific competitive enzyme immunoassay (ELISA) with a detection limit of 0.5 ng/ml.

The AG-EE 623 ZW-specific ELISA used is based on polyclonal rabbit antibodies directed against AG-EE 623 ZW covalently bound to human serum albumin. The cross reaction with AG-EE 624 ZW is less than 1:100. Microtitre immunoplates were coated with these antibodies and, after washing and blocking of the plates, incubated with standard or unknown plasma samples at 4° C. for one hour with shaking. Then AG-EE 623 ZW coupled to horse-radish peroxidase was added and incubated for a further 4 hours under the same conditions. 1,2-phenylenediamine was used as substrate for photometrically quantifying the bound enzyme-coupled molecules.

Table 5 which follows contains the average glucose levels found in the subject groups as a percentage deviation from the placebo group and the average AG-EE 623 ZW concentrations in ng/ml together with the standard deviations (SD) in the subject groups.

achieved 0.5 hours after administration. Compared with the AG-EE 388 ZW peak levels of 83.5±25.5 ng/ml (see Table 3) after the administration of one tablet containing 2 mg of AG-EE 388 ZW, the AG-EE 623 ZW maximum level of 50.4±26.3 ng/ml after the administration of one tablet containing 2 mg of AG-EE 623 ZW is significantly lower. The AG-EE 623 ZW plasma level is below the detection limit after only 3.0 hours (1 mg) or 4.0 hours (2 mg) after administration. [By comparison, the AG-EE 388 level does not fall below the detection limit for 6 hours after administration of a 2 mg tablet (see Table 3)].

Thus, the results of study 4 confirm the surprising findings of study 3:

(a) The AG-EE 623 ZW levels fall more rapidly towards zero than the AG-EE 388 ZW levels, even when the dose is absolutely identical, as can be seen from the following comparison (Table 6).

TABLE 5

(Study 4)

| Time after admin. of | Glucose [mmol/l] | | | | | | | | Concentration AC-EE 623 ZW [ng/ml] | | | | | |
|---|---|---|---|---|---|---|---|---|---|---|---|---|---|---|
| AG-EE 623 ZW | 0 mg | | 0.5 mg | | 1 mg | | 2 mg | | 0.5 mg | | 1 mg | | 2 mg | |
| (hours) | mean | SD | mean | SD | mean | SD | mean | SD | mean | SD | mean | SD | mean | SD |
| 0 | 4.96 | 0.16 | 5.21 | 0.23 | 4.62 | 0.06 | 4.67 | 0.13 | 0.0 | 0.0 | 0.0 | 0.0 | 0.0 | 0.0 |
| 0-25-(B) | 4.82 | 0.08 | 5.09 | 0.22 | 4.62 | 0.16 | 5.14 | 0.05 | 8.4 | 5.4 | 14.5 | 13.7 | 24.1 | 19.0 |
| 0.50 | 4.68 | 0.14 | 5.01 | 0.10 | 4.57 | 0.12 | 4.38 | 0.08 | 4.7 | 8.5 | 27.9 | 17.9 | 50.4 | 26.3 |
| 0.75 | 5.82 | 0.24 | 5.85 | 0.24 | 5.36 | 0.49 | 4.54 | 0.22 | 1.6 | 5.9 | 24.2 | 10.0 | 41.1 | 16.1 |
| 1.00 | 6.31 | 0.22 | 5.88 | 0.32 | 4.72 | 0.52 | 4.27 | 0.36 | 7.0 | 3.8 | 15.3 | 6.5 | 29.9 | 11.4 |
| 1.50 | 4.52 | 0.18 | 4.05 | 0.35 | 2.98 | 0.32 | 2.65 | 0.15 | 2.6 | 2.1 | 7.8 | 3.5 | 13.5 | 6.1 |
| 2.09 | 4.07 | 0.15 | 3.50 | 0.28 | 3.20 | 0.17 | 2.74 | 0.24 | 1.2 | 1.4 | 4.7 | 2.4 | 8.8 | 4.4 |
| 3.00 | 4.36 | 0.13 | 3.90 | 0.16 | 3.69 | 0.13 | 3.07 | 0.20 | 0.3 | 0.6 | 1.4 | 1.4 | 4.3 | 3.0 |
| 4.00 | 4.49 | 0.06 | 4.08 | 0.12 | 4.05 | 0.13 | 3.64 | 0.15 | 0.0 | 0.0 | 0.7 | 1.0 | 1.5 | 2.0 |
| 5.00 | 4.39 | 0.12 | 4.32 | 0.06 | 3.94 | 0.10 | 3.88 | 0.15 | 0.0 | 0.0 | 0.3 | 0.7 | 0.4 | 0.9 |
| 5.50-(L) | — | — | — | — | — | — | — | — | — | — | — | — | — | — |
| 6.00 | 6.74 | 0.15 | 6.63 | 0.27 | 6.48 | 0.28 | 6.47 | 0.35 | 0.0 | 0.0 | 0.3 | 0.7 | 0.2 | 0.6 |
| 8.00 | 5.39 | 0.39 | 5.61 | 0.33 | 5.37 | 0.21 | 4.61 | 0.27 | 0.0 | 0.0 | 0.0 | 0.0 | 0.0 | 0.0 |
| 10.00-(D) | 4.86 | 0.20 | 4.81 | 0.13 | 4.57 | 0.27 | 4.45 | 0.21 | 0.0 | 0.0 | 0.0 | 0.0 | 0.0 | 0.0 |
| 24.00 | 4.53 | 0.10 | 4.82 | 0.20 | 4.69 | 0.11 | 4.77 | 0.06 | 0.0 | 0.0 | 0.0 | 0.0 | 0.0 | 0.0 |

— = not measured

It is found that the lowering of blood sugar starts after 0.75 hours (2 mg) or after 1.0 (1 mg), reaches a peak after 1.5 hours and lasts for up to 2 hours (1 mg) or 5 hours (2 mg) after administration. The maximum levels of AG-EE 623 are (b) In relation to the lowering of blood sugar achieved, substantially lower plasma levels of AG-EE 623 ZW occur than might have been expected by halving the dosage of AG-EE 388 ZW.

TABLE 6

| Study No. | Substance AG-EE | Dose [mg] | Admin. form p.o. | Maximum concentration [ng/ml] | Concentration [ng/ml] | | |
|---|---|---|---|---|---|---|---|
| | | | | | 4 | 5 | 6 h |
| 1 | 388 | 2 | Capsule | 83 ± 18 | 16 ± 7 | 9 ± 6 | 4 ± 4 |
| 2 | 388 | 2 | Capsule | 74 ± 15 | 17 ± 5 | 12 ± 3 | 8 ± 4 |
| 2 | 388 | 2 | Tablet | 84 ± 25 | 19 ± 8 | 13 ± 6 | 10 ± 6 |
| 3 | 388 | 2 | Capsule | 82 | 32 | 0 | — |
| 3 | 388 | 4 | Capsule | 150 | 71 | 64 | 49 |
| 3 | 623 | 2 | Capsule | 24 | 0 | — | 0 |
| 4 | 623 | 1 | Tablet | 28 ± 18 | 0.7 ± 1.0 | 0.3 ± 0.7 | 0.3 ± 0.7 |
| 4 | 623 | 2 | Tablet | 50 ± 26 | 1.5 ± 2.0 | 0.4 ± 0.9 | 0.2 ± 0.6 |

The surprising results of studies 3 and 4 could be explained if the effective (S)-enantiomer (AG-EE 623 ZW) were eliminated from the blood unexpectedly much faster than the ineffective (R)-enantiomer (AG-EE 624 ZW). Then, when the racemate (AG-EE 388 ZW) is administered, the higher longer lasting plasma levels could be put down mainly to the ineffective (R)-enantiomer (AG-EE 624 W).

In the interests of more precise clarification, study 5 was carried out (randomised, open, crossover). 12 test subjects in a fasting state were each given in the morning 1 mg of AG-EE 388 ZW either as a 15 minute intravenous infusion or by oral route as a drinking solution or orally (micronised) in a capsule. 2 hours after administration a standard breakfast (B) was eaten, 5 hours after administration a standard lunch (L) was eaten and 10 hours after administration a standard dinner (D) was eaten. Blood samples were taken at different times. The glucose concentrations were measured in the plasma as in study 1. The AG-EE 388 ZW concentrations were measured in the plasma in accordance with study 1 using the non-stereoselective HPLC method and the AG-EE 623 ZW concentrations were measured in the plasma according to study 4 with the AG-EE 623 ZW-specific ELISA. The plasma concentrations of AG-EE 624 ZW were calculated as the difference between the two concentrations found:

$$AG\text{-}EE\ 624\ ZW = [C_{AG\text{-}EE\ 623\ ZW} + C_{AG\text{-}EE\ 624\ ZW}] - C_{AG\text{-}EE\ 623\ ZW}$$

Table 7 which follows contains the average plasma glucose levels measured in mmol/l together with standard deviations (SD), the average AG-EE 388 ZW concentration measured (388) and the average AG-EE 623 ZW concentration (623) including standard deviations (SD), as well as the average AG-EE 624 ZW concentration (624) calculated in ng/ml.

TABLE 7

(Study 5)

| Administration | Time after administration [hours] | Glucose [mmol/l] mean | SD | Concentration (ng/ml) (388) mean | SD | (623) mean | SD | (624)-calc. mean | SD |
|---|---|---|---|---|---|---|---|---|---|
| i.v. | 0.00 | 6.10 | 0.66 | 0.0 | 0.0 | 0.0 | 0.0 | 0.0 | 0.0 |
| | 0.08 | 6.54 | 0.75 | 33.3 | 12.9 | 14.1 | 6.6 | 19.2 | 8.6 |
| | 0.17 | 6.46 | 0.63 | 74.8 | 18.3 | 27.7 | 8.2 | 47.1 | 13.8 |
| | 0.25 | 6.46 | 0.70 | 103.8 | 23.6 | 34.2 | 8.5 | 69.7 | 17.5 |
| | 0.28 | 6.46 | 0.73 | 101.8 | 15.2 | 327.3 | 5.3 | 69.4 | 12.0 |
| | 0.33 | 6.40 | 0.76 | 85.6 | 15.0 | 22.9 | 4.6 | 62.9 | 11.6 |
| | 0.42 | 6.01 | 0.70 | 69.6 | 13.7 | 16.9 | 4.3 | 52.7 | 11.2 |
| | 0.50 | 5.86 | 0.91 | 60.1 | 13.4 | 13.2 | 3.2 | 46.9 | 11.4 |
| | 0.75 | 5.14 | 0.81 | 44.2 | 13.5 | 8.2 | 2.9 | 36.0 | 11.7 |
| | 1.00 | 4.57 | 0.61 | 35.8 | 10.9 | 6.0 | 2.7 | 29.8 | 9.6 |
| | 1.25 | 4.40 | 0.58 | 31.4 | 10.2 | 4.2 | 2.1 | 27.0 | 9.1 |
| | 1.50 | 4.55 | 0.70 | 27.0 | 9.6 | 3.1 | 1.7 | 23.9 | 8.7 |
| | 2.00-(B) | 5.11 | 0.57 | 21.0 | 9.0 | 1.5 | 1.1 | 19.3 | 8.3 |
| | 2.50 | 7.14 | 0.79 | 17.6 | 7.8 | 0.8 | 1.1 | 16.8 | 7.3 |
| | 3.00 | 6.31 | 1.79 | 13.5 | 7.5 | 0.6 | 1.1 | 12.9 | 6.9 |
| | 4.00 | 5.58 | 0.93 | 9.4 | 6.5 | 0.2 | 0.5 | 9.2 | 6.2 |
| | 5.00-(L) | 5.48 | 0.70 | 7.0 | 5.7 | 0.0 | 0.0 | 7.0 | 5.7 |
| | 6.00 | 6.53 | 1.04 | 4.0 | 4.8 | 0.0 | 0.0 | 4.0 | 4.8 |
| i.v. | 9.00 | 6.49 | 0.68 | 1.5 | 2.7 | 0.0 | 0.0 | 1.5 | 2.7 |
| | 10.00-(D) | — | — | — | — | — | — | — | — |
| | 24.00 | 6.24 | 0.77 | 0.0 | 0.0 | 0.0 | 0.0 | 0.0 | 0.0 |
| p.o. solution | 0.00 | 5.85 | 0.42 | 0.0 | 0.0 | 0.0 | 0.0 | 0.0 | 0.0 |
| | 0.25 | 6.13 | 0.52 | 16.6 | 8.1 | 7.8 | 4.1 | 8.8 | 6.8 |
| | 0.50 | 5.99 | 0.48 | 35.1 | 10.3 | 12.4 | 3.6 | 22.7 | 9.1 |
| | 0.75 | 5.83 | 0.48 | 40.2 | 11.4 | 10.0 | 3.3 | 30.2 | 10.3 |
| | 1.00 | 5.77 | 0.35 | 39.1 | 13.1 | 7.8 | 5.2 | 31.3 | 12.4 |
| | 1.50 | 5.40 | 0.30 | 30.8 | 11.9 | 3.4 | 2.5 | 27.3 | 11.0 |
| | 2.00-(B) | 5.11 | 0.48 | 24.0 | 10.7 | 2.2 | 1.8 | 21.8 | 10.1 |
| | 3.00 | 5.40 | 1.42 | 14.8 | 8.6 | 0.8 | 1.1 | 13.9 | 8.3 |
| | 4.00 | 4.86 | 0.59 | 8.7 | 7.5 | 0.2 | 0.6 | 8.4 | 7.3 |
| | 5.00-(L) | 5.12 | 0.54 | 5.6 | 5.6 | 0.0 | 0.0 | 5.6 | 5.6 |
| | 6.00 | 5.60 | 0.99 | 3.5 | 4.9 | 0.0 | 0.0 | 3.5 | 4.9 |
| | 9.00 | 5.68 | 0.69 | 1.8 | 2.7 | 0.0 | 0.0 | 1.8 | 2.7 |
| | 10.00-(D) | — | — | — | — | — | — | — | — |
| | 24.00 | 5.60 | 0.59 | 0.0 | 0.0 | 0.0 | 0.0 | 0.0 | 0.0 |
| p.o. capsule | 0.00 | 5.32 | 0.64 | 0.0 | 0.0 | 0.0 | 0.0 | 0.0 | 0.0 |
| | 0.25 | 6.08 | 0.60 | 1.9 | 4.4 | 0.7 | 1.6 | 1.2 | 2.6 |
| | 0.50 | 5.87 | 0.67 | 23.9 | 19.0 | 7.3 | 7.2 | 16.6 | 13.1 |
| | 0.75 | 5.85 | 0.64 | 34.0 | 19.8 | 9.7 | 5.6 | 24.4 | 16.1 |
| | 1.00 | 5.57 | 0.62 | 35.3 | 15.0 | 7.9 | 3.9 | 27.5 | 13.5 |
| | 1.50 | 5.24 | 0.44 | 31.4 | 9.0 | 4.3 | 2.3 | 27.2 | 9.1 |
| | 2.00-(B) | 5.04 | 0.57 | 29.5 | 8.0 | 3.1 | 2.6 | 26.2 | 7.3 |
| | 3.00 | 5.04 | 1.13 | 18.4 | 13.2 | 1.4 | 1.7 | 17.0 | 11.9 |
| | 4.00 | 4.43 | 0.65 | 10.4 | 8.5 | 0.3 | 0.7 | 10.1 | 8.2 |
| | 5.00-(L) | 4.71 | 0.54 | 7.0 | 6.2 | 0.2 | 0.4 | 6.8 | 6.0 |
| | 6.00 | 5.41 | 1.08 | 3.4 | 5.2 | 0.0 | 0.0 | 3.4 | 5.2 |
| | 9.00 | 5.42 | 0.79 | 1.4 | 2.6. | 0.0 | 0.0 | 1.4 | 2.6 |

TABLE 7-continued (Study 5)

| Administration | Time after administration [hours] | Glucose [mmol/l] | | Concentration (ng/ml) | | | | |
|---|---|---|---|---|---|---|---|---|
| | | | | (388) | | (623) | | (624)-calc. |
| | | mean | SD | mean | SD | mean | SD | mean | SD |
| | 10.00-(D) | — | — | — | — | — | — | — | — |
| | 24.00 | 5.44 | 0.62 | 0.0 | 0.0 | 0.0 | 0.0 | 0.0 | 0.0 |

— = not measured

The concentrations of active substance from study 5 (Table 7) make it possible to calculate pharmacokinetic parameters for 0.5 mg of AG-EE 623 ZW after oral administration (drinking solution; capsule) in the form of 1.0 mg of racemate AG-EE 388 ZW. Table 8 shows the pharmacokinetic parameters calculated without a model; it also shows, for comparison, the analogous parameters which can be calculated for AG-EE 623 ZW after oral administration (tablet) of 0.5 mg of AG-EE 623 ZW from the data of study 4 (Table 5).

TABLE 8

| Parameter AG-EE 623 ZW | Study 4 (Tablet) | Study 5 (Solution) | Study 5 (Capsule) |
|---|---|---|---|
| $c_{max}$ [ng/ml] | 15.0 ± 8.0 | 13.2 ± 3.4 | 11.4 ± 5.9 |
| $t_{max}$ [hours] | 0.6 ± 0.1 | 0.6 ± 0.2 | 0.9 ± 0.5 |
| $AUC_{0-\infty}$ [ng × h/ml] | 14.3 ± 8.6 | 16.7 ± 8.5 | 16.0 ± 8.1 |
| $t_{½} \lambda z$ [hours] | 0.5 ± 0.2 | 0.9 ± 0.4 | 0.8 ± 0.5 |
| $MRT_{tot.}$ [hours] | 0.9 ± 0.2 | 1.3 ± 0.3 | 1.5 ± 0.5 |

The parameters denoted:

$C_{max}$=maximum plasma concentration $t_{max}$=time of maximum plasma concentration $AUC_{0-\infty}$=area under the curve from 0 to infinity. The remaining area from the last data point to infinity was calculated by the log-linear regression line $lnC=a+\lambda z \times t$.

$t_{1/2}\lambda z$=terminal half-life, calculated using the log-linear regression line $lnC=a+\lambda z \times t$ of the last data points: $t_{1/2}\lambda z=ln2/\lambda z$.

$MRT_{tot.}$=total mean residence time

As can be seen, the parameters for AG-EE 623 ZW calculated from studies 4 and 5 correlate well. This means that the oral administration of AG-EE 623 ZW in the form of the racemate AG-EE 388 ZW, i.e. together with the same amount of AG-EE 624 ZW, has no pharmacokinetic advantages over the oral administration of pure AG-EE 623 ZW.

Moreover, the concentrations of active substance study 5 (Table 7) make it possible to calculate pharmacokinetic parameters of AG-EE 623 ZW and AG-EE 624 ZW after simultaneous administration in the form of the racemate AG-EE 388 ZW. The parameters calculated without a model are shown in Table 9.

TABLE 9

(Study 5)

| Administration | Parameter | (S)-enantiomer AG-EE 623 ZW | (R)-enantiomer AG-EE 624 ZW |
|---|---|---|---|
| i.v. | $c_{max}$ [ng/ml] | 36.3 ± 6.9 | 75.4 ± 12.6 |
| | $t_{max}$ [hours] | 0.25 ± 0.04 | 0.27 ± 0.03 |
| | $AUC_{0-\infty}$ [ng × h/ml] | 20.8 ± 7.1 | 134 ± 58 |
| | $t_{½} \lambda z$ [hours] | 0.9 ± 0.8 | 2.4 ± 1.1 |
| | $MRT_{intr.}$ [hours] | 0.9 ± 0.6 | 3.3 ± 1.7 |
| | CL [ml/min] | 443 ± 140 | 75 ± 34 |
| p.o. solution | $c_{max}$ [ng/ml] | 13.2 ± 3.4 | 32.3 ± 11.9 |
| | $t_{max}$ [hours] | 0.6 ± 0.2 | 1.0 ± 0.3 |
| | $AUC_{0-\infty}$ [ng × h/ml] | 16.7 ± 8.5 | 111 ± 62 |
| | $t_{½} \lambda z$ [hours] | 0.9 ± 0.4 | 2.3 ± 1.7 |
| | $MRT_{tot.}$ [hours] | 1.3 ± 0.3 | 3.4 ± 2.0 |
| | f [%] | 76 ± 20 | 83 ± 32 |

The parameters in Table 9 denote:

$C_{max}$=maximum plasma concentration $t_{max}$=time of maximum plasma concentration $AUC_{0-\infty}$=area under the curve from 0 to infinity $t_{1/2}\lambda z$=terminal half-life $MRT_{intr.}$=intrinsic mean residence time CL=clearance $MRT_{tot.}$=total mean residence time f=absolute (oral) bioavailability The amazing difference between the two enantiomers is the fact that the effective enantiomer, AG-EE 623 ZW, in spite of having a relatively long period of activity, is surprisingly eliminated more rapidly than the ineffective enantiomer, AG-EE 624 ZW, as is additionally demonstrated by FIGS. 1 and 2. After the administration of the racemate, the ineffective enantiomer, AG-EE 624 ZW, is therefore present not only as an unnecessary additive in plasma concentrations which are just as high as those of the effective enantiomer, AG-EE 623 ZW, but is present in unexpectedly higher maximum and long-lasting levels. The effect of this, as shown in Table 6, e.g. on administration of one tablet containing 2 mg of AG-EE 388 ZW or one tablet containing 1 mg of AG-EE 623 ZW, is that the maximum concentrations are 84±25 and 28±18 ng/ml, respectively, and the concentrations after 4 hours are 19±8 and 0.7±1.0 ng/ml, respectively, after 5 hours 13±6 and 0.3±0.7 ng/ml, respectively, and after 6 hours 10±6 and 0.3±0.7 ng/ml, respectively.

Thus, compared with the administration of AG-EE 388 ZW, the surprising advantage of the administration of AG-EE 623 ZW is that unnecessarily high and long-lasting levels of the substance in the body are avoided, which is of major importance in long-term therapy such as that of diabetes mellitus.

The studies described above show that the new (S)-enantiomer, namely (S)(+)-2-ethoxy-4-[N-[1-(2-piperidino-phenyl)-3-methyl-1-butyl]aminocarbonylmethyl]-benzoic acid, as a vehicle of blood sugar-lowering activity, is far superior to AG-EE 388 ZW, because of this surprisingly rapid elimination from the blood which was not foreseeable in view of its relatively long duration of activity, and these superior qualities go far beyond the "normal" advantage of an enantiomer over its racemate, namely the advantage of halving the dose.

The present invention therefore relates to the new (S)(+)-2-ethoxy-4-[N-[1-(2-piperidino-phenyl)-3-methyl-1-butyl]-aminocarbonylmethyl]-benzoic acid or an (S)(+)-2-ethoxy-4-[N-[1-(2-piperidino-phenyl)-3-methyl-1-butyl]-aminocarbonylmethyl]-benzoic acid, which is substantially optically pure, e.g. having an optical purity of at least ee=95%, preferably 98 to 100%, the physiologically acceptable salts thereof with inorganic or organic acids or bases, pharmaceutical compositions containing this compound or the physiologically acceptable salts thereof and processes for preparing them.

According to the invention, the new compound is obtained by the following methods:

a) reaction of the (S)-amine of formula

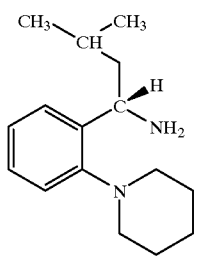

(I)

with a carboxylic acid of general formula

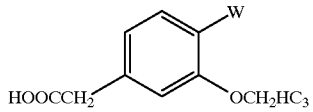

(II)

wherein
W represents a carboxy group or a carboxy group protected by a protecting group,
or with the reactive derivatives thereof optionally prepared in the reaction mixture and, if necessary, subsequent cleaving of a protecting group.

Reactive derivatives of a compound of general formula II may be, for example, the esters thereof such as the methyl, ethyl or benzyl ester, the thioesters thereof such as the methylthio or ethylthioesters, the halides thereof such as acid chloride, the anhydrides or imidazolides thereof.

The reaction is conveniently carried out in a solvent such as methylene chloride, chloroform, carbon tetrachloride, ether, tetrahydrofuran, dioxane, benzene, toluene, acetonitrile or dimethylformamide, optionally in the presence of an acid-activating agent or a dehydrating agent, e.g. in the presence of ethylchloroformate, isobutylchloroformate, thionylchloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, or an agent which activates the amino group, e.g. phosphorus trichloride, and optionally in the presence of an inorganic base such as sodium carbonate or a tertiary organic base such as triethylamine or pyridine which may simultaneously serve as solvent, at temperatures between −25 and 250° C., but preferably at temperatures between −10° C. and the boiling temperature of the solvent used. The reaction may also be carried out without a solvent and moreover any water formed during the reaction may be removed by azeotropic distillation, e.g. by heating with toluene using a water separator, or by the addition of a drying agent such as magnesium sulphate or molecular sieve.

If necessary, the subsequent cleaving of a protecting group is preferably carried out by hydrolysis, conveniently either in the presence of an acid such as hydrochloric, sulphuric, phosphoric, trifluoroacetic or trichloroacetic acid or in the presence of a base such as sodium hydroxide or potassium hydroxide in a suitable solvent such as water, methanol, methanol/water, ethanol, ethanol/water, water/isopropanol or water/dioxane at temperatures between −10 and 120° C., e.g. at temperatures between ambient temperature and the boiling temperature of the reaction mixture.

A tert.-butyl group used as protective group may also be cleaved thermally, optionally in an inert solvent such as methylene chloride, chloroform, benzene, toluene, tetrahydrofuran, dioxane or glacial acetic acid and preferably in the presence of a strong acid such as trifluoroacetic, hydrobromic, p-toluenesulphonic, sulphuric, phosphoric or polyphosphoric acid.

Moreover, a benzyl group used as protective group may also be cleaved hydrogenolytically in the presence of a hydrogenation catalyst such as palladium/charcoal in a suitable solvent such as methanol, ethanol, ethanol/water, glacial acetic acid, ethyl acetate, dioxane or di-methylformamide.

b) Cleaving an (S)-compound of general formula

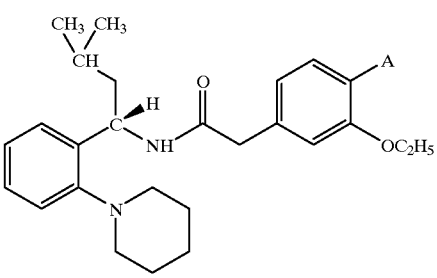

(III)

wherein
A represents a group which may be converted into a carboxy group by hydrolysis, thermolysis or hydrogenolysis.

Examples of hydrolysable groups include functional derivatives of the carboxy group such as the unsubstituted or substituted amides, esters, thioesters, orthoesters, iminoethers, amidines or anhydrides thereof, a nitrile group, a tetrazolyl group, an optionally substituted 1,3-oxazol-2-yl or 1,3-oxazolin-2-yl group and examples of thermolytically cleavable groups include the esters with tertiary alcohols, e.g. a tert.butylester, and examples of hydrogenolytically cleavable groups include the aralkyl groups, e.g. a benzyl group.

The hydrolysis is conveniently carried out either in the presence of an acid such as hydrochloric, sulphuric, phosphoric, trifluoroacetic or trichloroacetic acid or in the presence of a base such as sodium hydroxide or potassium hydroxide in a suitable solvent such as water, water/methanol, ethanol, water/ethanol, water/isopropanol or water/dioxane at temperatures between −10 and 120° C., e.g. at temperatures between ambient temperature and the boiling temperature of the reaction mixture.

If A in a compound of general formula III represents a nitrile or aminocarbonyl group, these groups may be converted into the carboxy group by means of 100% phosphoric acid at temperatures between 100 and 180° C., preferably at temperatures between 120 and 160° C., or using a nitrite, e.g. sodium nitrite, in the presence of an acid such as sulphuric acid, whilst the latter may conveniently be used as solvent at the same time, at temperatures between 0 and 50° C.

If A in a compound of general formula III represents a tert.butyloxycarbonyl group, for example, the tert.butyl group may also be cleaved thermally, optionally in an inert solvent such as methylene chloride, chloroform, benzene, toluene, tetrahydrofuran, dioxane or glacial acetic acid and preferably in the presence of a strong acid such as trifluoroacetic acid, hydrobromic acid, p-toluenesulphonic acid, sulphuric acid, phosphoric acid or polyphosphoric acid, at temperatures between 0 and 100° C., preferably at temperatures between 20° C. and the boiling temperature of the solvent used.

If A in a compound of general formula III represents a benzyloxycarbonyl group, for example, the benzyl group may also be cleaved hydrogenolytically in the presence of a hydrogenation catalyst such as palladium/charcoal in a suitable solvent such as methanol, ethanol, methanol/water, ethanol/water, glacial acetic acid, ethyl acetate, dioxane or dimethylformamide, preferably at temperatures between 0 and 50° C., e.g. at ambient temperature and under a hydrogen pressure of from 1 to 5 bar.

c) Reaction of an (S)-compound of general formula

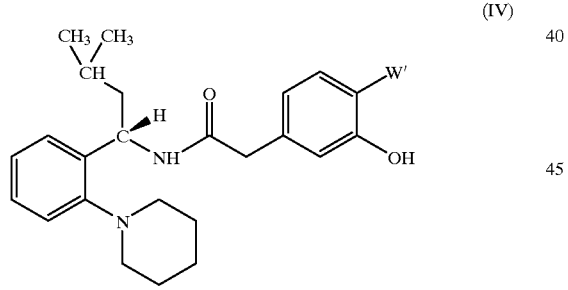

(IV)

wherein
W' represents a carboxy group or an alkoxycarbonyl group having a total of 2 to 5 carbon atoms, wherein the alkyl moiety of the alkoxy group may be substituted by a phenyl group,
with a compound of general formula

Z—CH₂—CH₃ (V)

wherein
Z represents a nucleophilically exchangeable group such as a halogen atom, a sulphonyloxy group or, together with the adjacent hydrogen atom, represents a diazo group, optionally followed by hydrolysis or hydrogenolysis.

The reaction is conveniently carried out with a corresponding halide, sulphonic acid ester or sulphuric acid diester, e.g. with ethyl bromide, ethyl iodide, diethylsulphate, ethyl p-toluenesulphonate or ethylmethanesulphonate, or with diazoethane, optionally in the presence of a base such as sodium hydride, potassium carbonate, sodium hydroxide, potassium tert.butoxide or triethylamine, preferably in a suitable solvent such as acetone, diethylether, tetrahydrofuran, dioxane, pyridine or dimethylformamide at temperatures between 0 and 100° C., preferably at temperatures between 20 and 50° C.

If W' in a compound of general formula IV represents a carboxy group, this can be converted into the corresponding ester compound.

If necessary, the subsequent hydrolysis is carried out either in the presence of an acid such as hydrochloric, sulphuric, phosphoric, trifluoroacetic or trichloroacetic acid or in the presence of a base such as sodium hydroxide or potassium hydroxide in a suitable solvent such as water, methanol, methanol/water, ethanol, ethanol/water, water/isopropanol or water/dioxane at temperatures between −10 and 120° C., e.g. at temperatures between ambient temperature and the boiling temperature of the reaction mixture, or the subsequent hydrogenolysis is carried out in the presence of a hydrogenation catalyst such as palladium/charcoal in a suitable solvent such as methanol, ethanol, ethanol/water, glacial acetic acid, ethyl acetate, dioxane or dimethylformamide under a hydrogen pressure of from 1 to 10 bar.

d) Enantioselective reduction of a compound of general formula

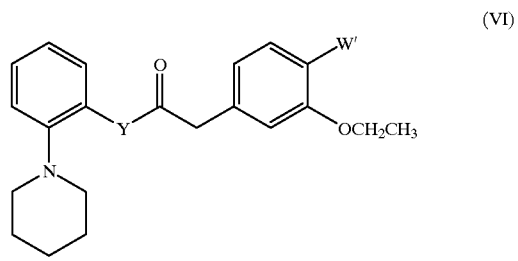

(VI)

wherein
W' represents a carboxy group or an alkoxycarbonyl group having a total of 2 to 5 carbon atoms, wherein the alkyl moiety of the alkoxy group may be substituted by a phenyl group, and
Y represents a group of the formula

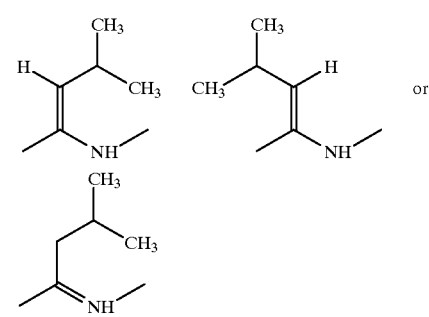

or and optional subsequent hydrolysis.

The reduction is preferably carried out with hydrogen in the presence of a suitable chiral hydrogenation catalyst in a suitable solvent such as methanol, ethanol, isopropanol, ethyl acetate, dioxane, tetrahydrofuran, methanol/ tetrahydrofuran, methanol/methylene chloride, ethanol/methylene chloride of isopropanol/methylene chloride at temperatures between 0 and 100° C., but preferably at temperatures between 20 and 50° C., under a hydrogen pressure of between 1 and 1000 bar, preferably between 5 and 100 bar, and conveniently with the addition of 0.1 to 5%, preferably 0.3 to 1%, of titanium(IV)tetraisopropoxide, preferably with the exclusion of oxygen from the air. The reduction is preferably carried out with the (Z)-form of a compound of general formula VI.

Examples of chiral hydrogenation catalysts are the corresponding metal ligand complexes such as Ru(OCO—CH$_3$)$_2$[(S)-BINAP], Ru$_2$Cl$_4$[(S)-BINAP]$_2$×N(C$_2$H$_5$)$_3$, Rh[(S)-BINAP-NBD]ClO$_4$ or Rh[(-)-NORPHOS-COD)BF$_4$.

During the catalytic hydrogenation, a benzyloxycarbonyl group may simultaneously be reduced and converted into the carboxy, group.

If necessary, the subsequent hydrolysis is carried out either in the presence of an acid such as hydrochloric, sulphuric, phosphoric, trifluoroacetic or trichloroacetic acid or in the presence of a base such as sodium hydroxide or potassium hydroxide in a suitable solvent such as water, methanol, methanol/water, ethanol, ethanol/water, water/isopropanol or water/dioxane at temperatures between −10 and 120° C., e.g. at temperatures between ambient temperature and the boiling temperature of the reaction mixture.

e) Oxidation of an (S)-compound of general formula

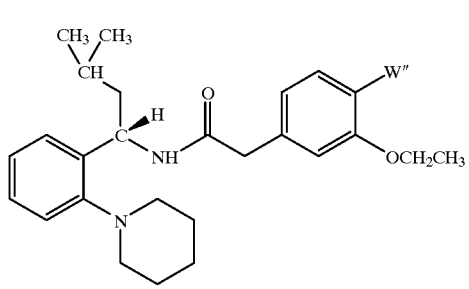

(VII)

wherein
W" represents a group which may be converted into a carboxy group by oxidation.

An example of an oxidisable group of this kind might be a formyl group and the acetals thereof, a hydroxymethyl group and the ethers thereof, an unsubstituted or substituted acyl group such as acetyl, chloroacetyl, propionyl, malonic acid-(1)-yl group or a malonic ester-(1)-yl group.

The reaction is carried out with an oxidising agent in a suitable solvent such as water, glacial acetic acid, methylene chloride, dioxane or glycoldimethylether at temperatures between 0 and 100° C., but expediently at temperatures between 20° C. and 50° C. However, the reaction is pre ferably carried out with silver oxide/sodium hydroxide solution, manganese dioxide/acetone or methylene chloride, hydrogen peroxide/sodium hydroxide solution, bromine or chlorine/sodium or potassium hydroxide solution, chromium trioxide/pyridine or pyridinium chlorochromate.

f) Separation of a mixture, consisting of any desired amount of the (S)-enantiomer of general formula

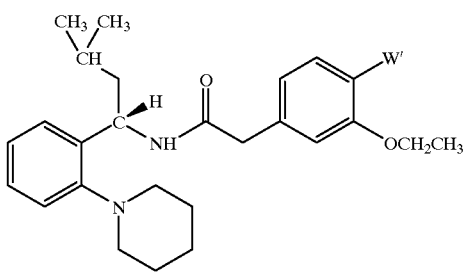

(VIII)

and any desired amount of the (R)-enantiomer of general formula

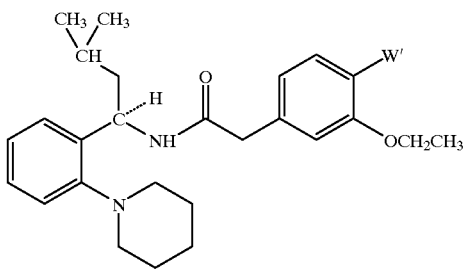

(IX)

wherein
W' represents a carboxy group or an alkoxycarbonyl group having a total of 2 to 5 carbon atoms, wherein the alkyl moiety of the alkoxy group may be substituted by a phenyl group,
preferably a 50/50 mixture, via the diastereomeric adducts, complexes or salts thereof, and followed if necessary by hydrolysis or hydrogenolysis.

The separation is preferably carried out using column or HPL chromatography by forming the diastereomeric adducts or complexes on a chiral phase.

If necessary, the subsequent hydrolysis is carried out either in the presence of an acid such as hydrochloric, sulphuric, phosphoric, trifluoroacetic or trichloroacetic acid or in the presence of a base such as sodium hydroxide or potassium hydroxide in a suitable solvent such as water, methanol, methanol/water, ethanol, ethanol/water, water/isopropanol or water/dioxane at temperatures between −10 and 120° C., e.g. at temperatures between ambient temperature and the boiling temperature of the reaction mixture, or
the subsequent hydrogenolysis is carried out in the presence of a hydrogenation catalyst such as palladium/charcoal in a suitable solvent such as methanol, ethanol, ethanol/water, glacial acetic acid, ethyl acetate, dioxane or dimethylformamide under a hydrogen pressure of from 1 to 10 bar.

The (S)-enantiomer thus obtained according to the invention, having an optical purity of, preferably, at least 90% can be converted by fractional crystallisation into an (S)-enantiomer having an optical purity of at least 95%, preferably 98 to 100%.

The same applies to the (S)-compounds according to the invention of formulae III, IV and VII, and more particularly the esters thereof.

The (S)-enantiomer thus obtained according to the invention can be converted into the salts thereof, more particularly, for pharmaceutical use, into the physiologically acceptable salts thereof with inorganic or organic acids or bases. Examples of such acids include hydrochloric acid, hydrobromic acid, sulphuric acid, phosphoric acid, lactic acid, citric acid, tartaric acid, succinic acid, maleic acid or fumaric acid and examples of bases include sodium hydroxide, potassium hydroxide, calcium hydroxide, cyclohexylamine, ethanolamine, diethanolamine, triethanolamine, ethylenediamine or lysine.

The compounds of formulae I to IX used as starting materials are known from the literature in some cases or may be obtained by methods known per se.

The (S)-amine of formula I can be obtained from the corresponding racemic amine by racemate cleaving, e.g. by means of fractional crystallisation of the diastereomeric salts with suitable optically active acids, preferably with N-acetyl-L-glutamic acid, and if necessary recrystallisation and subsequent decomposition of the salts, by column or HPL-chromatography on chiral phases, optionally in the form of an acyl derivative, or by forming diastereomeric compounds, then separating and subsequently cleaving them.

Moreover, the (S)-amine of formula I may be prepared by enantioselective reduction using hydrogen in the presence of a suitable chiral hydrogenation catalyst, starting from a corresponding N-acyl-ketimine or enamide, conveniently with the addition of 0.1 to 5% titanium tetraisopropoxide, optionally with subsequent cleaving of the acyl group such as the formyl or acetyl group, by diastereoselective reduction of a corresponding ketimine or hydrazine chirally substituted at the nitrogen atom, using hydrogen in the presence of a suitable hydrogenation catalyst, expediently with the addition of 0.1 to 5% titanium tetraisopropoxide, and optionally followed by cleaving of the chiral auxiliary group, e.g. the (S)-1-phenethyl group, by catalytic hydrogenolysis, or by diastereoselective addition of a corresponding organometallic compound, preferably a Grignard or lithium compound, to a corresponding aldimine chirally substituted at the nitrogen atom, optionally with the addition of 0.1 to 10% titanium tetraisopropoxide, subsequent hydrolysis and optional separation of the resulting diastereomers and subsequent cleaving of the chiral auxiliary group, e.g. the (R)-1-phenethyl group by catalytic hydrogenolysis, and if necessary the (S)-amine may be obtained in a higher enantiomeric purity by salt formation with suitable optically active acids, preferably with N-acetyl-L-glutamic acid, and if necessary single or multiple recrystallisation and subsequent decomposition of the salt.

The compounds of general formulae III, IV and VII used as starting materials are obtained by reacting the (S)-amine I with a corresponding carboxylic acid or a reactive derivative thereof and optionally subsequently splitting off any protecting group used.

The compound of general formula VI used as starting material is obtained by acylating the corresponding imino compound or the organometallic complexes thereof with the corresponding carboxylic acid or with the reactive derivatives thereof with optional subsequent cleaving of an ester group.

The new (S)-enantiomer is virtually non-toxic; for example, after a single administration of 1000 mg/kg p.o. (suspension in 1% methylcellulose) to 5 male and 5 female rats, no animals died within the observation period of 14 days.

In view of its pharmacological and pharmacokinetic properties, the (S)-enantiomer prepared according to the invention (AG-EE 623 ZW) and the physiologically acceptable salts thereof are suitable for the treatment of diabetes mellitus. For this purpose, AG-EE 623 ZW or the physiologically acceptable salts thereof, optionally combined with other active substances, may be incorporated in the conventional galenic preparations such as plain or coated tablets, capsules, powders, suppositories, suspensions or injectable solutions. The single dose for adults is 0.1 to 20 mg, preferably 0.25 to 5 mg, especially 0.25, 0.5, 1.0, 1.5, 2.0, 2.5, 3.0 or 5.0 mg, once, twice or three times a day.

The present invention further relates to the new (S)-amine of formula I which is a valuable intermediate product for preparing the new (S)-enantiomer, and the addition salts thereof with inorganic or organic acids.

The present invention also relates to the new compounds of general formulae III, IV and VII which are valuable intermediate products for preparing the new (S)-enantiomer, and the addition salts thereof with inorganic or organic acids.

The Examples which follow are intended to illustrate the invention:

EXAMPLE A (S)-1-(2-Piperidino-phenyl)-3-methyl-1-butylamine

A stirred solution of 122 g (0.495 mol) of racemic 1-(2-piperidino-phenyl)-3-methyl-1-butylamine in 1000 ml of acetone is mixed with 93.7 g (0.495 mol) of N-acetyl-L-glutaminic acid. The mixture is refluxed over a vapour bath and methanol is added in batches (a total of about 80 ml) until a clear solution is obtained. After this has been left to cool and stand overnight at ambient temperature, the crystals obtained are removed by suction filtering, washed twice with 200 ml of cold acetone at −15° C. and then dried. The product obtained [98.9 g; melting point: 163–166° C.; $[\alpha]_D^{20}$=+0.286° (c=1 in methanol)] is recrystallised from 1000 ml of acetone with the addition of 200 ml of methanol, thereby obtaining the (S)-1-(2-piperidino-phenyl)-3-methyl-1-butylamine as the addition salt of N-acetyl-L-glutaminic acid.

Yield: 65.1 g (60.4% of theory), Melting point: 168–171° C.; Calculated: C, 63.42; H, 8.56; N, 9.65; Found: 63.64; 8.86; 9.60. $[\alpha]_D^{20}$=+0.357° (c=1 in methanol)

The free amine is obtained as an oil by liberation, for example, with a sodium hydroxide or ammonia solution, extraction with toluene, ether, ethylacetate or methylene chloride, for example, and drying, filtering and evaporation of the extract in vacuo.

The (S)-configuration of the amine was demonstrated as follows:

Reaction of the amine with (S')-1-phenethylisocyanate in ether to obtain the corresponding urea derivative [melting point: 183–184° C.; $[\alpha]_D^{20}$=−2.25° (c=1 in methanol)], growing crystals from ethanol/water (8/1) and subsequent X-ray structural analysis showed the (S,S')-configuration for the urea derivative and consequently the (S)-configuration for the amine used.

Enantiomeric purity was determined as follows:

1. Acetylation of a sample of the amine with 1.3 equivalents of acetic anhydride in glacial acetic acid at 20° C. overnight.

2. Investigation of the N-acetyl derivative (melting point: 128–132° C.) by HPLC on a chiral phase HPLC column made by Baker, in which (S)-N-(3,5-dinitrobenzoyl)-2-phenyl-glycine is covalently bonded to aminopropyl silica gel (particle size 5 μm, spherical, pore size 60 A; column length: 250 mm with internal diameter 4.6 mm; eluant: n-hexane/isopropanol (100/5); flow rate: 2 ml/minute; temperature: 20° C.; UV-detection at 254 nm.) Found: peak 1(R): peak 2(S)=0.75%: 99.25%, ee (enantiomeric excess)=98.5% (S).

The (S)-amine may be converted into the dihydrochloride hydrate thereof using ethereal hydrogen chloride solution.

Melting point: 135–145° C. (decomposition); Calc. (×H$_2$O): C, 56.99; H, 8.97; N, 8.31 Cl 21.02; Found: 56.85; 8.93; 8.38; 21.25; $[\alpha]_D^{20}$=+26.1° (c=1 in methanol)

EXAMPLE B

N-Acetyl-N-[1-(2-piperidino-phenyl)-3-methyl-1-buten-1-yl]-amine

At ambient temperature, 4.7 ml (81.8 mMol) of glacial acetic acid, 25.7 g (98.2 mMol) of triphenylphosphine, 34.2 ml (245 mMol) of triethylamine and 7.9 ml (81.8 mMol) of carbon tetrachloride are added to a solution of 20 g (81.8 mmol) of freshly prepared isobutyl-(2-piperidino-phenyl)-ketimine in 200 ml of acetonitrile and the resulting mixture is stirred for 18 hours at ambient temperature. It is then evaporated down in vacuo and distributed between ethyl acetate and water. The organic extract is dried and filtered and evaporated down in vacuo. The evaporation residue is purified by column chromatography on silica gel (toluene/ethyl acetate=10/1), eluting first the (E)-form and then the (Z)-form.
(E)-form:
Yield: 6.1 g (26% of theory), Melting point: 135–137° C. (ethylacetate/petroleum ether); Calculated: C, 75.48; H, 9.15; N, 9.78; Found: 75.47; 9.35; 9.70.
(Z)-form:
Yield: 3.1 g (13% of theory), Melting point: 140–143° C. (ethylacetate); Calculated: C, 75.48; H, 9.15; N, 9.78; Found: 75.56; 9.30; 9.79.

EXAMPLE C

N-Acetyl-N-[1-(2-piperidino-phenyl)-3-methyl-1-buten-1-yl]-amine 17 ml (0.18 mol) of acetic anhydride are added dropwise, at an internal temperature of 0° C., to a stirred solution of 44 g (0.18 mol) of freshly prepared isobutyl-(2-piperidino-phenyl)-ketimine in 440 ml of toluene. The mixture is stirred for a further 3 hours at 0° C. and for 15 hours at ambient temperature, then evaporated down in vacuo, the evaporation residue is dissolved in ethyl acetate and extracted several times with aqueous sodium hydrogen carbonate solution. The organic phase is dried, filtered and evaporated down in vacuo. The evaporation residue is purified by column chromatography on silica gel (toluene/ethyl acetate=5/1), eluting first the (E)-form and then the (Z)-form.
(E)-form:
Yield: 3.0 g (5.8% of theory),
(Z)-form:
Yield: 17.8 g (34.5% of theory), Melting point: 139–141° C. (ethyl acetate); Calculated: C, 75.48; H, 9.15; N, 9.78; Found: 75.68; 8.99; 9.86.

EXAMPLE D

N-Acetyl-N-[(S)-1-(2-piperidino-phenyl)-3-methyl-1-butyl]-amine 0.57 g (1.99 mMol) of (Z)-N-acetyl-N-[1-(2-piperidino-phenyl)-3-methyl-1-buten-1-yl]-amine, melting point 139–141° C., are dissolved in 10 ml of degassed solvent mixture (methanol/methylene chloride=5/1) under an Argon atmosphere and added to a solution of 16.8 mg (1 mol %) of the NOYORI-catalyst Ru(O-acetyl)$_2$[(S)-BINAP] (prepared from [Ru(COD)Cl$_2$]$_n$ with (S)-BINAP [=(S)-2,2'-bis (diphenylphosphino)-1,1'-binaphthyl], triethylamine and sodium acetate), and 3.4 mg (0.5 mol %) of titanium tetraisopropoxide in 10 ml of degassed solvent mixture tmethanol/methylene chloride=5/1). The reaction mixture is drawn into an autoclave which is evacuated at 10$^{-2}$ mbar. It s rinsed several times with hydrogen at 4 bar and the mixture is then hydrogenated at 30° C. under 100 bar until the hydrogen uptake has ceased (170 hours). Then the reddish-brown solution is evaporated down in vacuo, the evaporation residue is refluxed with 30 ml of n-hexane and filtered hot to remove any insoluble matter. When the filtrate cools, crystallisation occurs.

Yield: 0.31 g (54% of theory), Melting point: 127–131° C.; enantiomeric, purity: ee=82% (S) [HPLC method: see Example A].

14% of the racemic N-acetyl-amine of melting point 154–156° C. can be obtained from the insoluble matter obtained when boiling with 30 ml of n-hexane, by further decoction with n-hexane, filtration and crystallisation from the hexane solution.

EXAMPLE E (S)-1-(2-Piperidino-phenyl)-3-methyl-1-butylamine 1 g (3.47 mMol) of N-acetyl-N-[(S)-1-(2-piperidino-phenyl)-3-methyl-1-butyl]-amine (melting point: 128–133° C.; ee=99.4%] are refluxed in 10 ml of concentrated hydrochloric acid for 5.5 hours, then cooled and poured into a mixture of concentrated ammonia and ice. The mixture is extracted twice with ethyl acetate, the organic phase is washed with water, dried and filtered and then evaporated down in vacuo.

Yield: 0.84 g (98.8% of theory) oily amine.

By re-acetylation with 0.42 ml (1.3 equivalents) of acetic anhydride in 8.4 ml of glacial acetic acid overnight at ambient temperature, evaporation in vacuo, distribution of the evaporation residue between ethyl acetate and saturated aqueous sodium bicarbonate solution then drying, filtering and evaporation of the organic extract in vacuo, 0.83 g (84.7% of theory) of N-acetyl-N-[(S)-1-(2-piperidino-phenyl)-3-methyl-1-butyl]-amine are obtained (melting point: 130–132° C.; ee=99.4%).

EXAMPLE F

Ethyl 2-ethoxy-4-[N-(1-(2-piperidino-phenyl)-3-methyl-1-buten-1-yl)-aminocarbonylmethyl]-benzoate Prepared from isobutyl-(2-piperidino-phenyl)-ketimine and 3-ethoxy-4-ethoxycarbonyl-phenylacetic acid analogously to Example B. Purification by column chromatography on silica gel (toluene/acetone=10/1), eluting first the (E)-form and then the (Z)-form.
(E)-form:
Yield: 4% of theory, Melting point: 101–103° C.; Calculated: C, 72.77; H, 8.00; N, 5.85; Found: 72.74; 7.78; 5.86.
(Z)-form:
Yield: 28.1% of theory, Melting point: 124–127° C. (petroleum ether/toluene=5/1); Calculated: C, 72.77; H, 8.00; N, 5.85; Found: 72.90; 7.86: 5.83.

EXAMPLE G

N-[(S')-1-phenethyl]-N-[(S)-1-(2-piperidino-phenyl)-3-methyl-1-butyl]-amine 17 g (49 mMol) of N-[(S')-1-phenethyl]-isobutyl-(2-piperidino-phenyl)-ketimine, boiling point 150–155° C./0.3 torr [prepared from isobutyl-(2-piperidino-phenyl)-ketone and (S')-1-phenethyl-amine (made by Fluka, ee=99.6%) in toluene+triethylamine by dropwise addition of a solution of titanium tetrachloride in toluene] are dissolved in 170 ml of anhydrous ethanol. 1.7 g of titanium tetraisopropoxide and 8 g of Raney nickel are added and the mixture is hydrogenated at 50° C. under 200 bar of hydrogen. After 20 hours a further 8 g of Raney nickel are added and the mixture is hydrogenated for a further 52 hours under the same conditions. The catalyst is filtered off over a layer of Celite on a G3-mess and the filtrate is evaporated down in vacuo.

Yield: 13.1 g (76.6% of theory), Boiling point: 152° C./0.2 torr; Calculated: C, 82.23; H, 9.78; N, 7.99; Found: 82.00; 10.03; 7.74; $[\alpha]_D^{20}$=−55.3° (c=1.1 in methanol)

The diastereomeric purity is determined by HPLC on a Lichrosorb RP18 HPLC column made by E. Merck (Germany); column length: 250 mm with an internal diameter of 4 mm; particle size: 7 μm. Eluant: methanol/dioxane/ 0.1% aqueous sodium acetate solution, adjusted to pH 4.05 with acetic acid (135/60/5); temperature: 23° C.; UV-detection at 254 nm.

Found: peak 1(S,S'): peak 2(R,S')=98.4%: 1.4%, de (diastereomeric excess)=97.0% (S,S').

EXAMPLE H (S)-1-(2-Piperidino-phenyl)-3-methyl-1-butylamine 12.5 g (36 mMol) of N-[(S')-1-phenethyl]-N-[(S)-1-(2-piperidino-phenyl)-3-methyl-1-butyl]-amine with a de of 97.0% (S,S') are dissolved in 125 ml of water and 3.6 ml of conc. hydrochloric acid. 1.3 g of (10%) palladium/charcoal are added and the mixture is hydrogenated at 50° C. under 5 bar of hydrogen. After the hydrogen uptake has ended (10 hours) the mixture is filtered over a layer of Celite to remove the catalyst.

The filtrate is made alkaline with conc. ammonia with the addition of ice and extracted with ethyl acetate. The organic extract is dried and filtered and evaporated down in vacuo.

Yield: 6.4 g (72.1% of theory), Boiling point: 115–117° C./0.4 torr; Enantiomeric purity: ee=93.5% (S) [HPLC method (after previous acetylation): see Example A].

EXAMPLE I

N-[(R')-1-phenethyl]-N-[(S)-1-(2-piperidino-phenyl)-3-methyl-1-butyl]-amine

A solution of 2 g (6.84 mMol) of N-[(R')-1-phenethyl]-(2-piperidino-benzaldimine)[prepared from equimolar amounts of 2-piperidino-benzaldehyde and (R')-1-phenethylamine by standing overnight at ambient temperature and subsequent drying with sodium sulphate in ether solution] in 20 ml of anhydrous tetrahydrofuran is added dropwise to a solution of 27.4 mmol (4 equivalents) of isobutyl-magnesium bromide in 22 ml of anhydrous tetrahydrofuran, which is stirred in a bath at 60° C. After 18 hours the bath temperature is increased to 80° C. and a further 2 equivalents of isobutyl-magnesium bromide in 11 ml of tetrahydrofuran are added. After 12 hours stirring at 80° C. 2 equivalents of isobutyl-magnesium bromide solution are added once again. After about 90 hours at 80° C. the mixture is cooled, excess conc. hydrochloric acid is added and the resulting mixture is evaporated to dryness in a water jet vacuum. The evaporation residue is dissolved in water and made alkaline with conc. ammonia. It is extracted with ether, the organic extract is dried over sodium sulphate, filtered and evaporated in vacuo. The evaporation residue is purified by column chromatography on silica gel (toluene/ acetone=95/5).

Yield: 0.20 g (8.3% of theory), Melting point: <20° C.; The diastereomeric purity is determined by HPLC as in Example G. Found: peak 1(R,R'): peak 2(S,R')= 4.4%:95.6%, de (diastereomeric excess)=91.2% (S,R').

In an analogous mixture with 2.0 g of the Schiff's base and a total of 6 equivalents of isobutyl-magnesium bromide in toluene/tetrahydrofuran (4/1) and with the addition of 5% titanium(IV)-tetraisopropoxide and heating for 60 hours at 100° C. in a glass tank, a yield of 5% was achieved with a de of 97.6% (S,R').

EXAMPLE K (S)-1-(2-Piperidino-phenyl)-3-methyl-1-butylamine

A solution of 0.15 g (0.428 mMol) of N-[(R')-1-phenethyl]-N-[(S)-1-(2-piperidino-phenyl)-3-methyl-1-butyl]-amide (de=91.2%), 0.47 ml (0.47 mMol) of 1N-hydrochloric acid and 1.5 ml of water is hydrogenated in the presence of 20 mg of 10% palladium/charcoal for 5 hours at 50° C. under 3.4 bar of hydrogen. The mixture is filtered over kieselguhr, made alkaline with conc. ammonia and extracted with ethyl acetate. The extract is dried, filtered and evaporated in vacuo.

Yield: 0.066 g (62.8% of theory), Melting point: <20° C.; Enantiomeric purity: ee=87.6% (S) [HPLC method (after previous acetylation): see Example A].

EXAMPLE L

Ethyl (S)-2-ethoxy-4-[N-(1-(2-piperidino-phenyl)-3-methyl-1-butyl)-aminocarbonylmethyl]-benzoate 0.48 g (1.91 mMol) of 3-ethoxy-4-ethoxycarbonyl-phenylacetic acid, 0.60 g (2.29 mMol) of triphenylphosphine, 0.80 ml (5.73 mMol) of triethylamine and 0.18 ml (1.91 mMol) of carbon tetrachloride are added successively to a solution of 0.47 g (1.91 mMol) of (S)-3-methyl-1-(2-piperidino-phenyl)-1-butylamine (ee=98.5%) in 5 ml of anhydrous acetonitrile and the resulting mixture is stirred for 20 hours at ambient temperature. It is then evaporated down in vacuo and distributed between ethyl acetate and water. The organic extract is dried and filtered and evaporated down in vacuo. The evaporation residue is purified by column chromatography on silica gel (toluene/ ethyl acetate=10/1).

Yield: 0.71 g (77.3% of theory), Melting point: 110–112° C.; Calculated: C, 72.47; H, 8.39; N, 5.83; Found: 72.29; 8.42; 5.80.

The enantiomeric Purity is determined by HPLC on a chiral phase HPLC column made by Baker, in which (S)-N-3,5-dinitrobenzoyl-leucine is covalently bound to amino-propyl silica gel (particle size: 5 μm, spherical, 60 A pore size; column length: 250 mm with an internal diameter of 4.6 mm; eluant: n-hexane/tetrahydrofuran/methylene chloride/ethanol (90/10/1/1); flow rate: 2 ml per minute; temperature: 20° C.; UV detection at 242 nm).

Found: peak 1(R): peak 2(S)=0.75%: 99.25%, ee=98.5% (S).

EXAMPLE M

Ethyl (S)-2-ethoxy-4-[N-(1-(2-piperidino-phenyl)-3-methyl-1-butyl)-aminocarbonylmethyl]-benzoate 2.77 g (11 mMol) of 3-ethoxy-4-ethoxycarbonyl-phenylacetic acid are added at ambient temperature to a solution of 2.71 g (11 mMol) of anhydrous (S)-3-methyl-1-

(2-piperidino-phenyl)-1-butylamine (ee=98.5%) in 30 ml of absolute toluene and the mixture is stirred until dissolved. Then 2.38 g (11.55 mMol) of N,N'-dicyclohexyl-carbodiimide are added and the mixture is stirred at ambient temperature. After 24 hours a further 0.54 g (2.14 mMol) of 3-ethoxy-4-ethoxycarbonyl-phenylacetic acid and 0.48 g (2.33 mMol) of N,N'-dicyclohexylcarbodiimide are added and the mixture is stirred overnight. It is then cooled to an internal temperature of +5° C. and suction filtered to separate the precipitate, which is washed once with 5 ml of toluene. The combined toluene filtrates are evaporated down in vacuo to a volume of about 10 ml. The resulting solution is heated over the steam bath and petroleum ether is added in batches thereto (total of 55 ml) until the turbidity remains. It is cooled in ice, whereupon crystallisation takes place. It is suction filtered and dried at 75° C./4 torr. The product obtained (4.57 g; melting point 111–112° C.; ee=98.9%) is suspended in 50 ml of petroleum ether. The mixture is heated over the steam bath and sufficient toluene is added in batches (8 ml in total) until a solution is obtained. This is then cooled in ice and suction filtered to separate the crystals, which are dried at 75° C./4 torr.

Yield: 3.93 g (74.3% of theory), Melting point: 117–118° C.; Calculated: C, 72.47; H, 8.39; N, 5.83; Found: 72.44; 8.43; 5.93; $[\alpha]_D^{20}$=+9.4° (c=1.01 in methanol); Enantiomeric purity: ee=99.9% [HPLC method: see Example L]

EXAMPLE N (S)-2-Ethoxy-4-[N-(1-(2-piperidino-phenyl)-3-methyl-1-butyl)-aminocarbonylmethyl]-benzoic acid A solution of 3.79 g (7.88 mMol) of ethyl (S)-2-ethoxy-4-[N-(1-(2-piperidino-phenyl)-3-methyl-1-butyl)-aminocarbonylmethyl]-benzoate (ee=99.9%) in 37 ml of ethanol is stirred in a bath at 60° C. and 10 ml (10 mmol) of 1N sodium hydroxide solution are added. After 4 hours stirring at 60° C., 10 ml (10 mMol) of 1N-hydrochloric acid are added in the warm and the mixture is left to cool to ambient temperature. After inoculation and standing overnight, the mixture is cooled for a further hour in ice, with stirring. The crystals are separated by suction filtering and washed twice with 5 ml of water. They are then dried at 75° C. up to a final temperature of 100° C./4 torr in a vacuum drying cupboard over phosphorus pentoxide.

Yield: 3.13 g (87.7% of theory), Melting point: 130–131° C. (high-melting form); Calculated: C, 71.64; H, 8.02; N, 6.19; Found: 71.48; 7.87; 6.39; $[\alpha]_D^{20}$=+7.45° (c=1.06 in methanol)

The enantiomeric purity is determined by HPLC on a chiral phase HPLC column made by ChromTech (Sweden) with an AGP(α1-acid glycoprotein) phase; internal diameter: 4.0 mm; length: 100 mm; particle diameter: 5 μm. Temperature: 20° C.; eluant: 0.1% aqueous $KH_2PO_4$ solution (=A)+20% acetonitrile (=B), gradient increase within 4 minutes to 40% (B); flow rate: 1 ml per minute; UV detection at 240 nm. Retention time (S)-enantiomer: 2.7 minutes; retention time (R)-enantiomer: 4.1 minutes.

Found: (S):(R)=99.85%: 0.15%, ee=99.7% (S).

When a sample is recrystallised from ethanol/water (2/1) the melting point does not change. When a sample is heated in petroleum ether/toluene (5/3) the undissolved portion is filtered (melting point: 130–131° C.) and the filtrate is rapidly cooled, the low melting form of the title compound is obtained, melting point 99–101° C.

Calculated: C, 71.64; H, 8.02; N, 6.19; Found: 71.66; 7.97; 6.44.

The low melting form and the high melting form differ in their infra-red KBr spectra but not in their infra-red solution spectra (methylene chloride).

If a sample of the low melting form is heated beyond its melting point a second melting point is observed at 127–130° C.

If a sample of the low-melting form is recrystallised from ethanol/water (2/1), the high melting form is obtained.

The high melting form and the low melting form were investigated by Differential Scanning Calorimetry (DSC) [Mettler apparatus, TA-300 system; measuring cell: DSC 20; made by Mettler, CH-8306 Greifensee, Switzerland] with the following results:

| Compound of Example N | Heating rate 10° K/min. | Heating rate 3° K/min. |
|---|---|---|
| High melting form | Uniform melting peak with melting temperature of 133° C.; melting enthalpy: 100 J/g | Uniform melting peak with melting temperature of 132° C.; melting enthalpy: 99.1 J/g |
| Low melting form | 1st peak at 57° C. (very weak) 2nd peak at 78° C. (weak) 3rd endothermic peak at 107° C.; melting enthalpy: 55 J/g 4th endothermic peak at 132° C. melting enthalpy: 25 J/g | 1st peak at 54° C. (very weak; endothermic) 2nd endothermic peak at 104° C. melting temperature 102° C., melting enthalpy 52 J/g 3rd exothermic path of the base line by crystallisation of the substance melting at 104° C. 4th endothermic peak at 131° C., melting temperature 130° C. melting enthalpy 52 J/g |

EXAMPLE O

Ethyl (S)-2-ethoxy-4-[N-(1-(2-piperidino-phenyl)-3-methyl-1-butyl)-aminocarbonylmethyl]-benzoate 0.79 g (1.65 mMol) of ethyl (Z)-2-ethoxy-4-[N-(1-(2-piperidino-phenyl)-3-methyl-1-buten-1-yl)-aminocarbonylmethyl]-benzoate, melting point 124–127° C., are dissolved in 10 ml of degassed solvent mixture (methanol/methylene chloride=5/1) under an Argon atmosphere and added to a solution of 17 mg of the NOYORI-catalyst Ru(O-acetyl)₂[(S)-BINAP] (prepared from [Ru (COD)Cl₂]ₙ with (S)-BINAP [=(S)-2,2'-bis-(diphenylphosphino)-1,1'-binaphthyl], triethylamine and sodium acetate) and 3 mg of titanium tetraisopropoxide in 10 ml of degassed solvent mixture (methanol/methylene chloride=5/1). The reaction mixture is drawn into an autoclave evacuated at $10^{-2}$ mbar. This is flushed five times with hydrogen at 5 bar and finally hydrogenated at 30° C. and 100 bar until the hydrogen uptake has ceased (154 hours). The reddish-brown solution is evaporated down in vacuo, the evaporation residue is dissolved in 80 ml of other, filtered off from the undissolved brown flakes by means of activated charcoal and the resulting clear, bright yellow filtrate is evaporated down in vacuo. The evaporation residue (0.60 g) is refluxed in 60 ml of n-hexane and filtered hot to separate it from the insoluble matter. The filtrate is left to stand overnight at ambient temperature. The crystals which are precipitated are filtered off.

Yield: 0.45 g (56.7% of theory), Melting point: 131–133° C. (after sintering from 120° C.); Enantiomeric purity: ee=39% (S) [HPLC method: see Example L].

EXAMPLE P

Ethyl (S)-2-ethoxy-4-[N-(1-(2-piperidino-phenyl)-3-methyl-1-butyl)-aminocarbonylmethyl]-benzoate 0.05 g (1.15 mMol) of 55% sodium hydride in oil are added to a solution of 0.68 g (1.15 mMol) of ethyl (S)-2-hydroxy-4-[N-(1-(2-piperidino-phenyl)-3-methyl-1-butyl)-aminocarbonylmethyl]-benzoate [melting point: 125–126° C.; $[\alpha]_D^{20}$=+12.87° (c=1.01 in methanol)] in 5 ml of anhydrous dimethylformamide and the mixture is stirred for 0.5 hours at ambient temperature. Then a solution of 0.12 ml (1.15 mMol) of ethyliodide in 2.5 ml of anhydrous dimethylformamide is added dropwise thereto and the mixture is stirred for 5 hours at ambient temperature. It is evaporated down in vacuo, the residue is distributed between dilute sodium hydroxide solution and chloroform, the organic extract is dried, filtered and evaporated down in vacuo. The evaporation residue is purified by column chromatography on silica gel (toluene/ethyl acetate=10/1).

Yield: 0.48 g (67% of theory), Melting point: 110–112° C. Calculated: C, 72.47; H, 8.39; N, 5.83; Found: 72.61; 8.54; 5.97; Enantiomeric purity: ee=98.5% (S) [HPLC method: see Example L].

EXAMPLE Q

Ethyl (S)-2-ethoxy-4-[N-(1-(2-piperidino-phenyl)-3-methyl-1-butyl)-aminocarbonylmethyl]-benzoate Prepared from (S)-2-hydroxy-4-[N-(1-(2-piperidino-phenyl)-3-methyl-1-butyl)-aminocarbonylmethyl]-benzoic acid analogously to Example 5 using 2 equivalents of sodium hydride and 2 equivalents of ethyl iodide.

Yield: 42% of theory, Melting point: 110–112° C.; Calculated: C, 72.47; H, 8.39; N, 5.83; Found: 72.61; 8.54; 5.99; Enantiomeric purity: ee=98.3% (S) [HPLC method: see Example L].

EXAMPLE R

Ethyl (S)(+)-2-ethoxy-4-[N-(1-(2-piperidino-phenyl)-3-methyl-1-butyl)-aminocarbonylmethyl]-benzoate and Ethyl (R)(-)-2-ethoxy-4-[N-(1-(2-piperidino-phenyl)-3-methyl-1-butyl)-aminocarbonylmethyl]-benzoate 920 mg of ethyl (±)-2-ethoxy-4-[N-(1-(2-piperidino-phenyl)-3-methyl-1-butyl)-aminocarbonylmethyl]-benzoate are separated, in single doses of 10 mg, on a preparative chiral phase HPLC column made by Baker, in which (S)-N-3,5-dinitrobenzoyl-leucine is covalently bonded to aminopropyl-silica gel (particle size: 40 μm; column length: 250 mm with an internal diameter of 20 mm; eluant: n-hexane/tetrahydrofuran/ethanol/methylene chloride (180/20/3/2); flow rate: 21.25 ml per minute; temperature: 27° C.; UV-detection at 285 nm), in which first the (R)(-)-enantiomer (peak 1) and then the (S)(+)-enantiomer (peak 2) is eluted. After evaporation in vacuo, the following are obtained from the correspondingly cut and collected fractions:

Peak 1 fraction (R): 423 mg (crude),
Peak 2 fraction (S): 325 mg (crude).

In order to remove any impurities (including the stabiliser 2,6-di-tert.butyl-4-methyl-phenol contained in the tetrahydrofuran) the two fractions are each purified by column chromatography on silica gel (toluene/acetone=10/1).

(R)(-)-enantiomer:
Yield: 234.5 mg (51% of theory), Melting point: 122–124° C. (petroleum ether+acetone); Calculated: C, 72.47; H, 8.39; N, 5.83; Found: 72.40; 8.18; 5.71; $[\alpha]_D^{20}$=-8.3° (c=1 in methanol)

(S)-enantiomer:
Yield: 131.2 mg (28.5% of theory), Melting point: 122–124° C. (petroleum ether/acetone=8/1); Calculated: C, 72.47; H, 8.39; N, 5.83; Found: 72.28; 8.44; 5.70; $[\alpha]_D^{20}$=+8.3° (c=1 in methanol)

A chiral cell OD column made by Daicel is also suitable for separating the enantiomers. The (R)-enantiomer is eluted after 6.8 minutes and the (S)-enantiomer after 8.5 minutes on a column 250 mm long with an internal diameter of 4.6 mm (eluant: absolute ethanol/(n-hexane+0.2% diethylamine)=5/95; temperature: 40° C.; UV-detection at 245 nm).

EXAMPLE S (R)(-)-2-Ethoxy-4-[N-(1-(2-piperidino-phenyl)-3-methyl-1-butyl)-aminocarbonylmethyl]-benzoic acid×0.4 $H_2O$ Prepared from 150 mg (0.312 mMol) of ethyl (R)(-)-2-ethoxy-4-[N-(1-(2-piperidino-phenyl)-3-methyl-1-butyl)-aminocarbonyl-methyl)-benzoate [melting point: 122–124° C.; $[\alpha]_D^{20}$=-8.3° (c=1 in methanol)] by saponification with 1N sodium hydroxide solution in ethanol analogously to Example 3.

Yield: 95.8 mg (66.7% of theory), Melting point: 103–105° C. (toluene/petroleum ether); Calc. (×0.4 $H_2O$): C, 70.51; H, 8.01; N, 6.09; Found: 70.88; 7.79; 5.81; Molecular peak M$^+$: Calculated: 452; Found: 452; $[\alpha]_D^{20}$=-6.5° (c=1 in methanol); Enantiomeric purity: ee=99.7% (R)[HPLC method: see Example N].

EXAMPLE T (S)(+)-2-Ethoxy-4-[N-(1-(2-piperidino-phenyl)-3-methyl-1-butyl)-aminocarbonylmethyl)-benzoic acid×0.4 $H_2O$ Prepared from 89 mg (0.198 mMol) of ethyl (S)(+)-2-ethoxy-4-[N-(1-(2-piperidino-phenyl)-3-methyl-1-butyl)-aminocarbonylmethyl]-benzoate [melting point: 122–124° C.; $[\alpha]_D^{20}$=+8.3° (c=1 in methanol)] by saponification with 1N sodium hydroxide solution in ethanol analogously to Example N].

Yield: 44.5 mg (48.8% of theory), Melting point: 102–103° C. (toluene/petroleum ether); Calc.: (×0.4 $H_2O$) C, 70.51; H, 8.01; Found: 70.80 8.06; $[\alpha]_D^{20}$=+6.7° (c=1 in methanol); Enantiomeric purity: ee=99.6% (S)[HPLC method: see Example N].

EXAMPLE U (S)-2-Ethoxy-4-[N-(1-(2-piperidino-phenyl)-3-methyl-1-butyl)-aminocarbonylmethyl]-benzoic acid 0.26 g (0.47 mMol) of benzyl (S)-2-ethoxy-4-[N-(1-(2-pipieridino-phenyl)-3-methyl-1-butyl)-aminocarbonyl-methyl]-benzoate (melting point: 91–92° C.; $[\alpha]_D^{20}$=+9.5°; c=1.05 in methanol) are hydrogenated in 10 ml of ethanol using 0.12 g of (10%) palladium/charcoal at 50° C. and 5 bar of hydrogen. After 5 hours the catalyst is filtered off over kieselguhr and evaporated down in vacuo. The evaporation residue is crystallised from ethanol/water (2/1).

Yield: 0.15 g (70% of theory), Melting point: 130–131° C.; Calculated: C, 71.64; H, 8.02; N, 6.19; Found: 71.76; 8.12; 6.05; Enantiomeric purity: ee=99.6% [HPLC method: see Example N].

EXAMPLE V (S)-2-Ethoxy-4-[N-(1-(2-piperidino-phenyl)-3-methyl-1-butyl)-aminocarbonylmethyl]-benzoic acid 102 mg (0.20 mMol) of tert.butyl (S)-2-ethoxy-4-[N-(1-(2-piperidino-phenyl)-3-methyl-1-butyl)-aminocarbonyl-methyl]-benzoate (melting point: 122–123° C.; $[\alpha]_D^{20}$=+8.7°; c=1 in methanol) are refluxed in 5 ml of benzene together with a few crystals of p-toluenesulphonic acid hydrate, for half a day. The desired product is then obtained, according to thin layer chromatography, according to the $R_f$ value and mass spectrum.

Melting point: 129–131° C.; Molecular peak $M^+$: Calc.: 452; Found: 452

EXAMPLE W (S)-2-Ethoxy-4-[N-(1-(2-piperidino-phenyl)-3-methyl-1-butyl)-aminocarbonylmethyl]-benzoic acid 200 mg (0.395 mMol) of tert.butyl (S)-2-ethoxy-4-[N-(1-(2-piperidino-phenyl)-3-methyl-1-butyl)-aminocarbonyl-methyl]-benzoate (melting point: 122–123° C.; $[\alpha]_D^{20}$=+8.7°; c=1 in methanol) are stirred into 2 ml of methylene chloride together with 0.45 g (3.95 mMol) of trifluoroacetic acid overnight at ambient temperature. The mixture is evaporated down in vacuo and the evaporation residue is distributed between aqueous sodium hydrogen carbonate solution and ethyl acetate. The organic extract is dried, filtered and evaporated down in vacuo. The evaporation residue is crystallised from ethanol/water (2/1).

Yield: 115 mg (64.7% of theory), Melting point: 126–128° C.; Calculated: C, 71.64; H, 8.02; N, 6.19; Found: 71.39; 7.91; 6.06; $[\alpha]_D^{20}$=+6.97° (c=0.975 in methanol) Enantiomeric purity: ee=99.8% [HPLC method: see Example N].

EXAMPLE X

Tablets containing 0.25 mg AG-EE 623 ZW

One tablet contains:

0.250 mg of active substance 0.125 mg of N-methylglucamine 0.038 mg of polyvinylpyrrolidone 0.075 mg of polyoxyethylenepolyoxypropylene polymer 0.150 mg of microcrystalline cellulose Preparation:

The active substance and excipients are dissolved in water at 90° C. or the microcrystalline cellulose is suspended and the dispersion is evaporated down in vacuo. The dry mass is screened to a mesh size of 1 mm.

The following ingredients are added to the granulated active substance, for each tablet:

24.862 mg of sodium carboxymethyl starch
24.000 mg of microcrystalline cellulose
0.500 mg of magnesium stearate 50.000 mg Round, biplanar tablets weighing 50 msog and measuring 5 mm in diameter are compressed from this mixture.

EXAMPLE Y

Tablets containing 0.5 mg of AG-EE 623 ZW

One tablet contains:

0.500 mg of active substance 0.250 mg of N-methylglucamine 0.075 mg of polyvinylpyrrolidone 0.150 mg of polyoxyethylenepolyoxypropylene polymer 0.300 mg of microcrystalline cellulose Preparation:

The active substance and excipients are dissolved in water at 90° C. and the microcrystalline cellulose is suspended therein and the dispersion is evaporated down in vacuo. The dry mass is screened to a mesh size of 1 mm.

The following ingredients are added to the active substance granules for each tablet:

24.225 mg of sodium carboxymethyl starch
24.000 mg of microcrystalline cellulose
0.500 mg of magnesium stearate 50.000 mg Round, biplanar tablets weighing 50 mg and measuring 5 mm in diameter are compressed from this mixture.

EXAMPLE Z

Tablets containing 1.0 mg of AG-EE 623 ZW

One tablet contains:

1.00 mg of active substance 0.50 mg of N-methylglucamine 0.15 mg of polyvinylpyrrolidone 0.03 mg of polyoxyethylenepolyoxypropylene polymer 0.60 mg of microcrystalline cellulose Preparation:

The active substance and excipients are dissolved in water at 90° C. and the microcrystalline cellulose is suspended therein and the dispersion is evaporated down in vacuo. The dry mass is screened to a mesh size of 1 mm.

The following ingredients are added to the granulated active substance for each tablet:

23.22 mg of sodium carboxymethyl starch
24.00 mg of microcrystalline cellulose
0.50 mg of magnesium stearate 50.00 mg Round, biplanar tablets weighing 50 mg and measuring 5 mm in diameter are compressed from this mixture.

EXAMPLE AA

Tablets containing 1.5 mg of AG-EE 623 ZW

One tablet contains:

1.500 mg of active substance
0.750 mg of N-methylglucamine
0.225 mg of polyvinylpyrrolidone
0.045 mg of polyoxyethylenepolyoxypropylene polymer
0.900 mg of microcrystalline cellulose Preparation:

The active substance and excipients are dissolved in water at 90° C. and the microcrystalline cellulose is suspended therein and the dispersion is evaporated down in vacuo. The dry mass is screened to a mesh size of 1 mm.

The following ingredients are added to the granulated active substance for each tablet:

23.080 mg of sodium carboxymethyl starch
23.000 mg of microcrystalline cellulose
0.500 mg of magnesium stearate 50.000 mg Round, biplanar tablets weighing 50 mg and measuring 5 mm in diameter are compressed from this mixture.

EXAMPLE BB

Tablets containing 2.0 mg of AG-EE 623 ZW

One tablet contains:

2.00 mg of active substance
1.00 mg of L-lysine
1.00 mg of polyvinylpyrrolidone
1.00 mg of polyoxyethylenepolyoxypropylene polymer
4.00 mg of microcrystalline cellulose Preparation:

The ingredients are dissolved in water at 90° C. and the microcrystalline cellulose is suspended therein and the dispersion is processed in a spray dryer. The following ingredients are then added for each tablet:

20.35 mg of microcrystalline cellulose
20.00 mg of sodium carboxymethyl starch
0.65 mg of magnesium stearate 50.00 mg Round, biconvex tablets weighing 50 mg and measuring 5 mm in diameter are compressed from this mixture and are given a flavour-masking coating of hydroxypropylmethylcellulose.

EXAMPLE CC

Tablets containing 2.5 mg of AG-EE 623 ZW

One tablet contains:

2.50 mg of active substance
1.25 mg of L-lysine
1.25 mg of polyvinylpyrrolidone
1.25 mg of polyoxyethylenepolyoxypropylene polymer
4.10 mg of microcrystalline cellulose Preparation:

The ingredients are dissolved in water at 90° C. and the microcrystalline cellulose is suspended therein and the dispersion is processed in a spray dryer. Then the following ingredients are added for each tablet:

21.5 mg of microcrystalline cellulose
21.0 mg of sodium carboxymethyl starch 50.0 mg Round, biconvex tablets weighing 50 mg and measuring 5 mm in diameter are compressed from this mixture and given a flavour-masking coating of hydroxypropylmethyl cellulose.

EXAMPLE DD

Tablets containing 3.0 mg of AG-EE 623 ZW

One tablet contains:

3.0 mg of active substance
1.5 mg of L-lysine
1.5 mg of polyvinylpyrrolidone
1.5 mg of polyoxyethylenepolyoxypropylene polymer Preparation:

The ingredients are dissolved in water at 90° C. and the solution is processed in a spray dryer. Then, for each tablet, the following ingredients are added:

21.5 mg of microcrystalline cellulose
21.0 mg of sodium carboxymethyl starch 50.0 mg Round, biconvex tablets weighing 50 mg and measuring 5 mm in diameter are compressed from this mixture and given a flavour-masking coating of hydroxypropylmethyl cellulose.

EXAMPLE EE

Tablets containing 5 mg of AG-EE 623 ZW

One tablet contains:

5.0 mg of active substance
2.5 mg of L-lysine
2.5 mg of polyvinylpyrrolidone
2.5 mg of polyoxyethylenepolyoxypropylene polymer Preparation:

The ingredients are dissolved in water at 90° C. and the solution is processed in a spray dryer. Then, for each tablet, the following ingredients are added:

19.0 mg of microcrystalline cellulose
18.5 mg of sodium carboxymethyl starch 50.0 mg Round, biconvex tablets weighing 50 mg and measuring 5 mm in diameter are compressed from this mixture and given a flavour-masking coating of hydroxypropylmethyl cellulose.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

What is claimed is:

1. Substantially optically pure (S)(+)-2-ethoxy-4[N-{1-(2-piperidino-phenyl)-3-methyl-1-butyl] aminocarbonylmethyl]-benzoic acid and the salts thereof with inorganic or organic acids or bases.

2. The compound according to claim 1 having an optical purity of at least ee=95%.

3. The compound according to claim 1 having an optical purity of at least ee=98%.

4. The physiologically acceptable salts of the compound according to claim 1 with organic or inorganic acids or bases.

5. A pharmaceutical composition comprising a compound according to claim 1 and one or more inert carriers or diluents.

6. A method for treating diabetes mellitus comprising administering a therapeutically effective amount of the compound as recited in claim 1.

* * * * *